US011779416B2

(12) United States Patent
Traina et al.

(10) Patent No.: US 11,779,416 B2
(45) Date of Patent: Oct. 10, 2023

(54) ROBOTIC SURGICAL SYSTEMS AND INSTRUMENT DRIVE ASSEMBLIES

(71) Applicant: Covidien LP, Mansfield, MA (US)

(72) Inventors: Zachary Traina, Verona, NJ (US); Josiah Rosmarin, Sebring, FL (US)

(73) Assignee: Covidien LP, Mansfield, MA (US)

( * ) Notice: Subject to any disclaimer, the term of this patent is extended or adjusted under 35 U.S.C. 154(b) by 619 days.

(21) Appl. No.: 16/769,865

(22) PCT Filed: Dec. 21, 2018

(86) PCT No.: PCT/US2018/066999
§ 371 (c)(1),
(2) Date: Jun. 4, 2020

(87) PCT Pub. No.: WO2019/135940
PCT Pub. Date: Jul. 11, 2019

(65) Prior Publication Data
US 2021/0169457 A1    Jun. 10, 2021

Related U.S. Application Data

(60) Provisional application No. 62/613,510, filed on Jan. 4, 2018.

(51) Int. Cl.
*A61B 34/35* (2016.01)
*A61B 34/30* (2016.01)
*A61B 17/00* (2006.01)

(52) U.S. Cl.
CPC .............. *A61B 34/35* (2016.02); *A61B 34/30* (2016.02); *A61B 2017/0046* (2013.01);
(Continued)

(58) Field of Classification Search
CPC .......... A61B 2017/00477; A61B 34/30; A61B 34/35
See application file for complete search history.

(56) References Cited

U.S. PATENT DOCUMENTS

| 5,649,956 A | 7/1997 | Jensen et al. |
| 5,842,993 A | 12/1998 | Eichelberger et al. |

(Continued)

FOREIGN PATENT DOCUMENTS

| CN | 1591287 A | 3/2005 |
| CN | 107320184 A | 11/2017 |

(Continued)

OTHER PUBLICATIONS

Japanese Office Action dated Jun. 17, 2021 corresponding to counterpart Patent Application JP 2020-536969.

(Continued)

*Primary Examiner* — Daniel Jeremy Leeds
(74) *Attorney, Agent, or Firm* — CARTER, DELUCA & FARRELL LLP

(57) ABSTRACT

An instrument drive assembly for use with a surgical instrument includes a housing assembly supporting a drive assembly therein, a coupling tube supported at a distal end of the housing assembly and extending distally therefrom, a coupling assembly, and a retention mechanism. The coupling assembly is supported in the housing assembly and is configured to releasably couple to an instrument drive shaft of the surgical instrument, and the retention mechanism is configured to releasably couple to an instrument sleeve of the surgical instrument.

20 Claims, 33 Drawing Sheets

(52) U.S. Cl.
CPC ............... *A61B 2017/00398* (2013.01); *A61B 2017/00477* (2013.01); *A61B 2034/303* (2016.02); *A61B 2034/305* (2016.02)

(56) References Cited

U.S. PATENT DOCUMENTS

| | | |
|---|---|---|
| 6,402,737 B1 | 6/2002 | Tajima et al. |
| 6,758,843 B2 | 7/2004 | Jensen |
| 6,837,883 B2 | 1/2005 | Moll et al. |
| 6,933,695 B2 | 8/2005 | Blumenkranz |
| 7,979,157 B2 | 7/2011 | Anvari |
| 7,983,793 B2 | 7/2011 | Toth et al. |
| 8,343,141 B2 | 1/2013 | Madhani et al. |
| 8,636,192 B2 | 1/2014 | Farascioni et al. |
| 8,828,023 B2 | 9/2014 | Neff et al. |
| 8,925,786 B2 | 1/2015 | Holsten et al. |
| 8,968,312 B2 | 3/2015 | Marczyk et al. |
| 9,220,569 B2 | 12/2015 | Parihar et al. |
| 9,713,466 B2 * | 7/2017 | Kostrzewski .... A61B 17/07207 |
| 2003/0083673 A1 | 5/2003 | Tierney et al. |
| 2004/0049205 A1 | 3/2004 | Lee et al. |
| 2005/0234435 A1 | 10/2005 | Layer |
| 2006/0047365 A1 | 3/2006 | Ghodoussi et al. |
| 2006/0178559 A1 | 8/2006 | Kumar et al. |
| 2007/0239172 A1 | 10/2007 | Lee et al. |
| 2009/0024142 A1 | 1/2009 | Ruiz Morales |
| 2009/0234371 A1 | 9/2009 | Tierney et al. |
| 2010/0175701 A1 | 7/2010 | Reis et al. |
| 2010/0217991 A1 | 8/2010 | Choi |
| 2011/0118754 A1 | 5/2011 | Dachs, II et al. |
| 2011/0174099 A1 | 7/2011 | Ross et al. |
| 2011/0213362 A1 | 9/2011 | Cunningham et al. |
| 2011/0213383 A1 | 9/2011 | Lee et al. |
| 2012/0116416 A1 | 5/2012 | Neff et al. |
| 2012/0150192 A1 | 6/2012 | Dachs, II et al. |
| 2013/0123783 A1 | 5/2013 | Marczyk et al. |
| 2013/0172713 A1 | 7/2013 | Kirschenman |
| 2013/0331858 A1 | 12/2013 | Devengenzo et al. |
| 2014/0012237 A1 | 1/2014 | Pribanic et al. |
| 2014/0039387 A1 | 2/2014 | Kim et al. |
| 2014/0163581 A1 | 6/2014 | Devengenzo et al. |
| 2014/0276761 A1 | 9/2014 | Parihar et al. |
| 2015/0105799 A1 | 4/2015 | Lohmeier et al. |
| 2016/0067001 A1 | 3/2016 | Parihar et al. |
| 2016/0199138 A1 | 7/2016 | Cooper et al. |
| 2016/0303743 A1 | 10/2016 | Rockrohr |
| 2019/0008600 A1 | 1/2019 | Pedros et al. |

FOREIGN PATENT DOCUMENTS

| | | |
|---|---|---|
| JP | 2011507252 | 6/1999 |
| WO | 9639944 A1 | 12/1996 |
| WO | 2006052375 A2 | 5/2006 |
| WO | 2013075204 A1 | 5/2013 |
| WO | 2015088647 A1 | 6/2015 |
| WO | 2016043845 A1 | 3/2016 |
| WO | 2016144998 A1 | 9/2016 |
| WO | 2017116793 A1 | 7/2017 |

OTHER PUBLICATIONS

Indian Office Action dated Apr. 28, 2022 corresponding to counterpart Patent Application IN 202017026813.
Extended European Search Report dated Sep. 24, 2021 corresponding to counterpart Patent Application EP 18898091.6.
Extended European Search Report dated Aug. 2, 2019 corresponding to counterpart Patent Application EP 16882352.4.
Int'l Search Report and Written Opinion of counterpart Int'l Appln PCT/US2016/057788 dated Feb. 3, 2017.
Extended European Search Report dated Jun. 12, 2019 corresponding to counterpart Patent Application EP 16858172.6.
Chinese First Office Action dated Apr. 1, 2020 corresponding to counterpart Patent Application CN 201680059839.
International Search Report dated Apr. 15, 2019 and Written Opinion completed Apr. 15, 2019 corresponding to counterpart Int'l Patent Application PCT/US2018/066999.

* cited by examiner

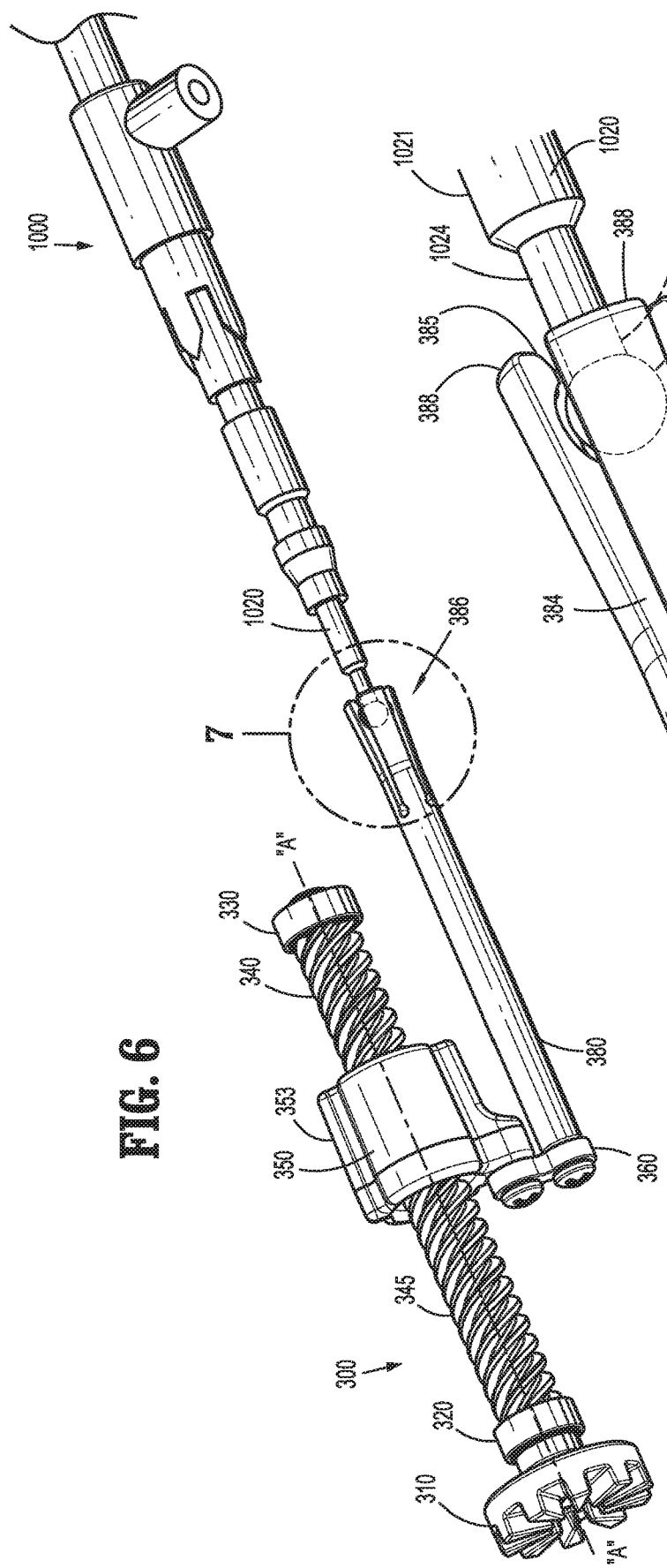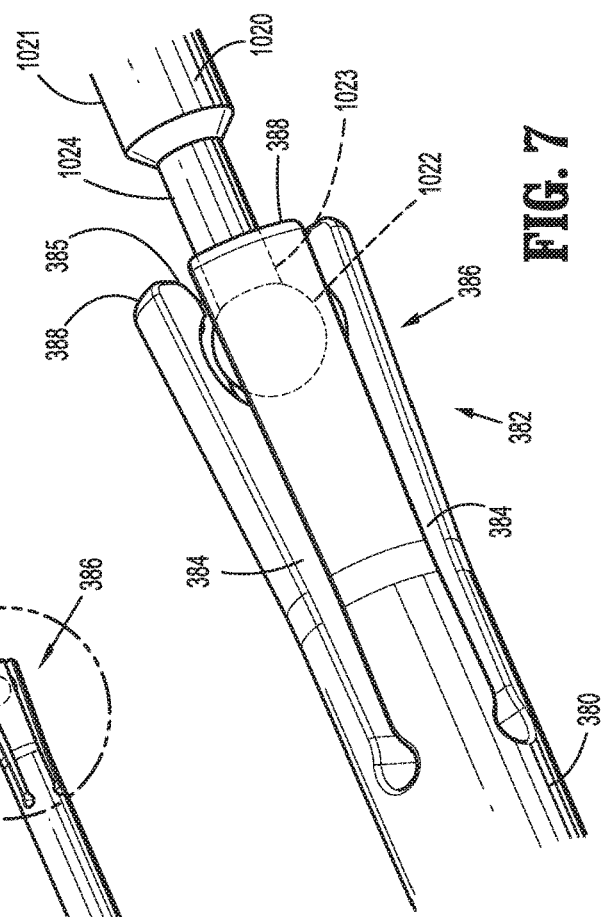

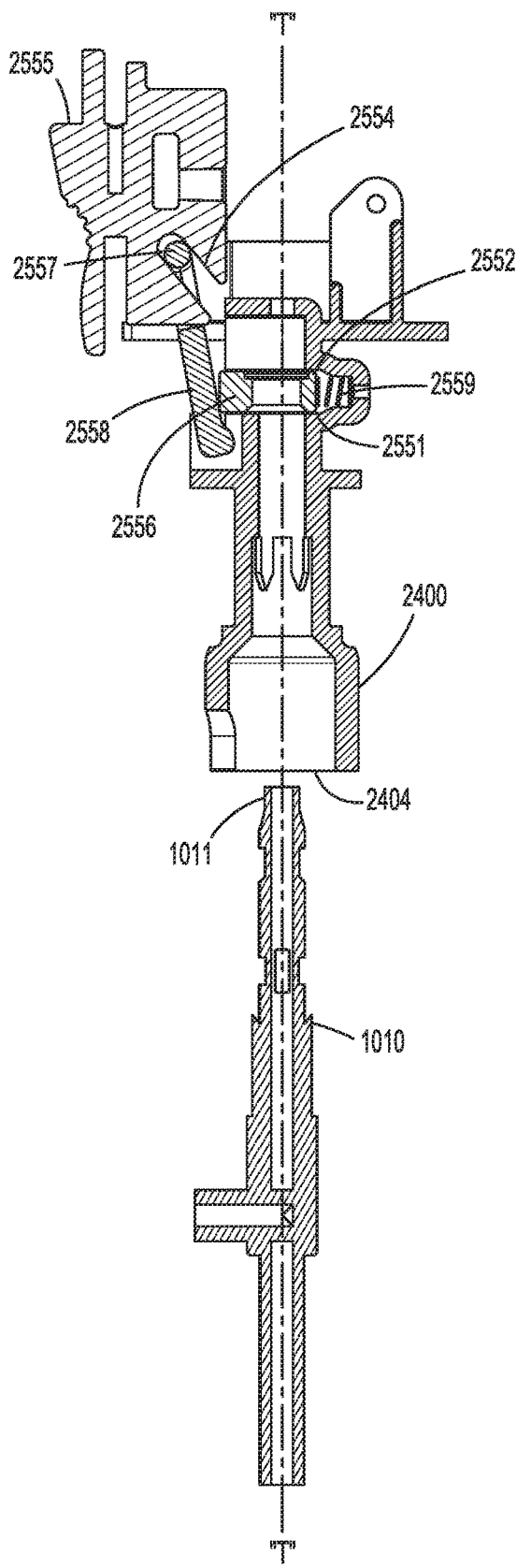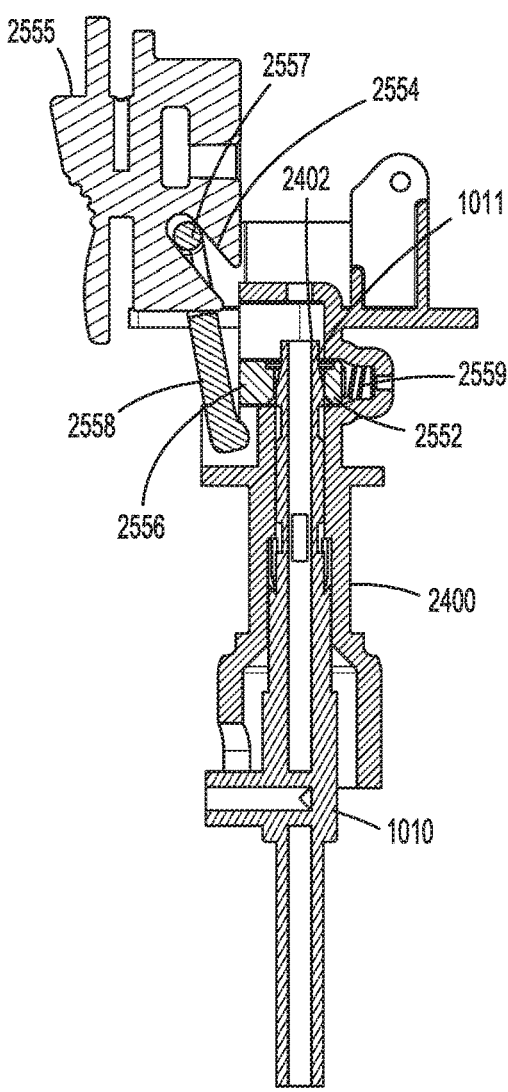
FIG. 18A
FIG. 18B

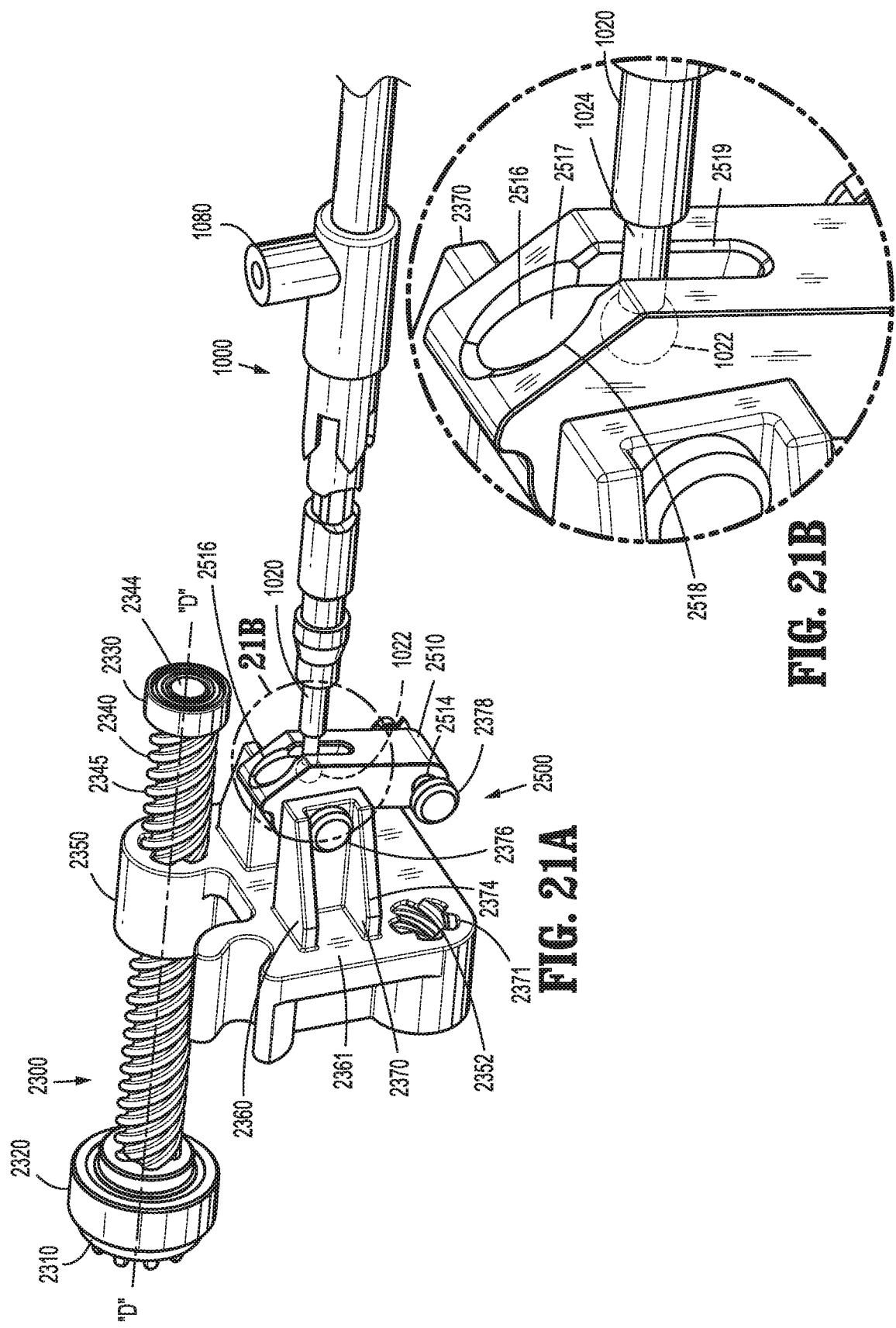

ROBOTIC SURGICAL SYSTEMS AND INSTRUMENT DRIVE ASSEMBLIES

CROSS-REFERENCE TO RELATED APPLICATIONS

This application is a U.S. National Stage Application filed under 35 U.S.C. § 371(a) of International Patent Application Serial No. PCT/US2018/066999, filed Dec. 21, 2018, which claims the benefit of and priority to U.S. Provisional Patent Application Ser. No. 62/613,510, filed Jan. 4, 2018, the entire disclosure of which is incorporated by reference herein.

BACKGROUND

Robotic surgical systems have been used in minimally invasive medical procedures. Some robotic surgical systems include a console supporting a robot arm, and at least one end effector such as forceps or a grasping tool that is mounted to the robot arm via a wrist assembly. During a medical procedure, the end effector and the wrist assembly are inserted into a small incision (via a cannula) or a natural orifice of a patient to position the end effector at a work site within the body of the patient.

In prior robotic surgical systems, cables extend from the robot console, through the robot arm, and connect to the wrist assembly and/or end effector. In some instances, the cables are actuated by means of motors that are controlled by a processing system including a user interface for a surgeon or clinician to be able to control the robotic surgical system including the robot arm, the wrist assembly and/or the end effector.

Prior to or during use of the robotic system, surgical instruments are selected and connected to an instrument drive assembly of each robot arm. For proper installation to be completed, certain connecting features of the surgical instrument must be matingly engaged to corresponding connecting features of the instrument drive assembly. Once these features are matingly engaged, the instrument drive assembly can drive the actuation of the surgical instrument. Accordingly, there is a need for instrument drive assemblies that not only provide quick and easy mechanical and electrical engagement with surgical instruments, but provide a means to couple to a variety of surgical instruments having unique end effectors attached thereto.

SUMMARY

The present disclosure relates to an instrument drive assembly including a housing assembly, a coupling tube, a coupling assembly, and a retention mechanism. The housing assembly supports a drive assembly therein. The coupling tube is supported at a distal end of the housing assembly and extends distally therefrom. The coupling assembly is supported in the housing assembly and is configured to releasably couple to an instrument drive shaft of a surgical instrument. The retention mechanism is configured to releasably couple to an instrument sleeve of the surgical instrument.

In an embodiment, the retention mechanism is supported in the housing assembly and includes a button and a latch plate. The button is slidably coupled to the housing assembly between first and second positions, and including a cam arm. The latch plate is rotationally coupled to the housing assembly and configured to transition between a locked configuration and unlocked configuration, with respect to an instrument sleeve of the surgical instrument. The latch plate includes an arm configured to engage the cam arm of the button and a portion of an instrument sleeve of the surgical instrument. In the first position of the button, the arm of the latch plate is configured to engage a portion of an instrument sleeve of the surgical instrument. In the second position of the button, the cam arm of the button engages the arm of the latch plate such that the latch plate is configured to pivot out of engagement with a portion of an instrument sleeve of the surgical instrument.

In a further embodiment, the retention mechanism includes a first biasing member interposed between the latch plate and the housing assembly, such that the latch plate is biased into one of the locked or unlocked configurations. In an embodiment, the retention mechanism includes a second biasing member interposed between the button and the housing assembly, such that the button is biased into one of the first or second positions.

In yet another embodiment, the coupling assembly includes a drive link pivotably coupled to the housing assembly and a drive screw of the drive assembly. In a further embodiment, proximal and distal translation of the drive screw, with respect to the housing assembly, pivots the drive link between a locked position and an unlocked position.

In yet a further embodiment, the drive link defines a receiving region thereon. The receiving region includes a cavity, a port, and a channel. The cavity is defined within the receiving region and is configured to receive a proximal portion of an instrument drive shaft of the surgical instrument therein. The port extends into the cavity and is configured to receive a proximal portion of an instrument drive shaft of the surgical instrument therethrough. The channel extends along the cavity and is configured to receive a portion of an instrument drive shaft of the surgical instrument distal of a proximal portion of the instrument drive shaft of the surgical instrument therein. The receiving region of the drive link is configured to releasably couple a proximal portion of an instrument drive shaft of the surgical instrument to the drive link.

Further still, in an embodiment, in the unlocked position of the drive link, the drive screw of the drive assembly is in a distal most position and the drive linked is angled an amount sufficient such that the port of the receiving region of the drive link is oriented to fully receive the proximal portion of an instrument drive shaft. In the locked position of the drive link, the drive screw of the drive assembly is in a position proximal of the distal most position and the port of the receiving region defines an angle with respect to the longitudinal axis of the coupling tube.

In yet a further embodiment, in the locked position of the drive link, the cavity of the receiving region is configured to retain therein a proximal portion of an instrument drive shaft of the surgical instrument and the channel of the receiving region is configured to receive therein a portion of an instrument drive shaft of the surgical instrument distal of a proximal portion of an instrument drive shaft of the surgical instrument.

In another embodiment, the drive assembly includes an engagement assembly, whereby the engagement assembly includes a coupling rod, a proximal gear, and a distal gear. The coupling rod includes a proximal portion, a distal portion, and a longitudinal axis defined through a radial center thereof. The proximal gear is disposed at the proximal portion of the coupling rod and is rotationally fixed thereto. The distal gear is disposed at the distal portion of the coupling rod and is rotationally fixed thereto.

In a further embodiment, the drive assembly includes a transfer assembly, whereby the transfer assembly includes a central gear and a stem. The central gear is configured to mesh with the distal gear of the engagement assembly. The stem extends distally from the central gear and defines a recess therein.

In yet a further embodiment, the drive assembly includes at least two engagement assemblies, whereby a distal gear of each engagement assembly enmeshed with the central gear of the transfer assembly.

Further still, in an embodiment, the drive assembly includes a coupler and a drive screw. The coupler defines a threaded aperture, whereby the coupler is rotationally affixed within the recess of the stem. The drive screw includes a threaded portion and a coupling feature. The threaded portion is configured to engage the threated aperture of the coupler, and the coupling feature configured to engage the coupling assembly. Rotation of the proximal gear of the engagement assembly drives rotation of the central gear of the transfer assembly and linear translation of the drive screw, with respect to the housing assembly.

In a further embodiment, the drive assembly includes a stop cap engaged with the housing assembly and disposed about the drive screw distal of the threaded portion thereof.

BRIEF DESCRIPTION OF THE DRAWINGS

Embodiments of the present disclosure are described herein with reference to the accompanying drawings, wherein:

FIG. 6 is a perspective view of an inner drive assembly and a drive member of the instrument drive assembly of FIG. 2 coupled with an instrument drive shaft;

FIG. 7 is a perspective view of the area of detail of FIG. 6;

FIGS. 18A-18C are side views of a retention mechanism of the instrument drive assembly of FIG. 11 in various states of actuation during insertion of an instrument sleeve therein;

FIG. 21A is a perspective view of a drive assembly and a drive link of the instrument drive assembly of FIG. 11 coupled with the instrument drive shaft;

FIG. 21B is a perspective view of the area of detail of FIG. 21A;

DETAILED DESCRIPTION

Figure 1B:
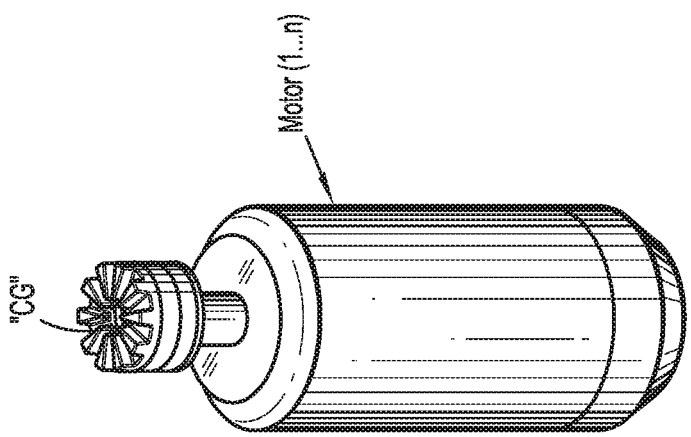
FIG. 1B is a perspective view of a motor of a control device of the medical work station of FIG. 1A.

Embodiments of the presently disclosed instrument drive assemblies are described in detail with reference to the drawings, in which like reference numerals designate identical or corresponding elements in each of the several views. As is used in the art, the term "distal" refers to a position of an instrument, or portion thereof, which is farther from the user, and the term "proximal" refers to a position of an instrument, or portion thereof, which is closer to the user. In addition, all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior" or vice versa.

Figure 1A:
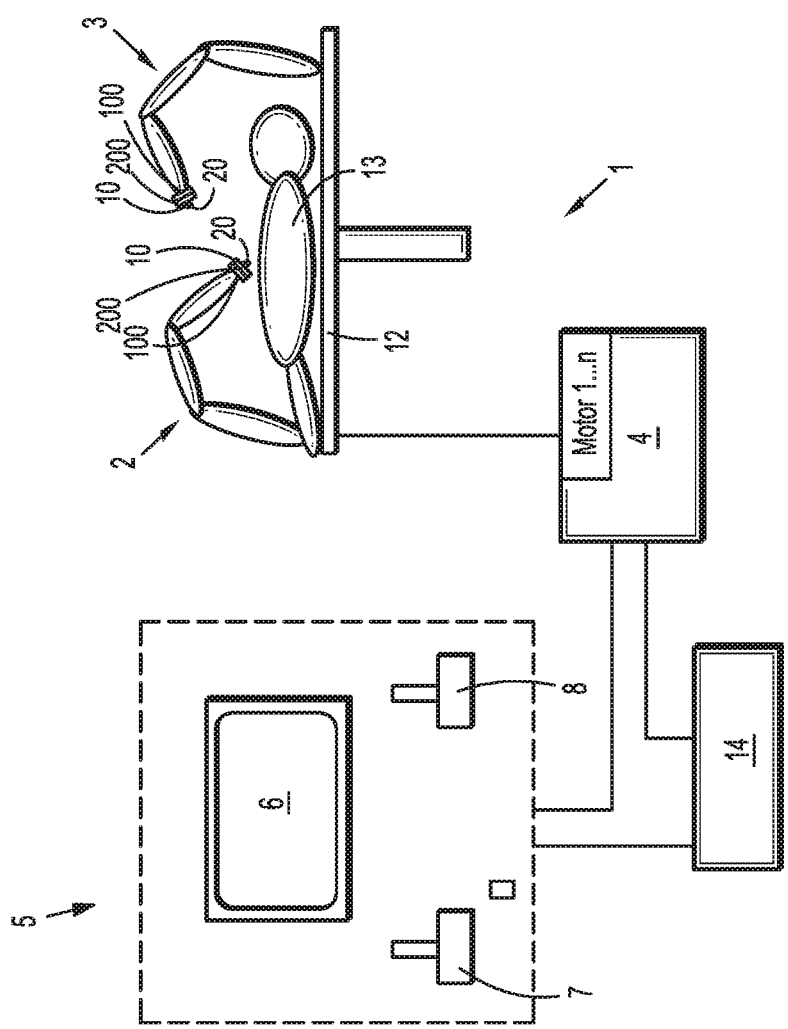
FIG. 1A is a schematic illustration of a medical work station and operating console in accordance with the present disclosure.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an instrument control unit 100, to which may be attached, for example, to an instrument drive assembly 200 of a surgical instrument 1000, the surgical instrument 1000 supporting an end effector (not shown) including, for example, a pair of jaw members, electrosurgical forceps, cutting instruments, or any other endoscopic, or open, surgical devices. For a detailed discussion and illustrative examples of the construction and operation of an end effector for use with instrument control unit 100, reference may be made to commonly owned International patent Application No. PCT/US14/61329, filed on Oct. 20, 2014 (International Patent Publication No. WO 2015/088647, and entitled "Wrist and Jaw Assemblies for Robotic Surgical Systems," now U.S. Patent Publication No. US 2016/0303743, the entire content of which is incorporated herein by reference.

Robot arms 2, 3 may be driven by electric drives (not shown) that are connected to control device 4. Control device 4 (e.g., a computer) is set up to activate the drives, in particular by means of a computer program, in such a way that robot arms 2, 3, instrument control units 100, and thus the surgical instruments 10 execute a desired movement or articulation according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in an open surgery, or a minimally invasive manner, by means of surgical instrument 1000. Medical work station 1 may also include more than two robot arms 2, 3, the additional robot arms likewise being connected to control device 4 and being telemanipulatable by means of operating console 5. An instrument control unit and a surgical instrument may also be attached to the additional robot arm. Medical work station 1 may include a database 14, in particular coupled to or with control device 4, in which pre-operative data from patient 13 and/or anatomical atlases, for example, may be stored.

For a detailed discussion of the construction and operation of medical work station 1 reference may be made to U.S. Pat. No. 8,828,023, filed on Nov. 3, 2011 and entitled "Medical Workstation," the entire content of which is incorporated herein by reference.

Control device 4 may control a plurality of motors (e.g., "M1"-"M6"). Motors "M" may be part of instrument control unit 100 and/or disposed externally of instrument control unit 100. Motors "M" (e.g., motors "M" being located externally of instrument control unit 100) may be configured to rotate a crown gear "CG" (FIG. 1B), or the like, that is keyed to or non-rotatably supported on a rotatable shaft of at least some of motors "M," or act on a cable to draw in or let out length of cable to actuate robot arms 2, 3. In use, as motors "M" are driven, the rotation of crown gear(s) "CG" effects operation, movement, and/or articulation of instrument drive assembly 200 of surgical instrument 1000, and an end effector attached thereto, as discussed below. It is further envisioned that at least one motor "M" receives signals wirelessly (e.g., from control device 4). It is contemplated that control device 4 coordinates the activation of the various motors (Motor 1 . . . n) to coordinate an operation, movement, and/or articulation of robot arms 2, 3 and/or surgical instrument 1000. It is envisioned that each motor may corresponds to a separate degree of freedom of robot arms 2, 3, and/or surgical instrument 1000 engaged with instrument control unit 100. It is further envisioned that more than one motor, including every motor (Motor 1 . . . n), is used for each degree of freedom.

Turning now to FIGS. 2-13, instrument drive assembly 200 is configured to engage instrument control unit 100 at a proximal end 201 thereof and couple to surgical instrument 1000 at a distal end 202 thereof, where surgical instrument 1000 extends distally from instrument drive assembly 200, as described herein. Instrument drive assembly 200 is configured to transfer rotational movement supplied by instrument control unit 100 (e.g., via motors "M") into longitudinal movement of a drive member 380 (FIGS. 5A and 7-10) to effect various functions of surgical instrument 1000.

Figure 4:
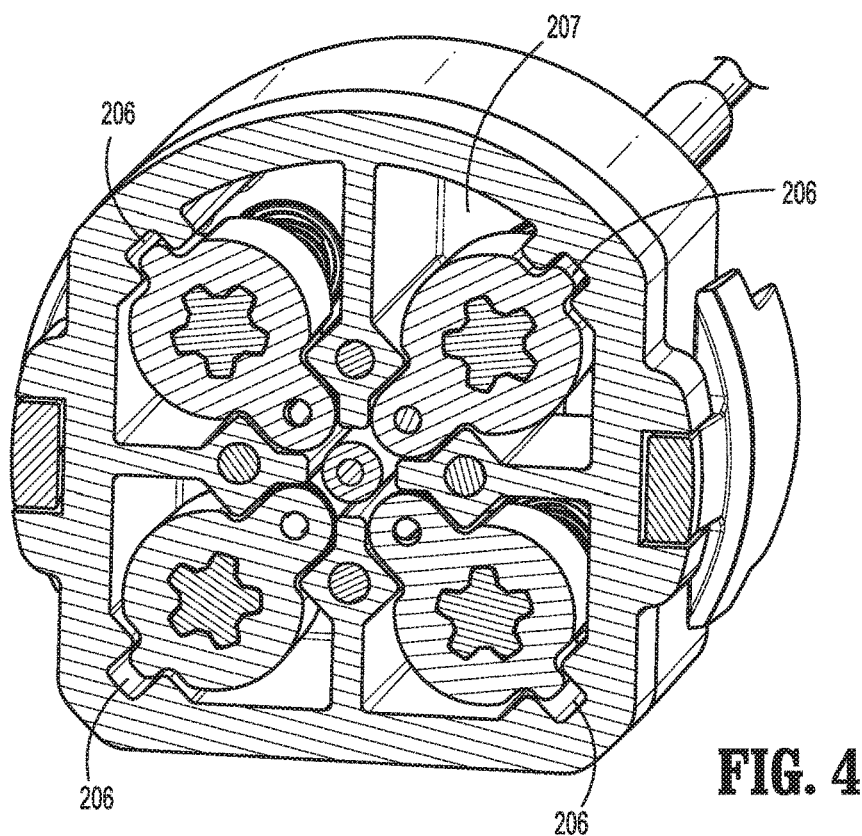
FIG. 4 is a perspective, cross-sectional view of the instrument drive assembly of FIG. 2 taken along the section line 4-4 of FIG. 3.
Figure 5A:
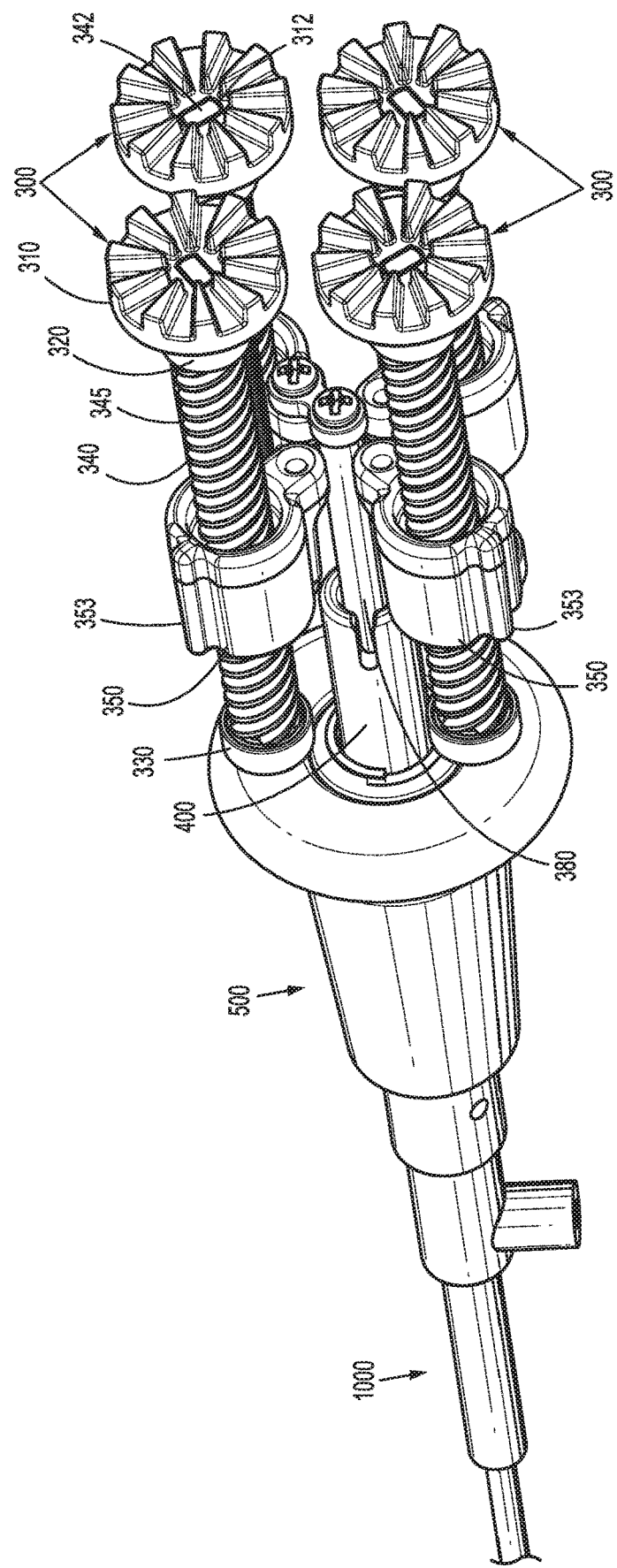
FIG. 5A is a rear perspective view of the instrument drive assembly of FIG. 2 with various parts removed therefrom.
Figure 5B:
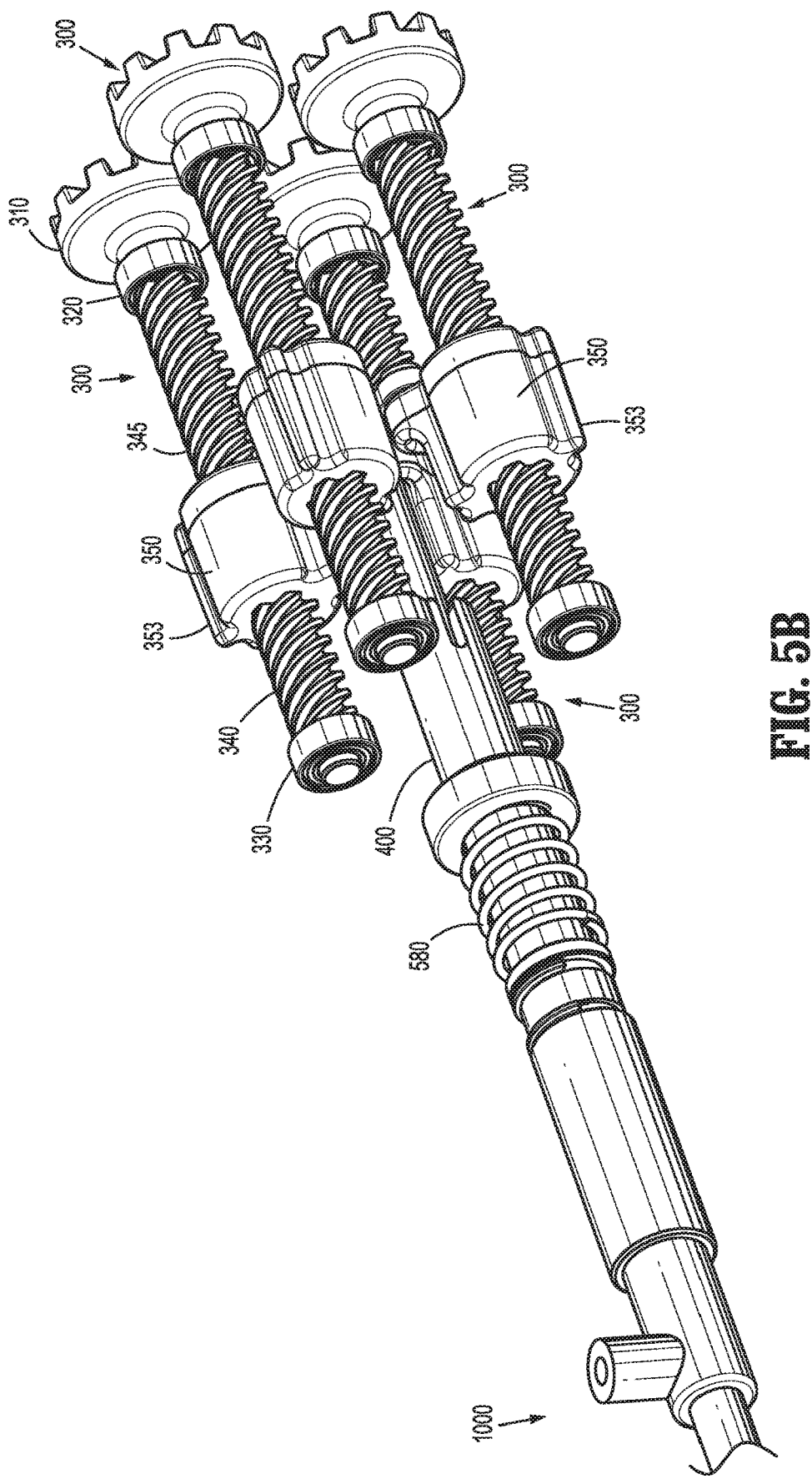
FIG. 5B is a front perspective view of the instrument drive assembly of FIG. 5A.

With reference to FIGS. 2 and 8-10, instrument drive assembly 200 includes a housing assembly 205 which includes a proximal housing 210 and a distal housing 220. Proximal housing 210 and distal housing 220 are releasably couplable to each other, which may facilitate assembly of instrument drive assembly 200, and which may facilitate access, repair, and/or replacement of parts housed at least partially therein. Housing assembly 205 defines at least one bore 207 (as best illustrated in FIG. 4) for housing an inner drive assembly 300 (FIG. 7) therein. It is envisioned that housing assembly 205 includes four separate bores 207, where each bore 207 is at least partially separated from each other and where each bore 207 is configured to house a separate single inner drive assembly 300. Additionally, as discussed below, each respective bore 207 includes a longitudinally-extending channel 206 (e.g., four channels 206) therein (FIG. 4). Each channel 206 is configured to slidingly accept a rail 353 of a drive nut 350 (FIG. 7), as described below. In the illustrated embodiment, instrument drive assembly 200 includes four inner drive assemblies 300, however instrument drive assembly 200 may include more (e.g., five or six) or fewer (e.g., three) inner drive assemblies 300 without departing from the scope of the present disclosure. It is further envisioned that all inner drive assemblies 300, or a select number of inner drive assemblies, may be coupled to one or more respective drive members 380, whereas the exemplary illustration provides a singular inner drive assembly 300 coupled to drive member 380, as described below.

Figure 3:
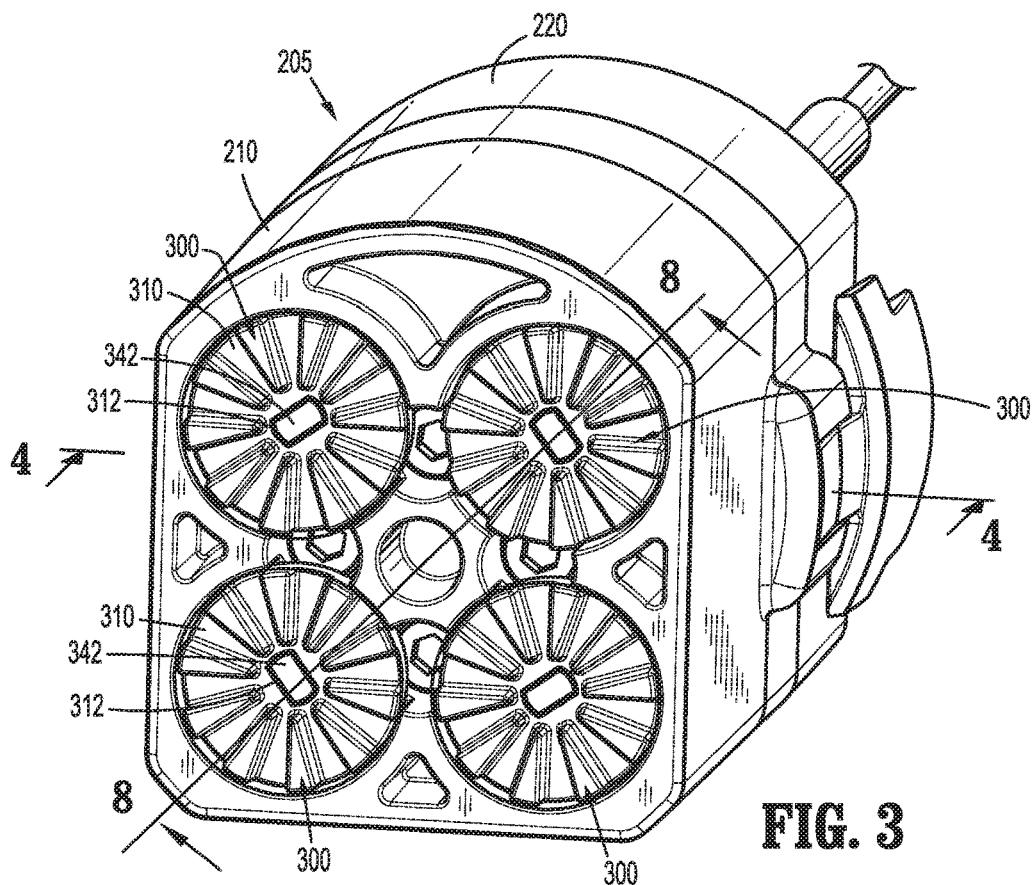
FIG. 3 is rear perspective view of the instrument drive assembly of FIG. 2.

With reference to FIGS. 3, 4 and 7, each inner drive assembly 300 includes a proximal gear 310, a proximal bearing 320, a distal bearing 330, a drive screw 340, and drive nut 350. Drive screw 340 includes a proximal portion 342, a proximal shaft 343, a threaded portion 345 and a distal shaft 344, and defines a longitudinal axis "A-A" extending through a radial center thereof (FIG. 7). Proximal gear 310 is configured to engage, directly or indirectly, with an instrument control gear (e.g., crown gear "CG" of motor "M") of instrument control unit 100, such that rotation of crown gear "CG" causes a corresponding rotation of proximal gear 310. Proximal gear 310 may be a crown gear "CG" that is configured to mate with and/or mesh with crown gear "CG" of motor "M." Proximal gear 310 includes an aperture 312 extending longitudinally therethrough configured to mechanically engage proximal portion 342 of drive screw 340. As shown, aperture 312 and proximal portion 342 of drive screw 340 have corresponding, non-circular cross-sections, such that proximal gear 310 and drive screw 340 are keyed to one another, which results in a rotationally fixed connection therebetween. Rotation of proximal gear 310 causes drive screw 340 to rotate about longitudinal axis "A" in a corresponding direction and rate of rotation.

Figure 9:
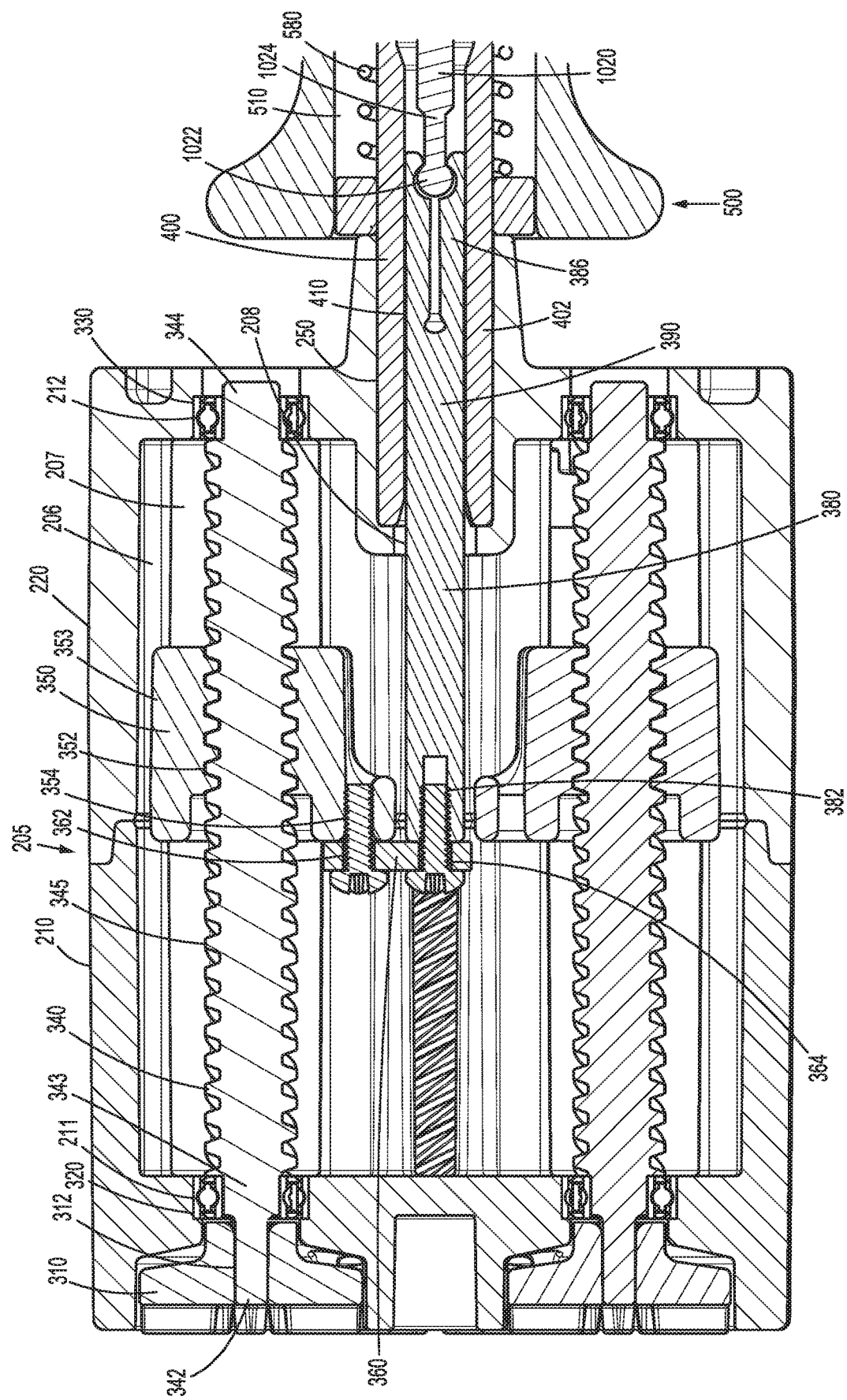
FIG. 9 is a side view of the area of detail of FIG. 8A.
Figure 10:
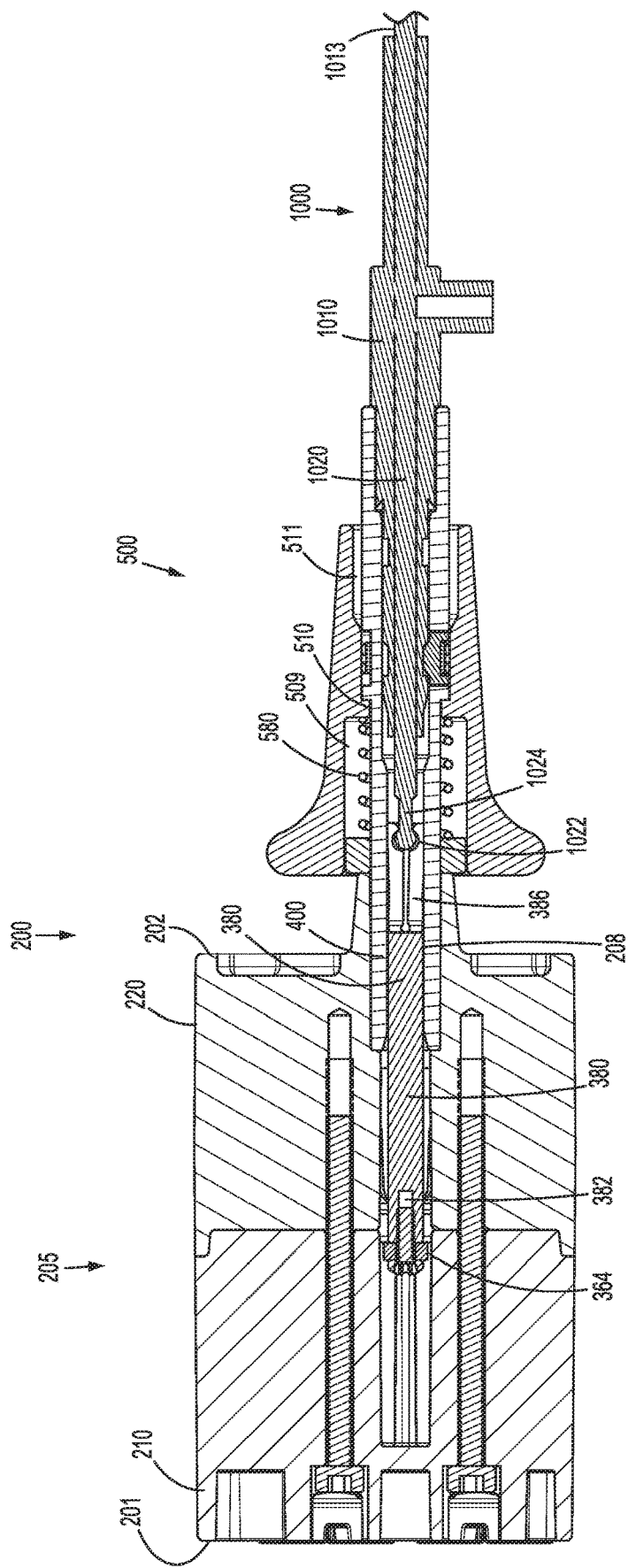
FIG. 10 is a side, cross-sectional view of the instrument drive assembly of FIG. 2 taken along section line 10-10 of FIG. 2.

Drive nut 350 includes a threaded aperture 352 extending longitudinally therethrough, which is configured to mechanically engage threaded portion 345 of drive screw 340. That is, drive nut 350 and drive screw 340 are threadingly engaged with each other. Drive nut 350 includes rail 353 extending longitudinally along an outer surface thereof and is configured to be slidably disposed in the longitudinally extending channel 206 formed in bore 207 of housing assembly 205 (FIGS. 6 and 9). Rail 353 of drive nut 350 cooperates with channel 206 of bore 207 to inhibit or prevent drive nut 350 from rotating about longitudinal axis "A" as drive screw 340 is rotated. Accordingly, drive nut 350 is configured to be positioned on drive screw 340 in a manner such that rotation of drive screw 340 causes longitudinal translation of drive nut 350. More specifically, rotation of proximal gear 310 in a first direction (e.g., clockwise) causes drive screw 340 to rotate in a corresponding first direction and drive nut 350 to translate in a first longitudinal direction (e.g., proximally) with respect to proximal gear 310, and rotation of proximal gear 310 in a second direction (e.g., counter-clockwise) causes drive screw 340 to rotate in a corresponding second direction and drive nut 350 to translate in a second longitudinal direction (e.g., distally) with respect to proximal gear 310.

Drive nut 350 further defines a bore-hole 354 laterally offset from, and parallel to, threaded aperture 352. It is contemplated that bore-hole 354 may define threads on an inner surface such that drive nut 350 may be coupled to drive member 380, as discussed below.

As illustrated (FIGS. 5A and 9), the drive nut 350 of one inner drive assembly 300 is coupled to drive member 380, where drive member 380 may define, for example, a drive bar or push bar, as described below. A link bar 360 defining two bore-holes 362, 364 laterally offset from one another is configured to couple drive nut 350 and drive member 380 (FIGS. 7 and 9). It is contemplated that a respective link bar 360 may be provided for each respective inner drive assembly 300, or a select number of link bars 360 may be provided for a select number of inner drive assemblies 300, such that each drive nut 350 of the respective inner drive assembly 300 may be coupled to either a respective drive member 380, or the same drive member 380.

Link bar 360 may be monolithically formed with drive nut 350, drive member 380, or both drive nut 350 and drive member 380, such that drive nut 350, link bar 360, and drive member 380 consist of one unitary body. Alternatively, drive nut 350, link bar 360, and drive member 380 may be fastened by any mechanical means known in the art, such as, for example, by utilizing a screw or bolt. In such an embodiment, bore-holes 362, 364 of link bar 360 may define threads on an inner surface thereof, such that a bolt or screw may be threadably engaged between link bar 360 and drive nut 350, and link bar 360 and drive member 380. More specifically, a screw may be threadably engaged through bore-hole 362 of link bar 360 and bore-hole 354 of drive nut 350, thereby securing link bar 360 thereto. An additional screw may be threadably engaged through bore-hole 364 of link bar 360 and a bore-hole 382 of drive member 380, thereby securing link bar 360 thereto. With drive nut 350 coupled to drive member 380, it should be appreciated that proximal and distal translation of drive nut 350 with respect to proximal gear 310 results in a corresponding proximal or distal translation of drive member 380, as discussed in further detail below.

With inner drive assembly 300 and housing assembly 205 assembled, proximal bearing 320 is disposed in a proximal bearing cavity 211 of proximal housing 210, and distal bearing 330 is disposed in a distal bearing cavity 212 of distal housing 220 (FIG. 9). Each of proximal bearing 320 and distal bearing 330 facilitate rotation of drive screw 340 with respect to housing assembly 205, and may further serve as proximal and distal stops, respectively, for drive nut 350.

Drive member 380 extends distally from link bar 360, through a central bore 208 (FIGS. 8-10) of housing assembly 205, and is configured to mechanically engage a portion of surgical instrument 1000, as described herein. Longitudinal translation of drive member 380 is configured to drive a function of the end effector disposed at a distal end of surgical instrument 1000. For example, surgical instrument 1000 may include a first end effector configured such that distal translation of drive member 380 directs a pair of jaw members of a clamping device to move into approximation with respect to one another, and proximal translation of drive member 380 may be configured to move at least one jaw member into a spaced apart position with respect to the other jaw member. It should be appreciated that proximal and distal translation of drive member 380 may be configured to effect operation, articulation, or actuation of any number of unique end effectors of a respective surgical instruments 1000, such as, for example, actuation of a cutting blade and/or initiation of the delivery of electrosurgical energy to tissue, etc.

Figure 2:
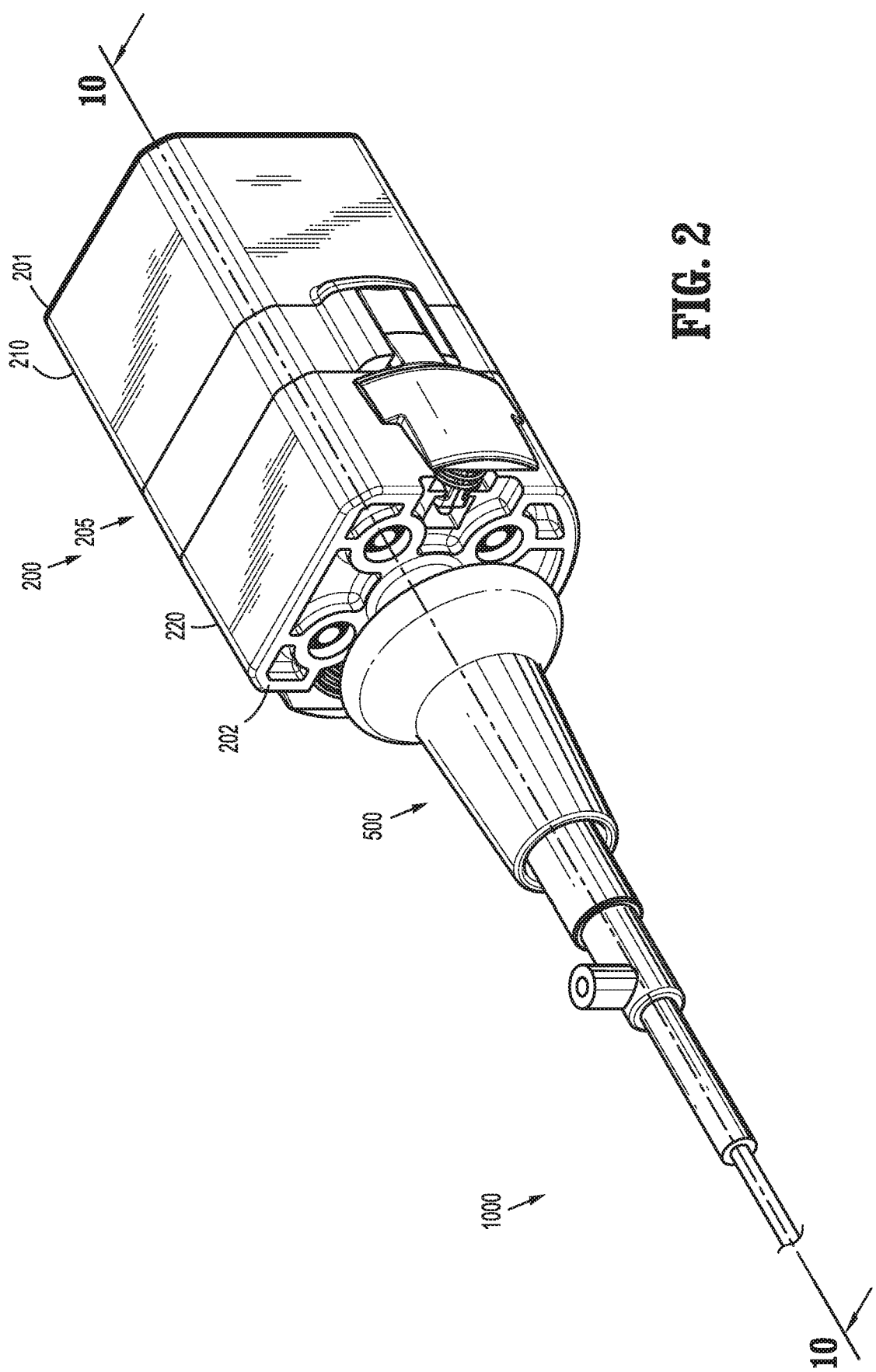
FIG. 2 is a perspective view of an instrument drive assembly in accordance with an embodiment of the present disclosure.
Figure 8A:
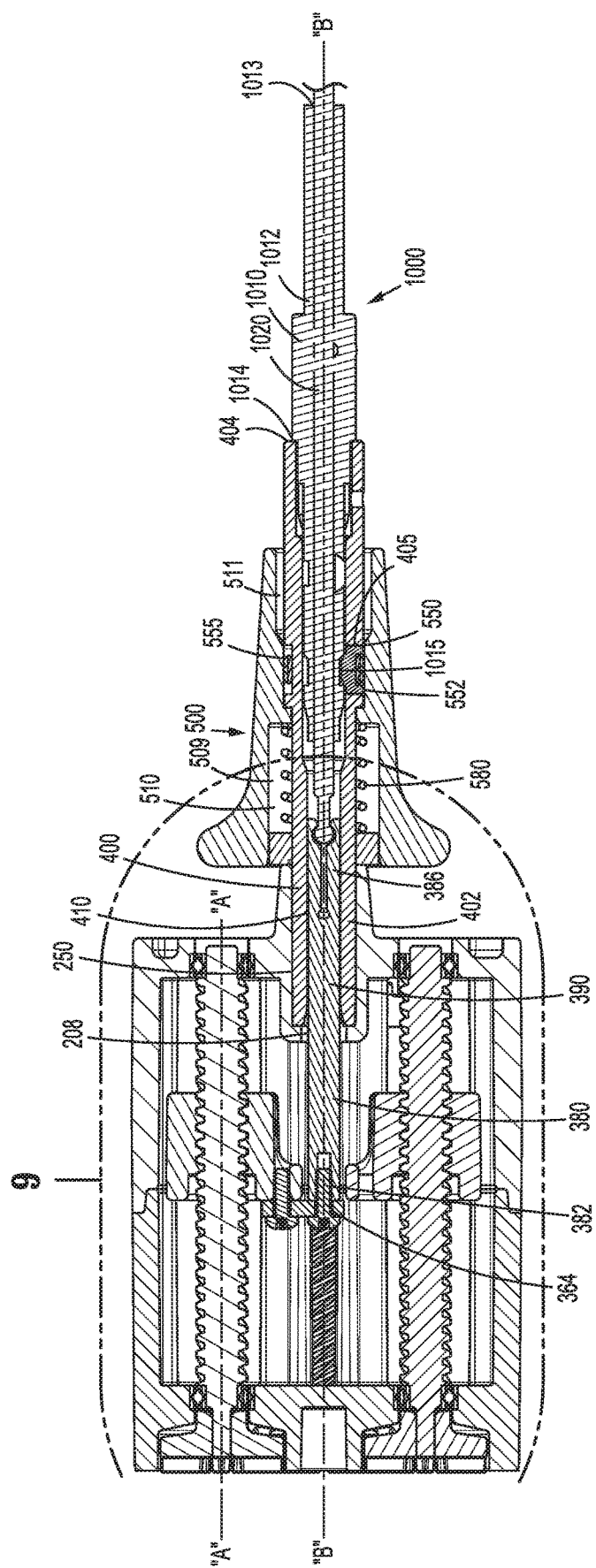
FIG. 8A is a side, cross-sectional view of the instrument drive assembly of FIG. 2 taken along section line 8-8 of FIG. 3 with a coupling assembly in a distal position.
Figure 8B:
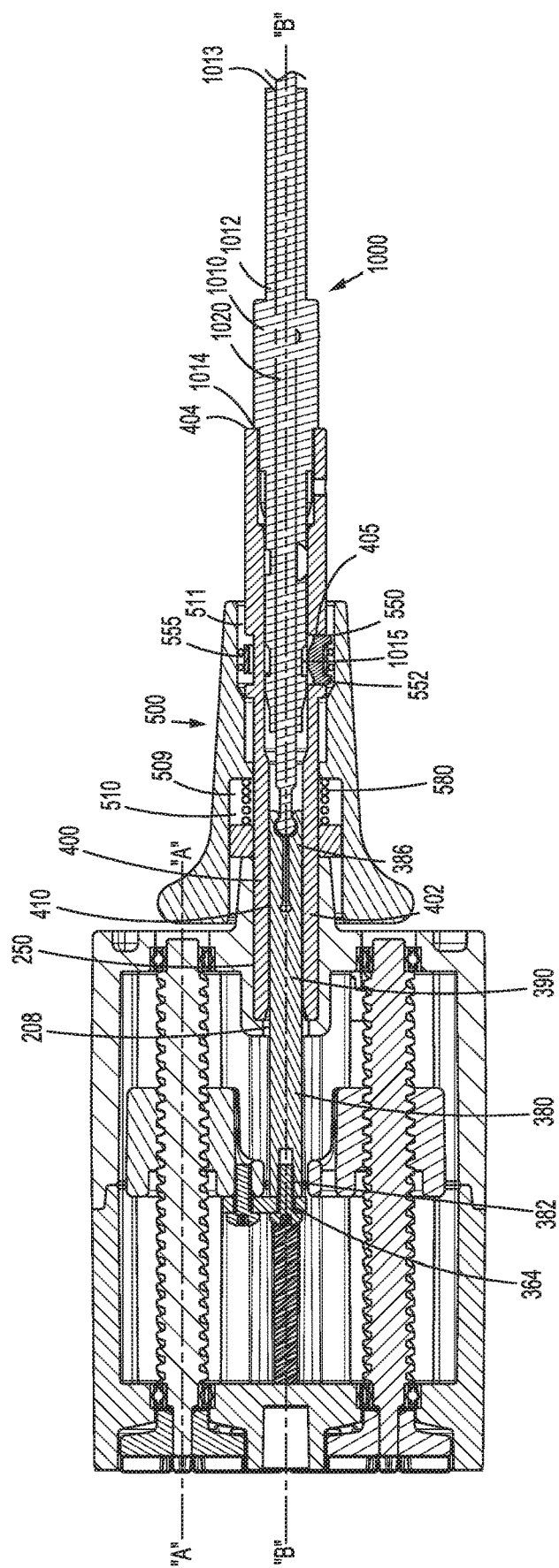
FIG. 8B is a side, cross-sectional view of the instrument drive assembly of FIG. 2 taken along section line 8-8 of FIG. 3 with the coupling assembly in a proximal position.

With reference to FIGS. 2, 8A and 8B, the engagement of surgical instrument 1000 to instrument drive assembly 200, and more particularly to housing assembly 205 and drive member 380, will be described. Housing assembly 205 further includes a coupling assembly 500 disposed distally of distal end 202 of housing assembly 205. Coupling assembly 500 serves to releasably couple surgical instrument 1000 to housing assembly 205, and releasably couple an instrument drive shaft 1020 of surgical instrument 1000 to drive member 380 (FIGS. 8A-10).

Briefly, surgical instrument 1000 may include an instrument sleeve 1010, which defines a longitudinally extending lumen 1012 configured to receive at least a portion of instrument drive shaft 1020 therein, and an end effector (not shown) coupled to, and disposed at, a distal end of instrument drive shaft 1020. Instrument drive shaft 1020 is configured to translate longitudinally within the lumen 1012 of instrument sleeve 1010, such that instrument drive shaft 1020 controls actuation, articulation, and/or firing of the end effector, such as, for example, approximation of first and second jaw members to grasp tissue therebetween, advancement of a knife blade to sever tissue, articulation of the orientation and/or direction of the end effect, and/or any other function described herein or known in the art. More specifically, through proximal and distal translation of instrument drive shaft 1020, with respect to instrument sleeve 1010, instrument drive shaft 1020 actuates the end effector. For example, translation of instrument drive shaft 1020 in a first direction (e.g., distally), may cause a first and second jaw member (not shown) to move into a spaced apart configuration with respect to one another such that tissue may be disposed therebetween, and translation of instrument drive shaft 1020 in a second direction (e.g., proximally) may cause the first and second jaw members to move into an approximated configuration with respect to one another such that tissue disposed therebetween is securely grasped. It should be appreciated that the above examples are exemplary in nature, and the instrument drive shaft 1020 and end effector may be configured to actuate in any number of ways.

With reference to FIGS. 8A-10, a coupling tube 400 serves to interconnect housing assembly 205 and coupling assembly 500. Coupling tube 400 includes a proximal portion 402 disposed in a distal cavity 250 of distal housing 220 of housing assembly 205, and extends distally therefrom. Distal cavity 250 is coaxial with central bore 208 of housing assembly 205 and is configured to receive a diameter of coupling tube 400 therein. As illustrated, a longitudinally extending lumen 410 of coupling tube 400 is configured to slidingly receive a distal portion 390 of drive member 380 therein, such that a portion of drive member 380 is translatable therethrough. Coupling tube 400 extends distally through a longitudinal cavity 510 of coupling assembly 500, such that coupling assembly 500 is slidably supported thereon, as discussed below. As such, it should be appreciated that central bore 208 of housing assembly 205, drive member 380, coupling tube 400, and longitudinal cavity 510 of coupling assembly 500 are coaxial.

Coupling assembly 500 is longitudinally translatable along coupling tube 400 between a proximal position (FIG. 8B) and a distal position (FIG. 8A), with respect to housing assembly 205. As will be described below, in the proximal position, instrument sleeve 1010 of surgical instrument 1000 is releasably coupled to coupling assembly 500 and instrument drive shaft 1020 is releasably coupled to drive member 380; and in the distal position, instrument sleeve 1010 is securely coupled to coupling assembly 500 and instrument drive shaft 1020 is securely coupled to drive member 380. It is envisioned that coupling assembly 500 may additionally aid alignment of instrument drive shaft 1020 and drive member 380 during coupling.

More specifically, instrument sleeve 1010 of surgical instrument 1000 is slidably inserted into a distal opening 404 of coupling tube 400. A notch 1014 extending outward from an outer surface of instrument sleeve 1010 is configured to abut distal end 404 of coupling tube 400 when instrument sleeve 1010 of surgical instrument 1000 is fully inserted therein. It is further envisioned that coupling assembly 500 provides a retention mechanism 550, such that instrument sleeve 1010 of surgical instrument 1000 is releasably retained or secured within coupling tube 400, and thus, releasably secured to coupling assembly 500 and thus housing assembly 205. As will be described herein below, retention mechanism 550 is transitionable between a locked configuration and an unlocked configuration.

It is contemplated that as instrument sleeve 1010 of surgical instrument 1000 slides proximally within coupling tube 400, a button or biasing member 552 disposed in longitudinal cavity 510 of coupling assembly 500 is configured to engage a recess 1015 disposed on the outer surface of instrument sleeve 1010. As best illustrated in FIGS. 8A and 8B, button 552 may be disposed in longitudinal cavity 510 such that it resides in a radial cavity 405 extending through a portion of coupling tube 400. It should be appreciated that button 552 translates radially inward with respect to a longitudinal axis "B" (FIG. 8A) of coupling tube 400 to engage instrument sleeve 1010 of surgical instrument 1000 in the locked configuration, and translates radially outward (FIG. 8B) to disengage instrument sleeve 1010 in the unlocked configuration. With button 552 in the locked configuration, button 552 is engaged with recess 1015 such that longitudinal translation of instrument sleeve 1010 of surgical instrument 1000, within coupling tube 400, is inhibited, and in the unlocked configuration, button 552 is disengaged from recess 1015 such that instrument sleeve 1010 freely slides proximally and distally within coupling tube 400. Radial cavity 405 may be transverse to the longitudinal axis "B" of coupling tube 400, such that when button 552 actuates between the locked and unlocked configurations, button 552 translates perpendicular to coupling tube 400, and instrument sleeve 1010 of surgical instrument 1000 inserted therein. Alternatively, radial cavity 405 and button 552 may be configured such that button 552 translates at an angle with respect to the longitudinal axis "B" of coupling tube 400, such that button 552 slides into and out of engagement with recess 1015 of instrument sleeve 1010 of surgical instrument 1000.

It is further contemplated that retention mechanism 550 may be disposed proximally of distal end 404 of coupling tube 400, such that instrument sleeve 1010 of surgical instrument 1000 slides within coupling tube 400 in a proximal direction an initial distance prior to engaging button 552 of retention member 550. It is further envisioned that a biasing member 555 may be disposed within longitudinal cavity 510 of coupling assembly 500 which is configured to bias button 552 into the locked configuration. Biasing member 555 may include a spring element disposed within radial cavity 405 in abutment with both button 552 and longitudinal cavity 510 and/or coupling tube 400. With button 552 biased into the locked configuration, as instrument sleeve 1010 slides proximally, the bias member 555 is overcome and button 552 is urged radially outward into the unlocked configuration. Once instrument sleeve 1010 is translated proximally the initial distance, recess 1015 is aligned with button 552, permitting button 552 to return to the locked configuration.

As referenced above, coupling assembly 500 of housing assembly 205 is slidably supported on coupling tube 400 between a proximal position and a distal position with respect to housing assembly 205. With coupling assembly 500 in the distal position, e.g., a locked configuration, button 552 of retention mechanism 550 is maintained in the locked configuration with respect to instrument sleeve 1010 of surgical instrument 1000, and with coupling assembly 500 in the proximal position, e.g., an unlocked configuration, button 552 may be actuated into the unlocked configuration with respect to instrument sleeve 1010. Thus, translation of coupling assembly 500 permits the locking and unlocking of instrument sleeve 1010 of surgical instrument 1000.

It should be appreciated that a distal portion 511 of longitudinal cavity 510 of coupling assembly 500 defines a larger diameter, such that when coupling assembly 500 is in the proximal position, distal portion 511 of the longitudinal cavity 510 aligns with button 552, such that button 552 is disposed therein and thus permitted to translate radially outward into the unlocked configuration with respect to instrument sleeve 1010 of surgical instrument 1000.

It is contemplated that coupling assembly 500 further includes a biasing element 580, such that coupling assembly 500 is biased into the distal position, e.g., the locked configuration. In an exemplary illustration, biasing element 580 is disposed in a proximal portion 509 of longitudinal cavity 510, however it is envisioned that biasing element 580 may be disposed in any portion of coupling assembly 500. More specifically, when uncoupling surgical instrument 1000 from instrument drive assembly 200, coupling assembly 500 is translated proximally, such that button 552 aligns with the distal portion 511 of the longitudinal cavity 510 of coupling assembly 500, and such that button 552 may translate radially outward, out of engagement with recess 1015 of instrument sleeve 1010. With button 552 disengaged, instrument sleeve 1010 is permitted to slide distally to be removed from coupling tube 400, and instrument drive assembly 200.

With reference to FIGS. 7-9, engagement of drive member 380 of inner drive assembly 300 and instrument drive shaft 1020 of surgical instrument 1000 will be discussed. As best illustrated in FIG. 7, a distal portion 382 of drive member 380 defines an engagement region 386. Engagement region 386 of drive member 380 includes a plurality of longitudinally extending slits 384, where each slit 384 is disposed about a circumference of a distal end 388 of drive member 380, and extends proximally therefrom along a portion of drive member 380. As a result of the plurality of longitudinally extending slits 384, the engagement region 386 of drive member 380 forms an expandable leaf feature, and may thus flex radially outward to facilitate the releasable coupling of instrument drive shaft 1020 of surgical instrument 1000 therewith. It is further envisioned that an inner surface of retention region 386 of drive member 380 may define an arcuate cavity, e.g., a socket joint, configured to receive a coupling ball 1022 of instrument drive shaft 1020 of surgical instrument 1000, as described below. It is contemplated that engagement region 386 of drive member 380 further includes retention hooks 385 disposed at the distal end 388 of drive member 380 on an inner facing surface thereof, where retention hooks 385 facilitate retention of coupling ball 1022 of instrument drive shaft 1020 therein.

More specifically, instrument drive shaft 1020 of surgical instrument 1000 includes a neck 1024 extending proximally from a proximal end 1021 thereof, where coupling ball 1022 (shown in phantom in FIG. 7) is disposed at a proximal end 1023 of neck 1024. It is contemplated that coupling ball 1022, neck 1024, and instrument drive shaft 1020 may be coupled by any means known in the art and/or may be monolithically formed. A diameter of neck 1024 may be smaller than a diameter of coupling ball 1022, such that when coupling ball 1022 is received within retention region 386 of drive member 380, retention hooks 385 of retention region 386 surround and enclose coupling ball 1022, thus providing further securement therein. When coupling drive member 380 of inner drive assembly 300 and instrument drive shaft 1020 of surgical instrument 1000, the coupling ball 1022 of instrument drive shaft 1020 is brought into approximation with retention region 386 of drive member 380. As instrument drive shaft 1020 is moved proximally with respect to drive member 380, coupling ball 1022 urges retention region 386 to flex radially outward, such that coupling ball 1022 is received therein. With coupling ball 1022 received within retention region 386, coupling ball 1022 is thereby releasably coupled to drive member 380. With drive member 380 coupled to instrument drive shaft 1020, proximal and distal translation of drive member 380 directs a corresponding proximal and distal translation of instrument drive bar 1020.

To uncouple instrument drive shaft 1020 of surgical instrument 1000 from drive member 380 of inner drive assembly 300, instrument drive bar 1020 is moved distally with respect to drive member 380, such that coupling ball 1022 is pulled out of, and released from, retention region 386.

During use, with instrument drive assembly 200 in an active state (e.g., when motor(s) "M" of instrument control unit 100 rotate proximal gear(s) 310), rotation of proximal gear 310 results in a corresponding rotation of drive screw 340. Rotation of drive screw 340 causes longitudinal translation of drive nut 350 due to the engagement between threaded portion 345 of drive screw 340 and threaded aperture 352 of drive nut 350. As discussed above, the direction of rotation of proximal gear 310, and thus drive screw 340, determines the direction of longitudinal translation of drive nut 350. With instrument sleeve 1010 of surgical instrument 1000 coupled to coupling assembly 500, and instrument drive shaft 1020 coupled to drive member 380, rotation of proximal gear 310 directs linear translation of drive member 380 and instrument drive shaft 1020. More specifically, rotation of proximal gear 310 in a first direction (e.g., clockwise) causes drive screw 340 to rotate in a corresponding first direction and drive nut 350 to translate in a first longitudinal direction (e.g., proximally) with respect to proximal gear 310, which translates drive member 380 and instrument drive shaft 1020 in a corresponding first longitudinal direction (e.g., proximally). Rotation of proximal gear 310 in a second direction (e.g., counter-clockwise) causes drive screw 340 to rotate in a corresponding second direction and drive nut 350 to translate in a second longitudinal direction (e.g., distally) with respect to proximal gear 310, which translates drive member 380 and instrument drive shaft 1020 in a corresponding second longitudinal direction (e.g., distally).

With reference to FIGS. 11-21B, an alternate embodiment of instrument drive assembly 200, in accordance with the present disclosure, will be described with reference to instrument drive assembly 2000. As discussed below, instrument sleeve 1010 and instrument drive shaft 1020 of surgical instrument 1000 are also releasably couplable to instrument drive assembly 2000.

Figure 11:
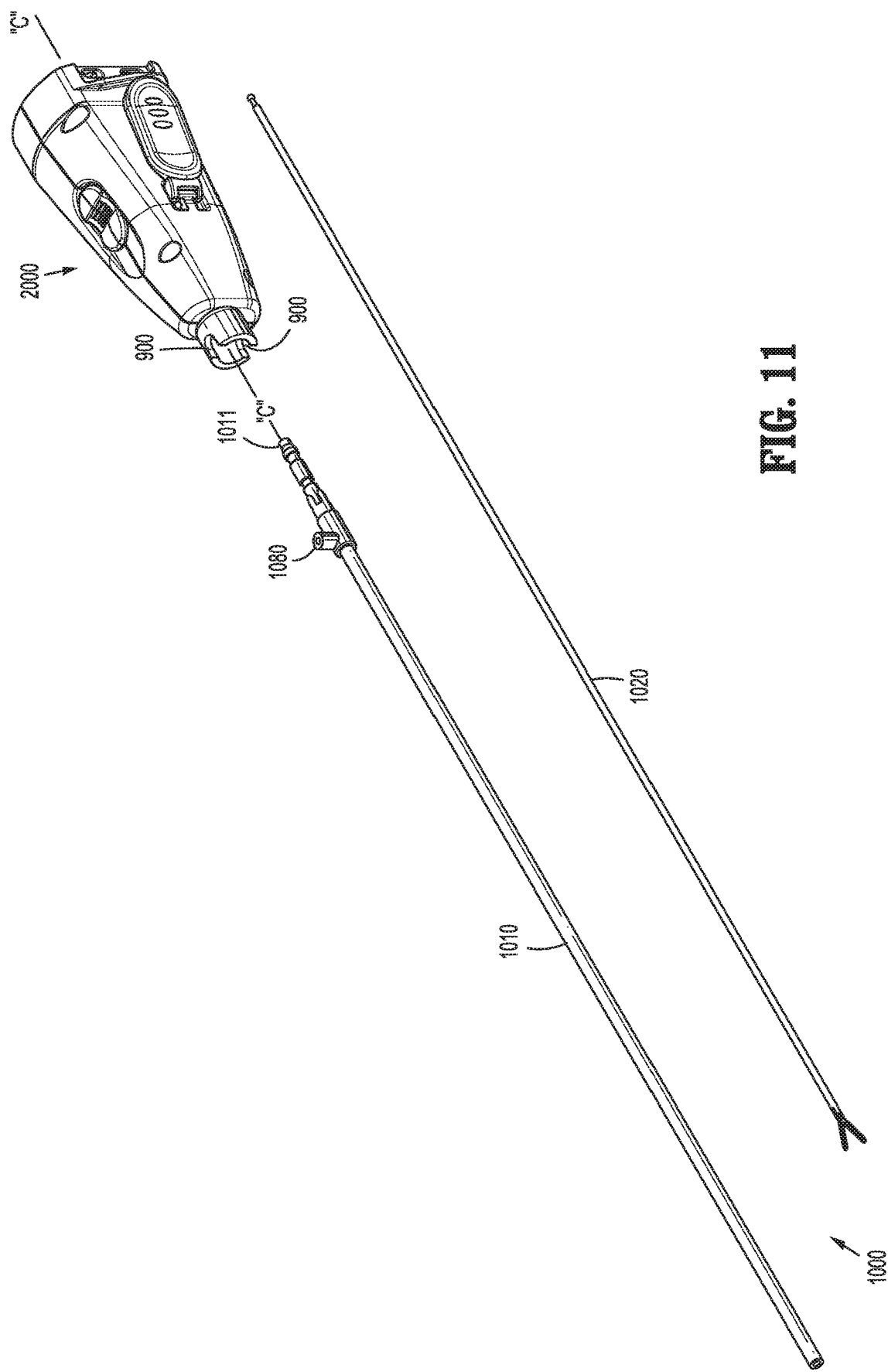
FIG. 11 is a perspective view of an instrument drive assembly in accordance with another embodiment of the present disclosure.
Figure 12:
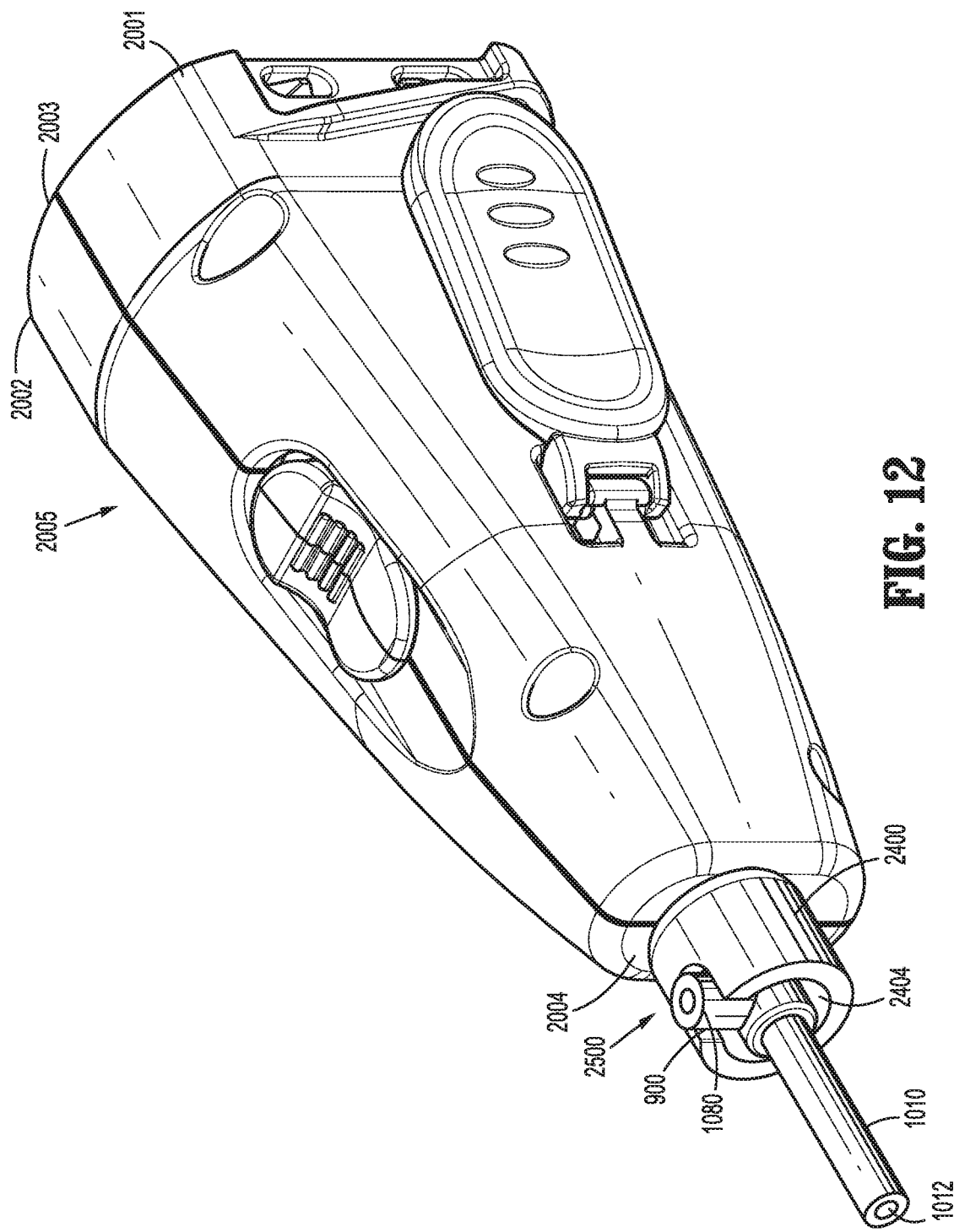
FIG. 12 is a front perspective view of the instrument drive assembly of FIG. 11.
Figure 13:
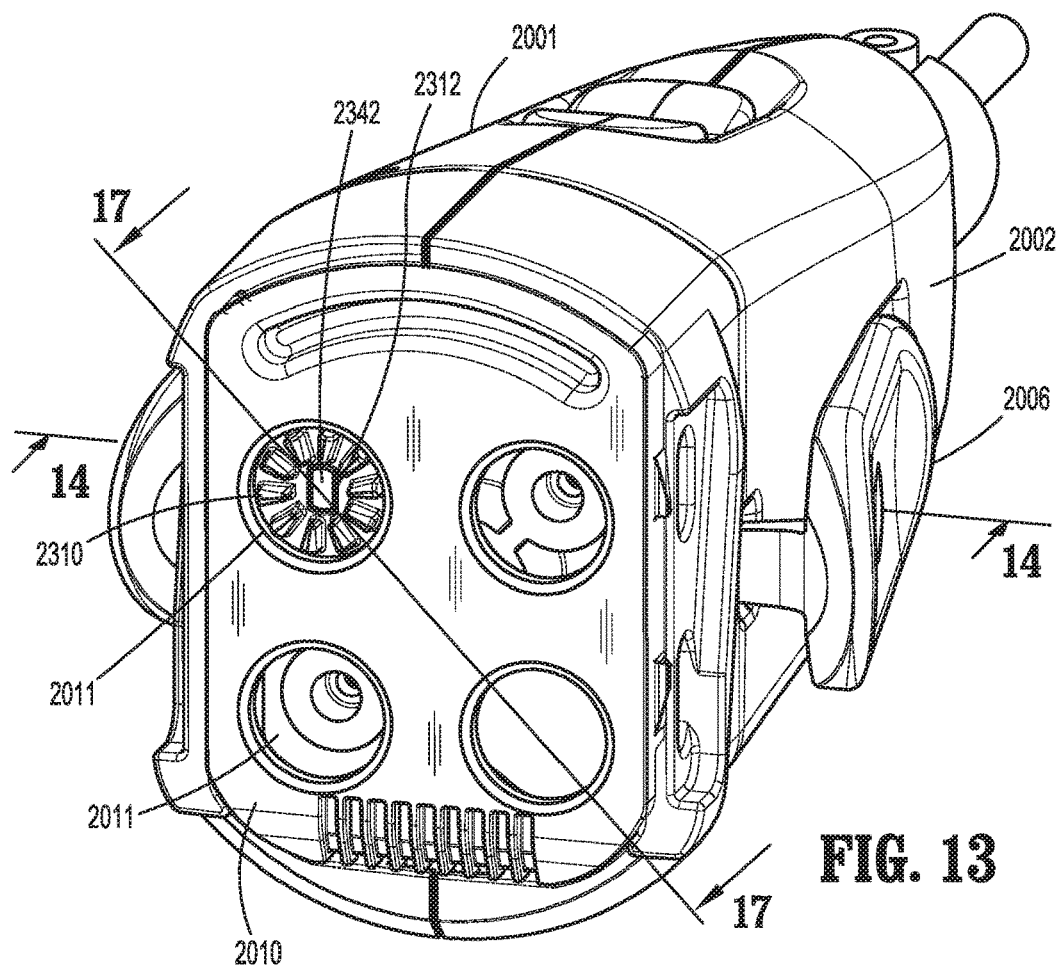
FIG. 13 is a rear perspective view of the instrument drive assembly of FIG. 11.
Figure 14:
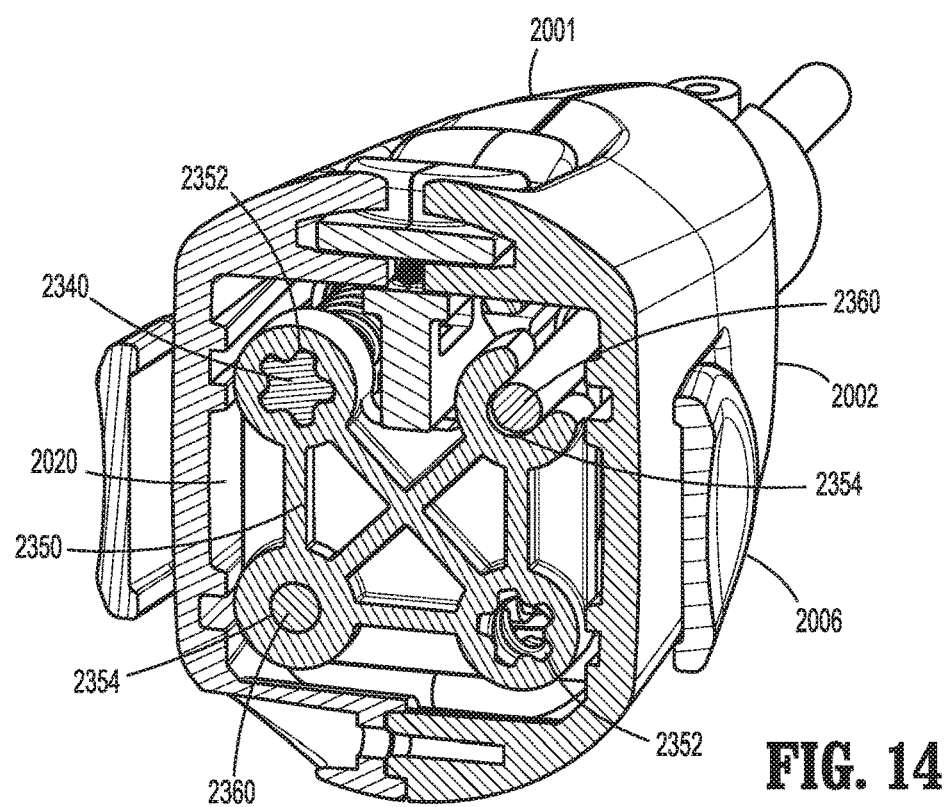
FIG. 14 is a perspective, cross-sectional view of the instrument drive assembly of FIG. 12 taken along the section line 14-14 of FIG. 13.
Figure 15:
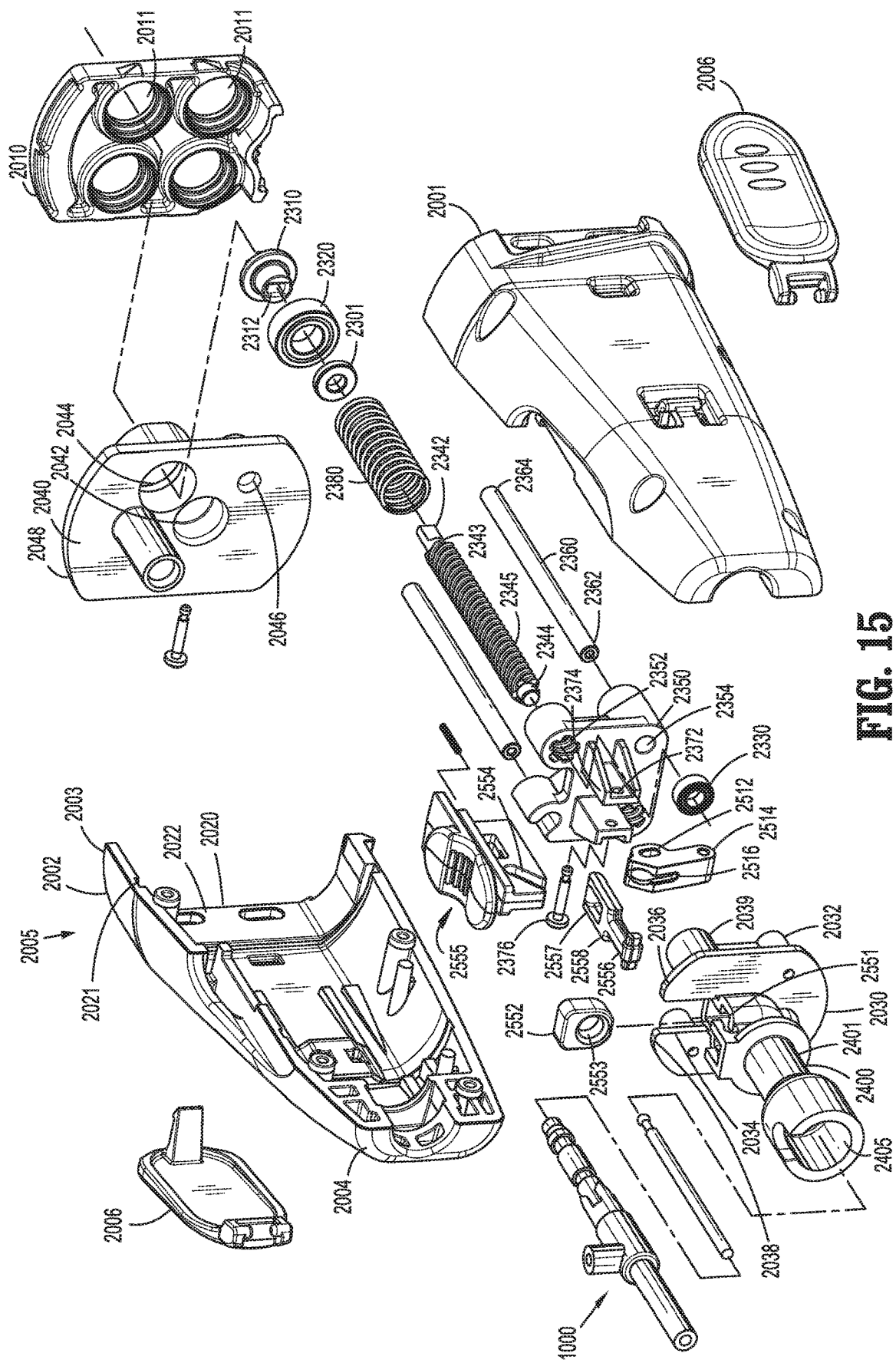
FIG. 15 is a parts separated view of the instrument drive assembly of FIG. 11.

With reference to FIGS. 11, 12 and 15, instrument drive assembly 2000 includes a housing assembly 2005 having a first side 2001 and a second side 2002, where first and second sides 2001, 2002 define a cavity 2020 therebetween. Housing assembly 2005 further includes a proximal end plate 2010 supported at a proximal end 2003 thereof, a distal end plate 2030 supported at a distal end 2004 thereof, a drive assembly 2300 supported in cavity 2020, an internal plate 2040 supported in cavity 2020, a coupling assembly 2500 disposed in cavity 2020, and a coupling tube 2400 supported by distal end plate 2030 and extending distally thereof. As best illustrated in FIG. 15, first and second sides 2001, 2002 of housing assembly 2005 act as two halves of a shell, with proximal end plate 2010 acting as a proximal wall and distal end plate 2030 acting as a distal wall. Housing assembly 2005 further includes a release mechanism 2006 disposed on first side 2001, second side 2002, and/or both first and second sides 2001, 2002. Release mechanism 2006 of housing assembly 2005 serves to provide a quick and easy means for coupling and uncoupling instrument drive assembly 2000 and instrument control unit 1000.

Proximal end plate 2010 of housing assembly 2005 defines at least one through-hole 2011 therein, and in an embodiment it is envisioned that proximal end plate 2010 may define four through-holes 2011 therein. Each through-hole 2011 is configured to receive a proximal gear 2310 of drive assembly 2300 therethrough, such that proximal gear 2310 may engage the instrument control gear of instrument control unit 100.

Figure 17:
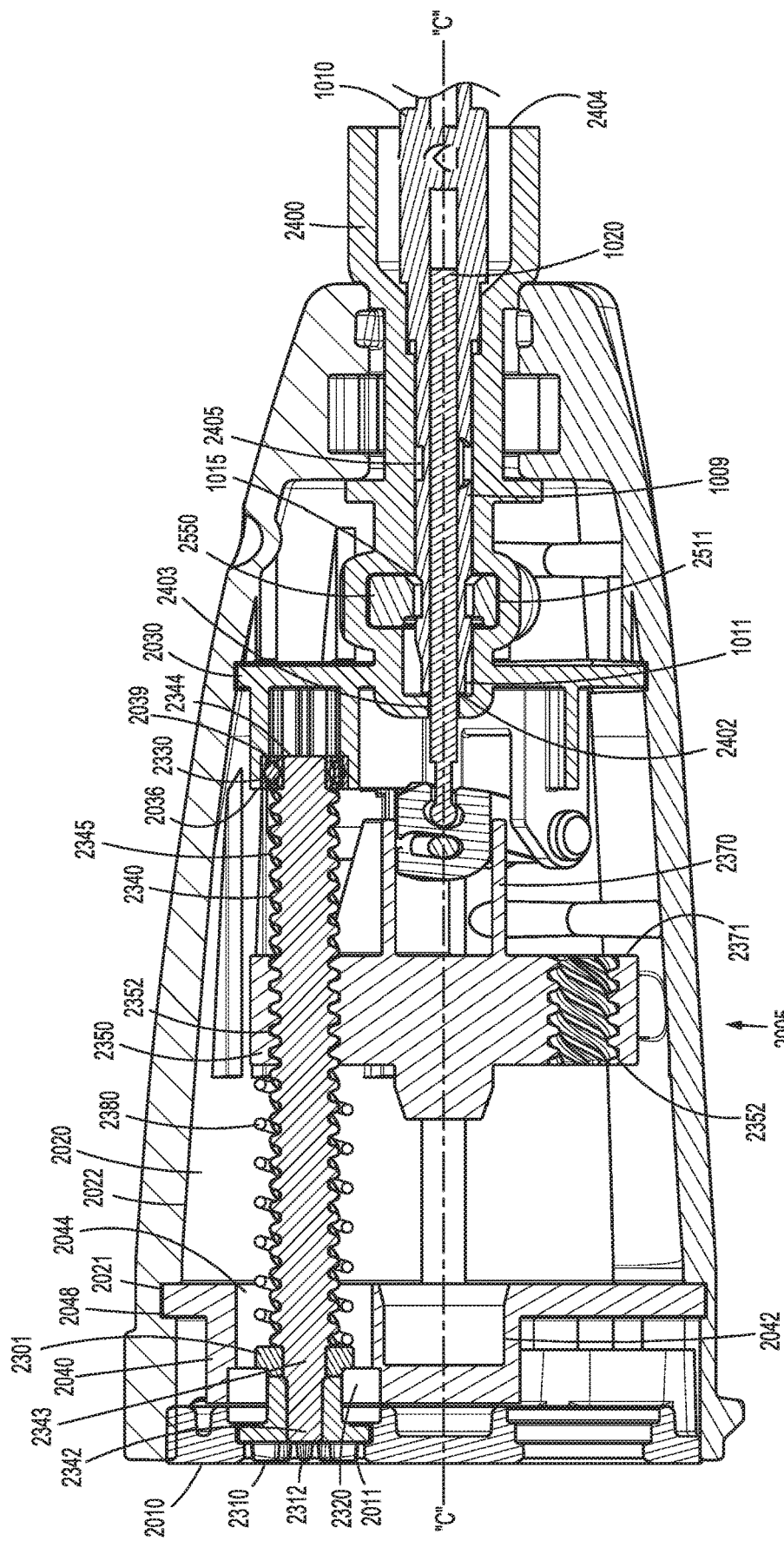
FIG. 17 is a side, cross-sectional view of the instrument drive assembly of FIG. 12 taken along the section line 17-17 of FIG. 13.

Distal end plate 2030 of housing assembly 2005 includes at least one rod receiving portion 2032 and at least one distal bearing cavity 2039, where the rod receiving portion 2032 and the distal bearing cavity 2039 are disposed on a proximal surface 2036 thereof. In an embodiment it is envisioned that distal end plate 2030 may include a pair of rod receiving portions 2032 laterally offset from each other. Distal end plate 2030 further defines an elongated cavity 2034, such that elongated cavity 2034 extends inward from an outer edge 2038 of distal end plate 2030 to align with a longitudinal axis "C" of housing assembly 2005 (FIGS. 11 and 17). It is envisioned that elongated cavity 2034 of distal end plate 2030 of housing assembly 2005 defines a generally "U" shaped cavity configured to support coupling tube 2400, such that coupling tube 2400 is supported therein and extends distally from cavity 2020 of housing assembly 2005, as described below.

Internal plate 2040 of housing assembly 2005 defines a first through-hole 2042 which is coaxial with the longitudinal axis "C" of housing assembly 2005, a second through-hole 2044 laterally offset from longitudinal axis "C" and which is coaxial with at least one through-hole 2011 of proximal end plate 2010, and at least one rod receiving portion 2046 laterally offset from longitudinal axis "C". A side edge 2048 of internal plate 2040 is supported in a channel 2021 defined in an inner surface 2022 of both first and second sides 2001, 2002 of housing assembly 2005, such that internal plate 2040 is fixed therein. It is envisioned that internal plate 2040 provides structural support for housing assembly 2005, and further provides support for drive assembly 2300, as discussed below.

Figure 16:
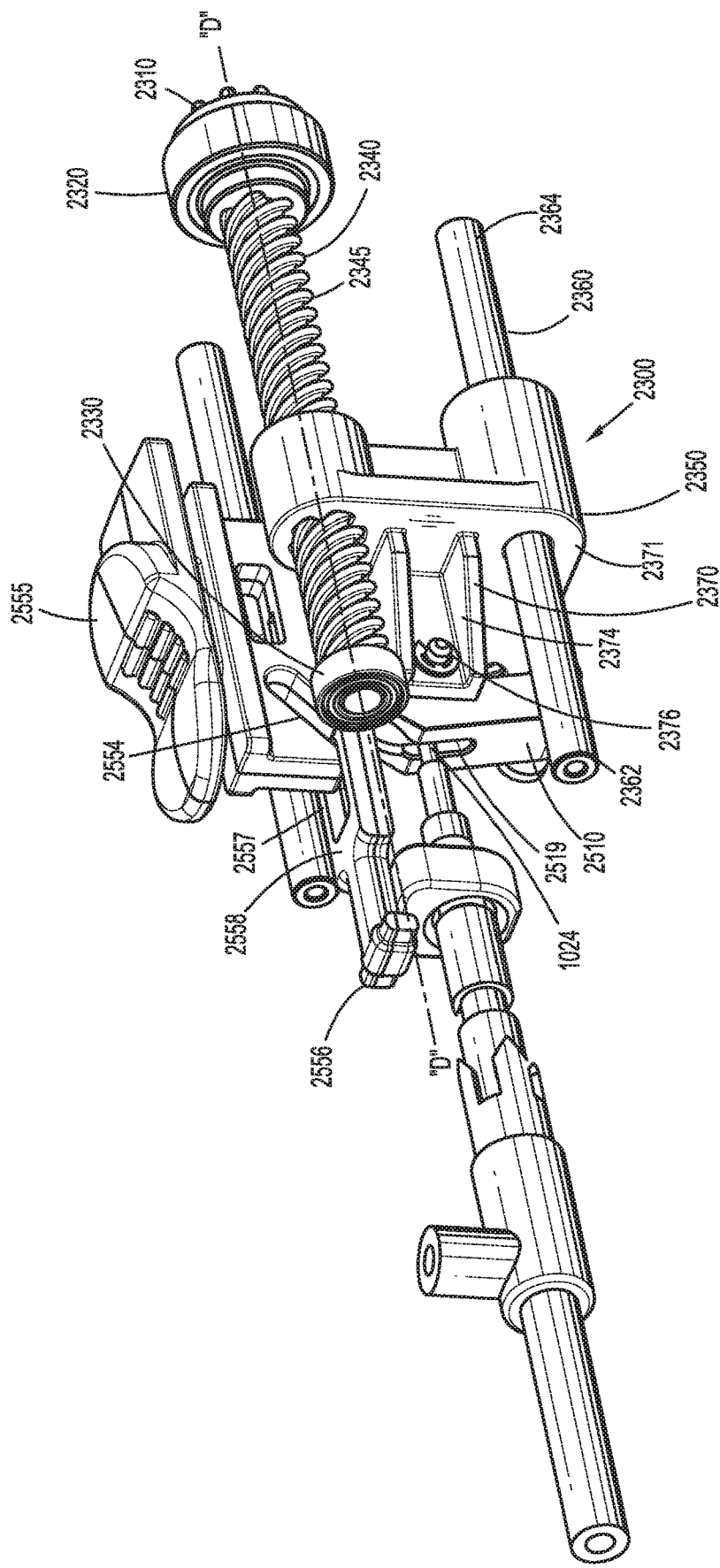
FIG. 16 is a front perspective view of the instrument drive assembly of FIG. 11 with various parts removed.

With reference to FIGS. 15-17, drive assembly 2300 of housing assembly 2005 will be further described. Drive assembly 2300 of housing assembly 2005 includes a proximal gear 2310, a proximal bearing 2320, a distal bearing 2330, a drive screw 2340, a drive plate 2350, and a guide rod 2360. Drive screw 2340 includes a proximal portion 2342, a proximal shaft 2343, a threaded portion 2345 and a distal shaft 2344, and defines a longitudinal axis "D" extending through a radial center thereof (FIG. 16). Proximal gear 2310 is configured to engage with the instrument control gear (e.g., crown gear "CG" of motor "M") of instrument control unit 100, such that rotation of crown gear "CG" causes a corresponding rotation of proximal gear 2310. Proximal gear 2310 may be a crown gear "CG" that is configured to mate with and/or mesh with crown gear "CG" of motor "M." Proximal gear 2310 includes an aperture 2312 extending longitudinally therethrough configured to mechanically engage proximal portion 2342 of drive screw 2340. As illustrated, aperture 2312 and proximal portion 2342 of drive screw 2340 have corresponding, non-circular cross-sections, such that proximal gear 2310 and drive screw 2340 are keyed to one another, which results in a rotationally fixed connection therebetween. Rotation of proximal gear 2310 causes drive screw 2340 to rotate about longitudinal axis "D" of drive screw 2340 in a corresponding direction and rate of rotation.

Drive plate 2350 of drive assembly 2300 includes at least one threaded aperture 2352 and at least one through-hole 2354 extending longitudinally therethrough. Threaded aperture 2352 is configured to mechanically engage threaded portion 2345 of drive screw 2340. That is, drive plate 2350 and drive screw 2340 of drive assembly 2300 are threadingly engaged with each other. Guide rod 2360 of drive assembly 2300 is slidably disposed in a through-hole 2354 of drive plate 2350, where a first end 2362 of guide rod 2360 is coupled to rod receiving portion 2032 of distal end plate 2030 and a second end 2364 of guide rod 2360 is coupled to rod receiving portion 2046 of internal plate 2040. It is envisioned that guide rod 2360 is laterally offset from, and parallel to, longitudinal axis "D" of drive screw 2340. It should be appreciated that housing assembly 2005 may include any number of guide rods 2360, where each guide rod 2360 is disposed in a respective rod receiving portion 2032 of proximal end plate 2030, a respective rod receiving portion 2046 of internal plate 2040, and a respective through-hole 2353 of drive plate 2350. In an embodiment, it is envisioned that housing assembly 2005 may include a pair of guide rods 2360, where guide rods 2360 are laterally offset from, and symmetrically spaced about, longitudinal axis "C" of housing assembly 2005. As such, guide rod 2360 inhibits or prevents drive plate 2350 from rotating about longitudinal axis "D" of drive screw 2340 as drive screw 2340 is rotated. Accordingly, drive plate 2350 is configured to be engaged with drive screw 2340 in a manner such that rotation of drive screw 2340 causes longitudinal translation of drive plate 2350. More specifically, rotation of proximal gear 2310 in a first direction (e.g., clockwise) causes drive screw 2340 to rotate in a corresponding first direction and drive plate 2350 to translate in a first longitudinal direction (e.g., proximally) with respect to proximal gear 2310, and rotation of proximal gear 2310 in a second direction (e.g., counter-clockwise) causes drive screw 2340 to rotate in a corresponding second direction and drive plate 2350 to translate in a second longitudinal direction (e.g., distally) with respect to proximal gear 2310.

Drive plate 2350 of drive assembly 2300 further includes a mounting bracket 2370 extending distally from a distal facing surface 2371 thereof. With brief reference to FIG. 15, mounting bracket 2370 of drive plate 2350 supports coupling assembly 2500 thereon. Coupling assembly 2500 is configured to mechanically engage instrument drive shaft 1020 of surgical instrument 1000, such that proximal and distal translation of drive plate 2350, with respect to proximal gear 2310, results in proximal and distal translation of instrument drive shaft 1020, as discussed in further detail below. Longitudinal translation of drive plate 2350 is configured to drive a function of the end effector of surgical instrument 1000 in a similar fashion as drive member 380 of instrument drive assembly 200, and thus will not be discussed in any further detail herein. Longitudinal translation of drive plate 2350 further directs locking and unlocking of coupling assembly 2500 with respect to instrument drive shaft 1020, as discussed below.

With drive assembly 2300 and housing assembly 2005 assembled, proximal bearing 2320 of drive assembly 2300 is supported in through-hole 2011 of internal plate 2040, and distal bearing 2330 of drive assembly 2300 is disposed in distal bearing cavity 2039 of distal end plate 2030 (FIG. 17). Each of proximal bearing 2320 and distal bearing 2330 facilitate rotation of drive screw 2340 with respect to housing assembly 2005, where internal plate 2040 and distal end plate 2030 may serve as proximal and distal stops, respectively, for drive plate 2350. Drive assembly 2300 may further include a washer or spacer 2301 disposed about proximal shaft 2343 of drive screw 2030, between proximal bearing 2320 of drive assembly 2300 and threaded portion 2345 of drive screw 2340 of drive assembly 2300. Washer 2301 further facilitates rotation of drive screw 2340. Drive assembly 2300 may further include a biasing element 2380 disposed about drive screw 2340 between washer 2301 and drive plate 2350. Biasing element 2380 serves as a return spring providing distal bias to drive plate 2340, as discussed below.

Referring to FIG. 17, housing assembly 2005 further includes coupling tube 2400. Coupling tube 2400 includes a proximal end 2402 defining a through-hole 2403, and a longitudinal bore or lumen 2405 extending distally therefrom. It is envisioned that longitudinal bore 2405 defines a larger diameter than through-hole 2403, such that longitudinal bore 2405 is configured to receive both instrument sleeve 1010 and instrument drive shaft 1020 of surgical instrument 1000 therein, and through-hole 2403 is configured to receive only instrument drive shaft 1020 therethrough, as discussed below. Coupling tube 2400 is supported in elongated cavity 2034 of distal end plate 2030 of housing assembly 2005 such that a distal portion 2401 of couple tube 2400 extends distally therefrom. It is envisioned that coupling tube 2400 may be monolithically formed with distal end plate 2030, or may alternatively be releasably couplable to elongated cavity 2034, such that coupling tube 2400 slides into and out of engagement with elongated cavity 2030. Longitudinal bore 2405 and through-hole 2403 of coupling tube 2400 define a longitudinal axis "T" of coupling tube 2400 (FIG. 18A), which may be coaxial with longitudinal axis "C" of housing assembly 2005. Longitudinal bore 2405 is configured to slidingly receive a proximal portion 1009 of instrument sleeve 1010. It is envisioned that during coupling of surgical instrument 1000 with instrument drive assembly 2000, coupling tube 2400 may aid alignment of instrument drive shaft 1020 and drive assembly 2300. More specifically, instrument sleeve 1010 of surgical instrument 1000 is slidably inserted into a distal opening 2404 of coupling tube 2400 of housing assembly 2005 of instrument drive assembly 2000. When instrument sleeve 1010 of surgical instrument 1000 is fully inserted into longitudinal bore 2405 of coupling tube 2400, a proximal end 1011 of instrument sleeve 1010 abuts a distally facing surface of proximal end 2402 of coupling tube 2400.

Housing assembly 2005 further includes a retention mechanism 2550 configured to releasably retain or secure instrument sleeve 1010 of surgical instrument 1000 to coupling tube 2400, and thus to housing assembly 2005. With reference to FIGS. 15, 16, and 18A-19D, retention mechanism 2550 includes a lock plate 2552, a button 2555, and a release arm 2558. Coupling tube 2400 of housing assembly 2005 defines a locking cavity 2551 disposed along a length thereof, such that lock plate 2552 is slidably insertable therein. Lock plate 2552 defines a through-hole 2553 configured to slidingly receive instrument sleeve 1010 therethrough, and is transitionable between a locked and unlocked configuration, with respect to instrument sleeve 1010, as discussed below. More specifically, in the locked configuration through-hole 2553 of lock plate 2552 is off-axis of, and offset or angled from, the longitudinal axis "T" of coupling tube 2400, and in the unlocked configuration through-hole 2553 of lock plate 2552 is coaxial with the longitudinal axis "T" of coupling tube 2400.

Release arm 2558 of retention mechanism 2550 defines an engagement region 2557 configured to engage a portion of button 2555, and an abutment region 2556, configured to abut lock plate 2552. Button 2555 is slidably coupled to housing assembly 2005, and actuatable between first and second positions. As button 2555 translates proximally, with respect to housing assembly 2005, button 2555 slides from the first position to the second position, such that the engagement region 2557 of release arm 2558 ride along a cam slot 2554 of button 2555. Cam slot 2554 of button 2555 has a first end 2554a and a second end 2554b, wherein when button 2555 is in the first position the engagement region 2557 of release arm 2558 is disposed at the first end 2554a of cam slot 2554 and the abutment region 2556 of release arm 2558 is spaced away from lock plate 2552. When button 2555 is in the second position the engagement region 2557 of release arm 2558 is disposed at the second end 2554b of cam slot 2554 and abutment region 2556 of release arm 2558 is in abutment with lock plate 2552. Accordingly, as engagement region 2557 cams along cam slot 2554, abutment region 2556 of release arm 2558 comes into and out of abutment with lock plate 2552, thus transitioning lock plate 2552 between the locked and unlocked configurations, respectively.

It is envisioned that the transition of button 2555 from the first position to the second position may correspond to the transitioning of lock plate 2552 into the unlocked configuration. It is contemplated that retention mechanism 2550 may further include a biasing member 2559 disposed in locking cavity 2551, such that lock plate 2552 is biased to the locked configuration. It is further contemplated that button 2555 may include a biasing member (not shown) supported thereon such that button 2555 is biased to the first position.

Figure 18C:
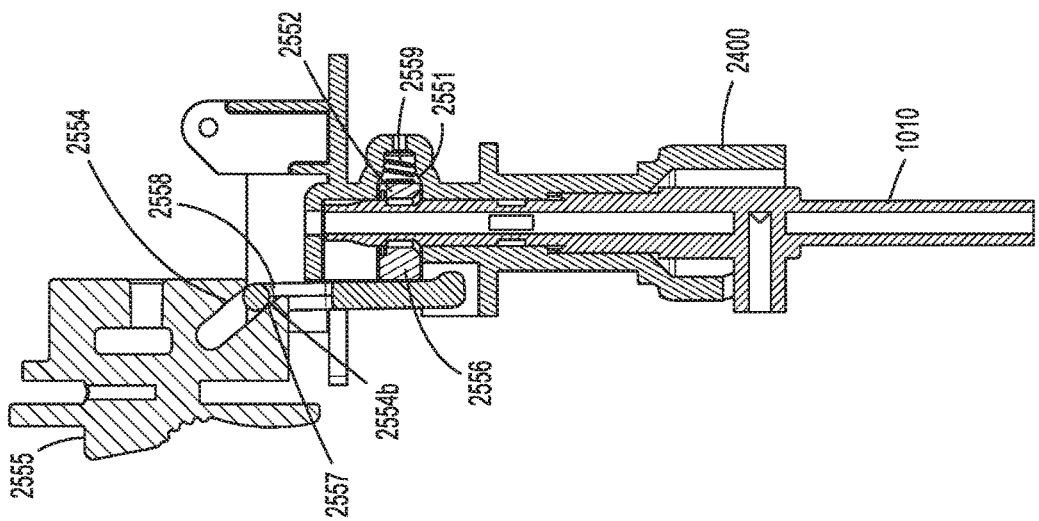

With continued reference to FIGS. 18A-19D, coupling and uncoupling of instrument sleeve 1010 of surgical instrument 1000 to retention mechanism 2550 of instrument drive assembly 2000 will be discussed. During coupling of instrument sleeve 1010 to retention mechanism 2550, instrument sleeve 1010 is inserted into distal opening 2404 of coupling tube and slid proximally therein (FIG. 18A). As the proximal end 1011 of instrument sleeve 1010 approaches the proximal end 2402 of coupling tube 2400, the proximal end 1011 of instrument sleeve 1010 urges lock plate 2551 to transition into the unlocked configuration (e.g., through-hole 2553 is coaxial with longitudinal axis "T" of coupling tube 2400) (FIG. 18B). As instrument sleeve 1010 continues to slide proximally, lock plate 2552 aligns with recess 1015 of instrument sleeve 1010, such that lock plate 2552 is permitted to transition into the locked configuration (e.g., through-hole 2553 is offset or angled from longitudinal axis "T" of coupling tube 2400) (FIG. 18C). With lock plate 2551 engaged within recess 1015 of instrument sleeve 1010, longitudinal translation of instrument sleeve 1010, within coupling tube 2400, is inhibited.

Figure 19A:
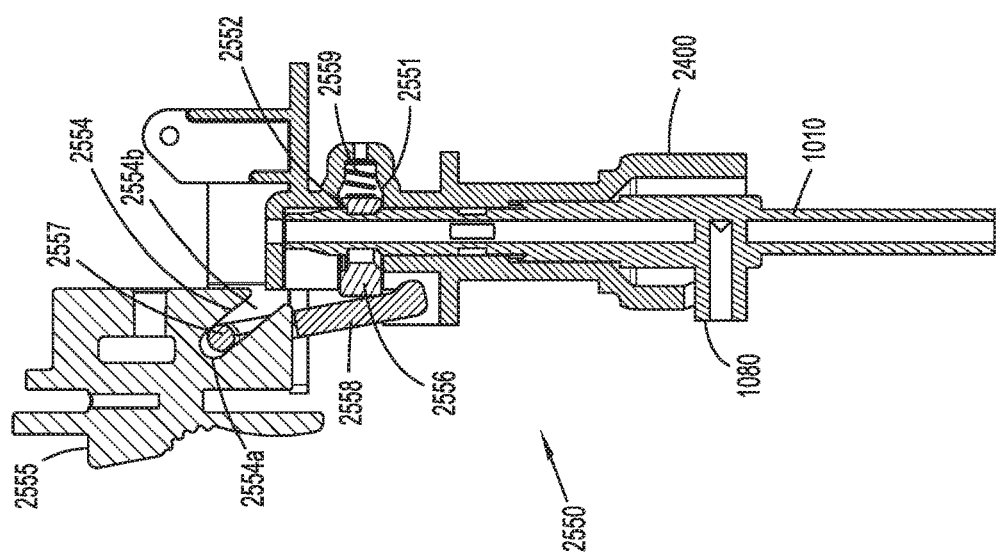
FIGS. 19A-19D are side views of the retention mechanism of FIGS. 18A-C in various states of actuation during removal of the instrument sleeve therefrom.
Figure 19B:
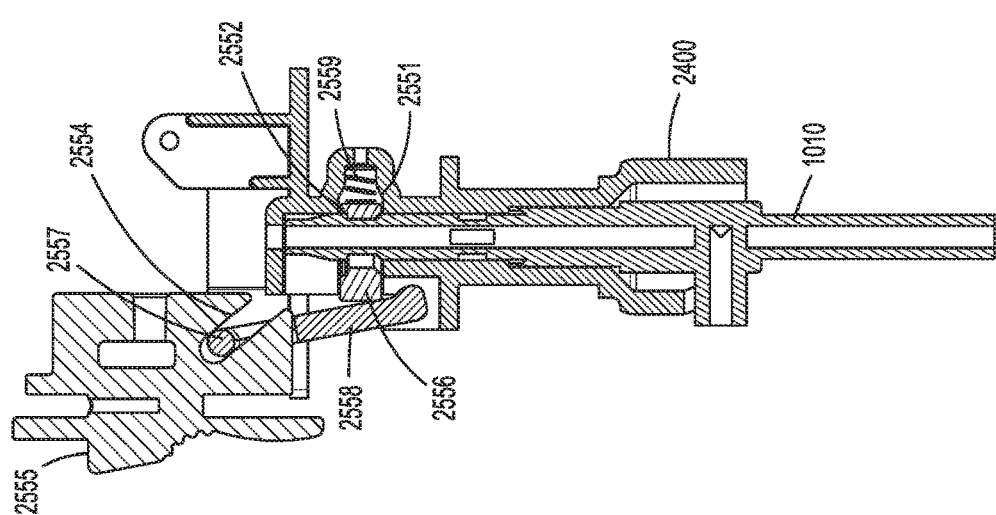
Figure 19C:
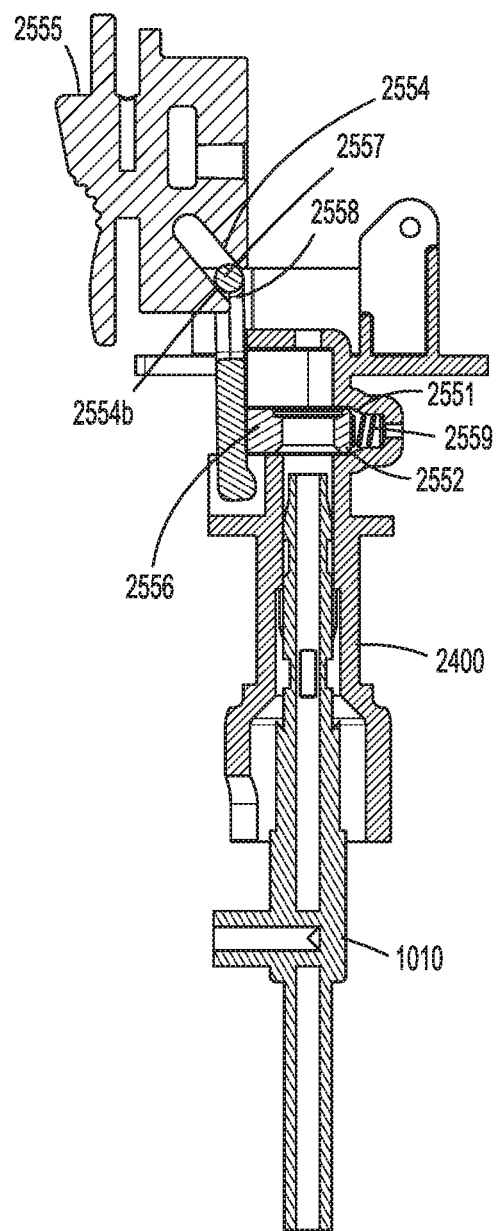
Figure 19D:
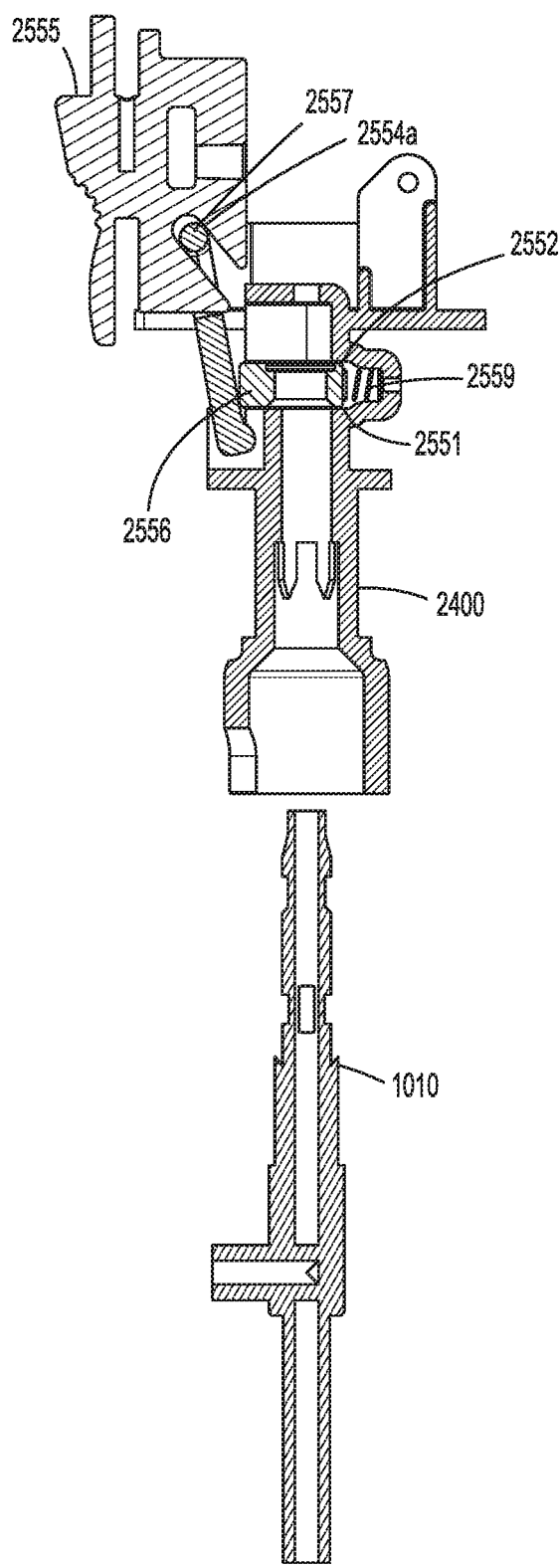

During uncoupling of instrument sleeve 1010 of surgical instrument 1000 from retention mechanism 2550 of instrument drive assembly 2000, button 2555 is transitioned into the second position, such that engagement region 2557 of release arm 2558 cams along cam slot 2554 of button 2555 into the second end 2554b of cam slot 2554 (FIGS. 19A and 19B). With engagement region 2557 at the second end 2554b of cam slot 2554, abutment region 2556 of release arm 2558 is brought into abutment with lock plate 2552, urging lock plate 2551 into the unlocked configuration (e.g., through-hole 2553 is coaxial with longitudinal axis "T" of coupling tube 2400) (FIG. 19B). With lock plate 2551 in the unlocked configuration, lock plate 2551 is disengaged from recess 1015 of instrument sleeve 1010, such that instrument sleeve 1010 is free to be withdrawn from and uncoupled from coupling tube 2400 (FIGS. 19C and 19D).

With reference to FIGS. 15 and 16, coupling assembly 2500 of instrument drive assembly 2000 will be discussed. Coupling assembly 2500 is disposed in cavity 2020 of housing assembly 2005 and supported by drive plate 2350. Coupling assembly 2500 serves to releasably couple instrument drive shaft 1020 of surgical instrument 1000 to drive assembly 2300 of housing assembly 2005. Coupling assembly 2500 engages with mounting bracket 2370 of drive plate 2350, which as noted above, extends distally from the distal facing surface 2371 of drive plate 2350.

Mounting bracket 2370 of drive plate 2350 is configured to pivotably support a drive link 2510 thereon, where drive link 2510 is configured to engage with, and couple to, instrument drive shaft 1020 of surgical instrument 1000, as discussed below. Mounting bracket 2370 includes a pair of receiving arms 2374, where receiving arms 2374 are spaced apart from one another and define a receiving nook or through-hole 2372 therein, where through-hole 2372 of each receiving arm 2374 is aligned such that a first pin 2376 may be disposed therein. Drive link 2510 is configured to be received between receiving arms 2374 of mounting bracket 2370, and is pivotably couple thereto via first pin 2376. First pin 2376 passed through each through-hole 2372 of receiving arms 2374 and a cam slot 2512 of drive link 2510. It is envisioned that drive link 2510 may alternatively be coupled to mounting bracket 2370 via a pair of extrusions or bosses extending from alternate sides of drive link 2510.

Drive link 2510 of coupling assembly 2500 further defines a through-hole 2514 therein, such that a second pin 2378 couples drive link 2510 to a through-hole 2407 disposed on a proximal portion 2408 of coupling tube 2400. It is envisioned that through-hole 2407 of coupling tube 2400 may be transverse to longitudinal axis "C" of housing assembly 2005. As such, when coupled, drive link 2510 is pivotably coupled to coupling tube 2400 between a locked position and an unlocked position, with respect to instrument drive shaft 1020 of surgical instrument 1000. More specifically, as drive plate 2350 of drive assembly 2300 translates proximally or distally, as discussed above, first pin 2376 rides along cam slot 2512 of drive link 2510 directing drive link 2510 to pivot about second pin 2378.

With reference to FIGS. 21A and 21B, drive link 2510 of coupling assembly 2500 further defines a receiving region 2516 disposed on a distal facing surface thereof, which is configured to releasably retain and secure coupling ball 1022 of instrument drive shaft 1020. Receiving region 2516 of drive link 2510 defines a cavity 2517 therein, a port 2518 extending into cavity 2517, and a channel 2519 extending along cavity 2517. Receiving region 2516 of drive link 2510 acts as a socket joint for coupling ball 1022 of instrument drive shaft 1020, where coupling ball 1022 can only enter and exit cavity 2517 through port 2518. Through pivoting of drive link 2510 between the unlocked and locked positions, port 2518 is correspondingly oriented to be aligned with, or brought off axis of, or angled from, longitudinal axis "T" of coupling tube 2400, respectively. More specifically, with drive link 2510 in the unlocked position, port 2518 is aligned with longitudinal axis "T", such that coupling ball 1022 of instrument drive shaft 1020 may be received therein. Once drive link 2510 is pivoted to the locked position, port 2518 is brought off-axis of, or angled from, longitudinal axis "T" of coupling tube 2400, and coupling ball 1022 of instrument drive shaft 1020 is captured within cavity 2517. In the locked position, neck 1024 of instrument shaft 1020 resides in channel 2519 of receiving region 2516 of drive link 2510, where channel 2519 is configured to be smaller than a diameter of coupling ball 1022, thus locking coupling ball 1022 in cavity 2517 of receiving region 2516 of drive link 2510. As such, port 2518 of receiving region 2516 of drive link 2510 is configured to receive coupling ball 1022 of instrument drive shaft 1020 therethrough, while channel 2519 of receiving region 2516 of drive link 2510 is configured to inhibit coupling ball 1022 from leaving cavity 2517. With reference to FIGS. 21A and 21B, coupling ball 1022 (shown in phantom) is disposed in cavity 2517 of receiving region 2516 and neck 1024 is disposed in channel 2519.

Figure 20C:
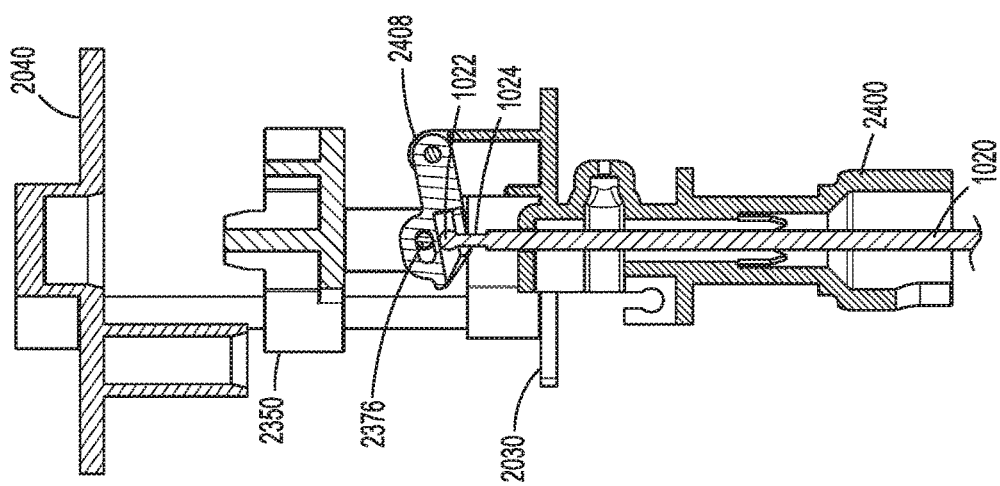
FIGS. 20A-20C are side views of a coupling assembly of the instrument drive assembly of FIG. 11 in various states of actuation during coupling of an instrument drive shaft therewith.
Figure 20B:
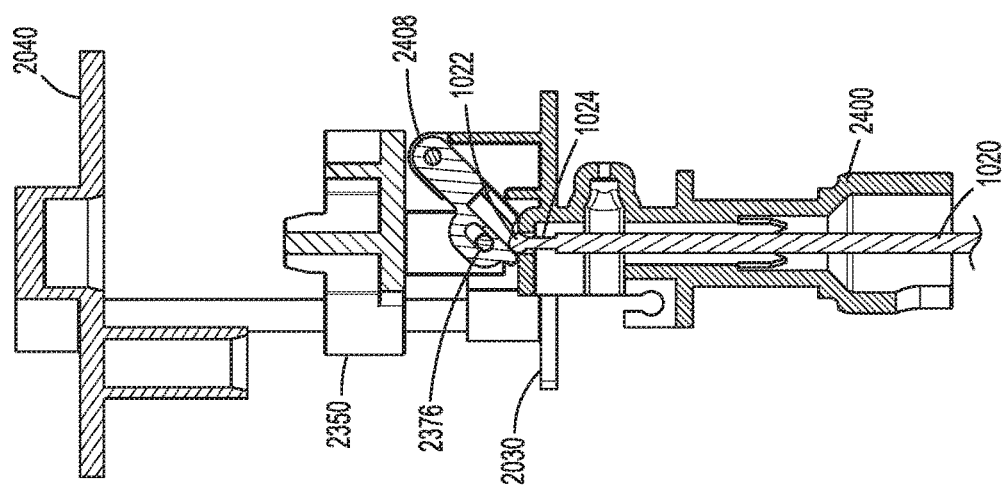
Figure 20A:
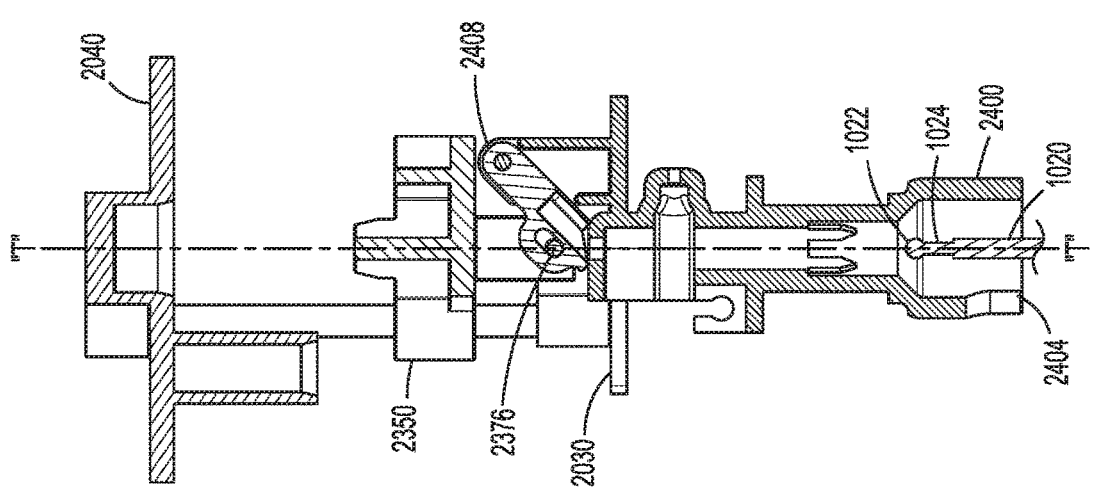
Figure 22:
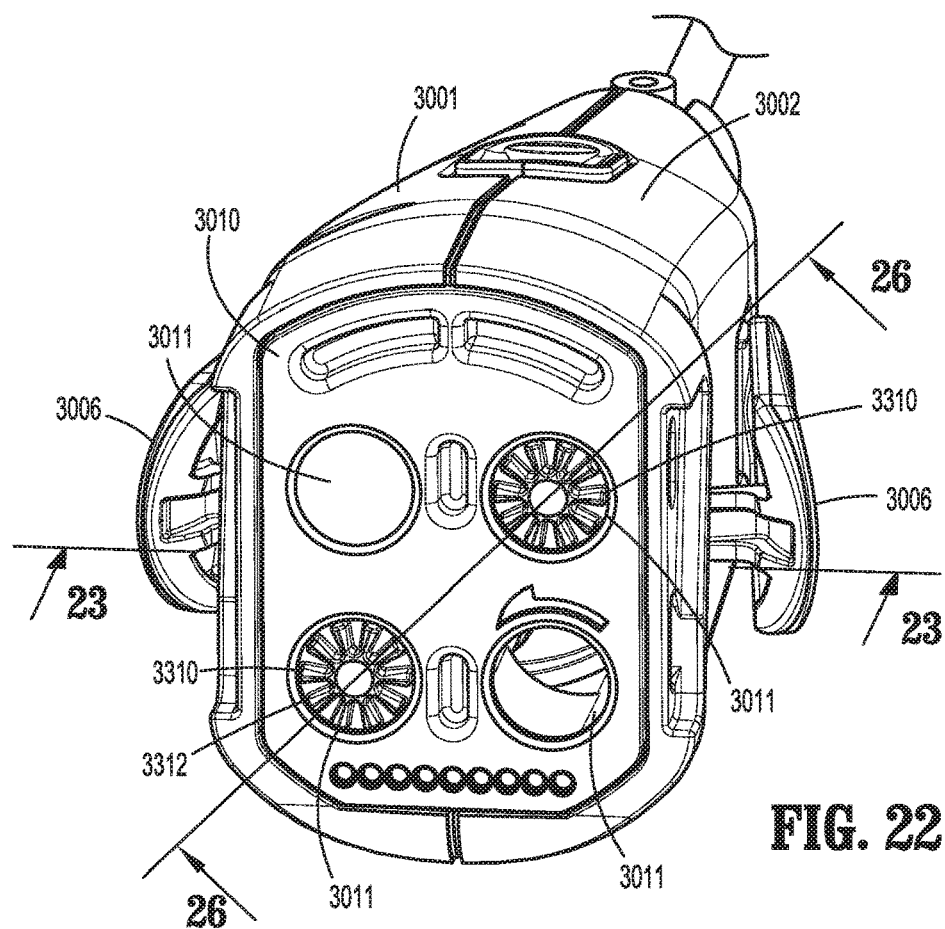
FIG. 22 is a rear perspective view of an instrument drive assembly in accordance with another embodiment of the present disclosure.
Figure 23:
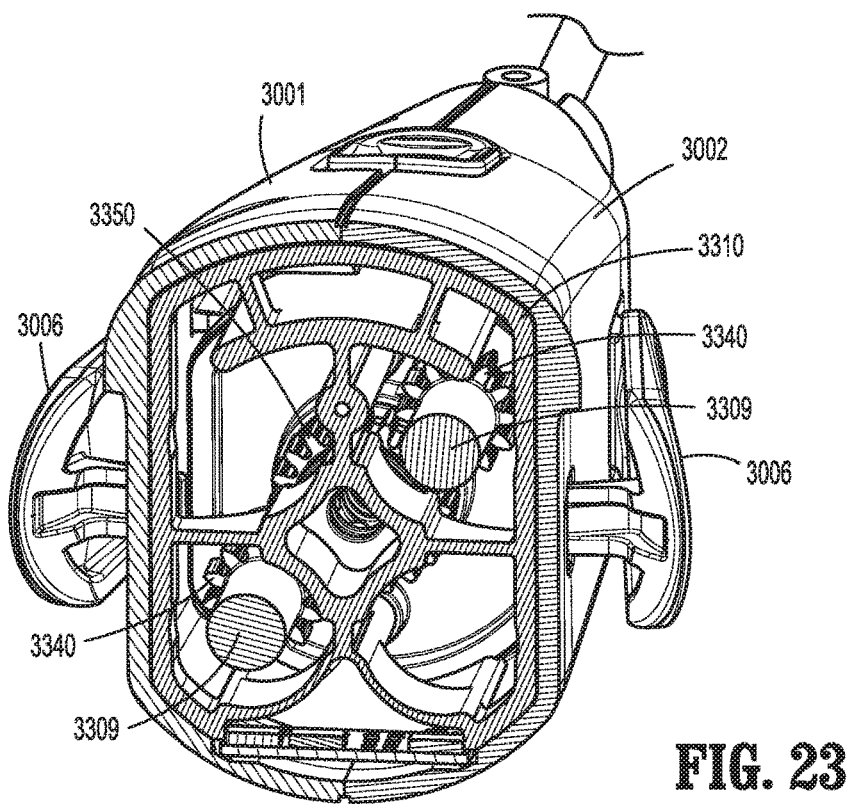
FIG. 23 is a perspective, cross-sectional view of the instrument drive assembly of FIG. 22 taken along the section line 23-23 of FIG. 22.

With reference to FIGS. 20A-20C, the engagement of instrument drive shaft 1020 of surgical instrument 1000 to coupling assembly 2500 of instrument drive assembly 2000 will be discussed. As discussed above, proximal and distal translation of drive plate 2350 of drive assembly 2300 pivots drive link 2510 between the unlocked position and the locked position, such that coupling assembly 2500 transitions between the unlocked and locked configuration, respectively. With drive plate 2350 in a distal most position, coupling assembly 2500 is in the unlocked configuration, drive link 2510 is in the unlocked position, such that port 2518 of drive link 2510 is aligned with longitudinal axis "T" of coupling tube 2400 (FIG. 20A). With port 2518 aligned with longitudinal axis "T", instrument drive shaft 1020 is inserted into the distal end 2404 of coupling tube 2400 and translated proximally, such that coupling ball 1022 of instrument drive shaft 1020 is brought into approximation with port 2518 of receiving region 2516 of drive link 2510. As instrument drive shaft 1020 translates proximally, coupling ball 1022 is inserted through port 2518 and brought into cavity 2517 of retention region 2516 of drive link 2510 (FIG. 20B). With coupling ball 1022 residing in cavity 2517, drive plate 2350 is translated proximally. As drive plate 2350 is translated proximally, first pin 2376 rides along cam slot 3512 of drive link 2510, such that drive link 2510 pivots about second pin 2378 into the locked position. With drive link 2510 in the locked position, neck 1024 of instrument shaft 1020 is disposed in channel 2519 of drive link 2510, thus capturing coupling ball 1022 within cavity 2517 of receiving region 2516 of drive link 2510 (FIG. 20C). Further, in the locked position, port 2518 of receiving region 2516 of drive link 2510 is brought off axis of, or angled from, the longitudinal axis "T" of coupling tube 2400. With drive link 2510 pivoted into the locked position, coupling assembly 2500 is thus in the locked configuration, with respect to instrument drive shaft 1020. Further proximal movement of drive plate 2350 causes drive link 2510 to pivot past the locked position directing proximal translation of instrument drive shaft 1020. Accordingly, proximal translation of drive plate 2350 causes drive plate 2510 to pivot past the locked position, thus directing proximal translation of instrument drive shaft 1020, which actuates the end effector (not shown) disposed at the distal end of instrument drive shaft 1020.

With reference to FIGS. 19A-20C, a complete coupling and decoupling of instrument drive assembly 2000 to surgical instrument 1000 will be briefly discussed. Initially, instrument sleeve 1010 of surgical instrument 1000 is inserted into coupling tube 2400 of housing assembly 2005 and translated proximally until lock plate 2552 of retention mechanism 2550 is brought into engagement with recess 1015 of instrument sleeve 1010, thus inhibiting any further translation of instrument sleeve 1010. It should be appreciated that coupling of instrument sleeve 1010 and retention mechanism 2550 may be performed with button 2555 of retention mechanism in either the first or second position. Next, drive plate 2350 of drive assembly 2300 is translated into a distal most position, such that drive link 2510 is pivoted into the unlocked position. Instrument drive shaft 1020 is then inserted proximally through instrument sleeve 1010 until coupling ball 1022 is engaged with drive link 2510. It is envisioned that instrument sleeve 1010 may alternatively be omitted, and thus instrument drive shaft 1020 may be inserted directly through coupling tube 2400. Once coupling ball 1022 is disposed in receiving region 2516 of drive link 2510, drive plate 2350 is translated proximally, such that drive link 2510 is pivoted into the locked position, and coupling assembly 2500 is translated into the locked configuration. Once instrument drive shaft 1020 is coupling with drive plate 2350, via drive link 2510, further proximal translation of drive plate 2350 directs actuation, articulation, or firing of the end effector of surgical instrument 1000.

During decoupling, drive plate 2350 of drive assembly 2300 is returned to the distal most position, such that drive link 2510 pivots to the unlocked position, and coupling assembly 2500 translates into the unlocked configuration. Instrument drive shaft 1020 of surgical instrument 1000 may now by translated distally, such that coupling ball 1022 is brought out of, or withdrawn from, receiving region 2516 of drive link 2510, and decoupled from instrument drive assembly 2000. Button 2555 of retention mechanism 2550 may then be translated into the second position, such that release arm 2558 abuts lock plate 2552, thus urging lock plate 2552 out of engagement with recess 1015 of instrument sleeve 1010 of surgical instrument 1000. Instrument sleeve 1010 may now be translated distally and withdrawn from coupling tube 2400. It is envisioned that outer sleeve 1010 and instrument drive shaft 1020 may be configured to be coupled, and uncoupled, independently and/or in any order.

During use of instrument drive assembly 2000, it should be appreciated that rotation of proximal gear 2310 of drive assembly 2300 in a first direction (e.g., clockwise) causes drive screw 2340 to rotate in a corresponding first direction, drive plate 2350 to translate in a first longitudinal direction (proximally), and drive link 2510 to pivot (towards the locked position as illustrated in FIG. 20C). Further translation of drive plate 2350 in the first longitudinal direction causes drive link 2510 to continue to pivot, past the locked position, such that instrument drive shaft 1020 is translated in the first longitudinal direction. Similarly, rotation of proximal gear 2310 of drive assembly 2300 in a second direction (e.g., counter-clockwise) causes drive screw 2340 to rotate in a corresponding second direction, drive plate 2350 to translate in a second longitudinal direction (distally), and drive link 2510 to pivot (towards the unlocked position as illustrated in FIG. 20B). As drive link 2510 pivots from a position past the locked position towards the locked position, instrument drive shaft 1020 is driven in the second longitudinal direction. Further translation of drive plate 2350 in the second longitudinal causes drive link 2510 to pivot into the unlocked position, such that instrument drive shaft 1020 may be decoupled therefrom.

With reference to FIGS. 22-31B, another embodiment of an instrument drive assembly in accordance with the present disclosure will be described with reference to instrument drive assembly 3000. Engagement and driving of instrument drive assembly 3000 and medical work station 1 are similar to that of instrument drive assembly 2000, and thus only difference and distinctions of instrument drive assembly 3000 will be discussed herein below. It should be appreciated that instrument sleeve 1010 and instrument drive shaft 1020 of surgical instrument 1000 may also be releasably coupled with instrument drive assembly 3000.

With reference to FIGS. 22-26, instrument drive assembly 3000 includes a housing assembly 3005 having a first side 3001 and a second side 3002, where first and second sides 3001, 3002 define a cavity 3020 therebetween. Housing assembly 3005 further includes a proximal end plate 3010 supported at a proximal end 3003 thereof, a distal end plate 3030 supported at a distal end 3004 of housing assembly 3005, a drive assembly 3300 (FIG. 25) supported in cavity 3020, an internal plate 3040 supported in cavity 3020, a retention mechanism 3550 disposed in cavity 3020, a coupling tube 3400 supported by distal end plate 3030, and a coupling assembly 3500 (FIGS. 30A-31B) disposed in cavity 3020. Housing assembly 3005 further includes a release mechanism 3006 disposed on first side 3001, second side 3002, and/or both first and second sides 3001, 3002. In a similar fashion as housing assembly 2005 of instrument drive assembly 2000, release mechanism 3006 of housing assembly 3005 serves to provide a quick and easy means for decoupling instrument drive assembly 3000 from instrument control unit 100.

Proximal end plate 3010 of housing assembly 3005 defines at least one through-hole 3011 therethrough, and in an embodiment it is envisioned that proximal end plate 3010 may define four through-holes 3011 therethrough. Each through-hole 3011 is configured to receive a proximal gear 3310 of drive assembly 3300 therethrough, such that proximal gear 3310 may engage the instrument control gear of instrument control unit 100.

Figure 26:
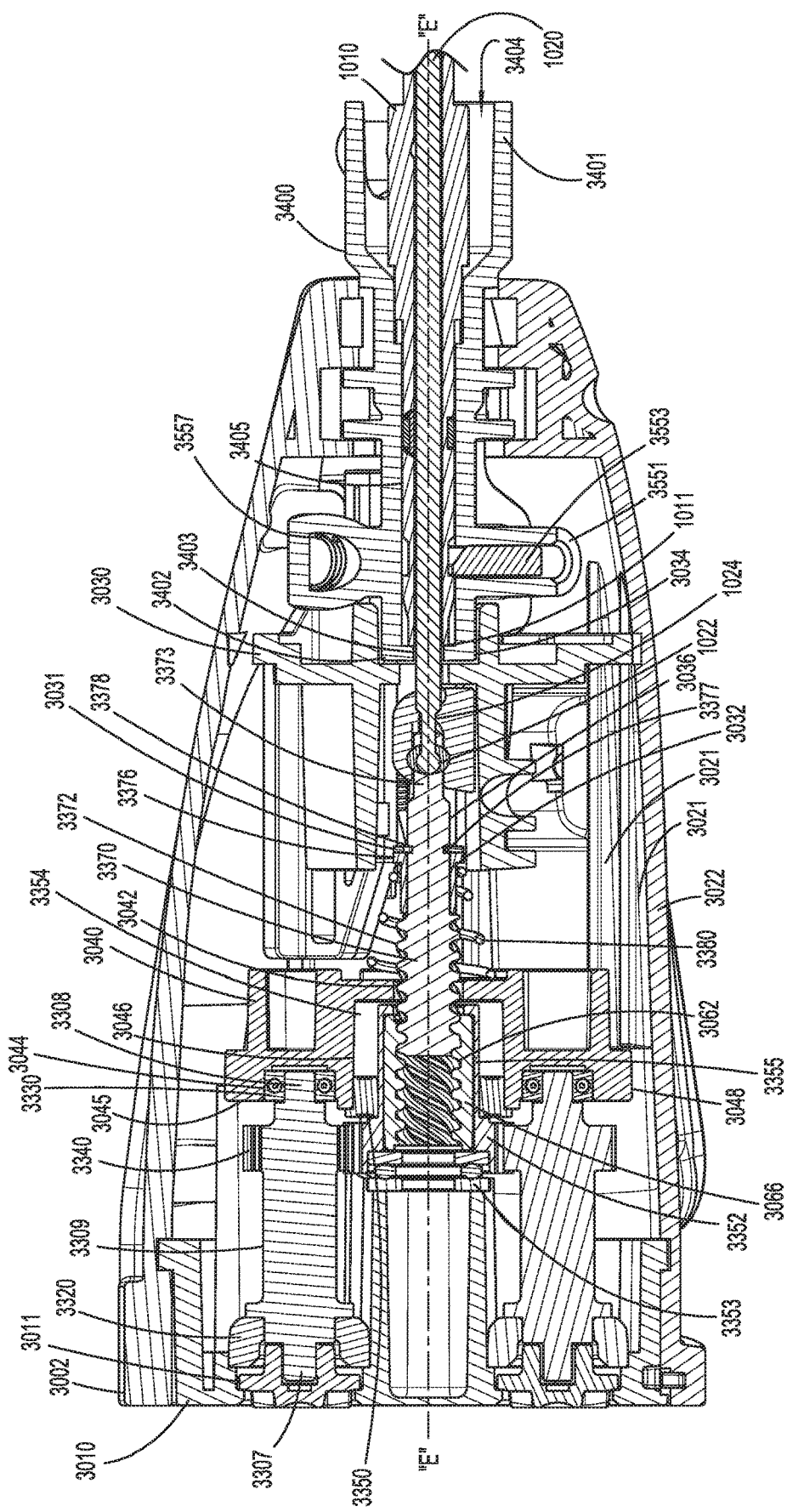
FIG. 26 is a side, cross-sectional view of the instrument drive assembly of FIG. 22 taken along the section line 26-26 of FIG. 22.

Distal end plate 3030 of housing assembly 3005 defines an elongated cavity 3034, such that elongated cavity 3034 extends inward from an outer edge 3038 of distal end plate 3030 to align with a longitudinal axis "E" of housing assembly 3005 (FIG. 26). It is envisioned that elongated cavity 3034 of distal end plate 3030 of housing assembly 3005 defines a generally "U" shaped cavity or profile configured to support coupling tube 3400, such that coupling tube 3400 is supported therein and extends distally from cavity 3020 of housing assembly 3005.

Internal plate 3040 of housing assembly 3005 defines a central through-hole 3042 which is coaxial with the longitudinal axis "E" of housing assembly 3005, at least one bearing cavity 3044 (FIG. 26) laterally offset from longitudinal axis "E" and which is coaxial with a respective through-hole 3011 of proximal end plate 3010, and a central cavity 3046 disposed along a proximal surface 3045 of internal plate 3040 which is coaxial with central through-hole 3042 and defines a larger diameter with respect to central through-hole 3042. A side edge 3048 of internal plate 3040 is supported within first and second sides 3001, 3002 of housing assembly 3005 and engages at least one stop member 3021 extending from an inner surface 3022 of both first and second sides 3001, 3002 of housing assembly 2005, such that internal plate 3040 is captured within housing assembly 3005 and linearly fixed therein. It is envisioned that internal plate 3040 provides structural support for housing assembly 3005, and further provides support for drive assembly 3300.

With reference to FIGS. 22-26, drive assembly 3300 includes an engagement assembly 3302 and a transfer assembly 3304. As illustrated, drive assembly 3300 includes two engagement assemblies 3302, however, any number engagement assemblies 3302 are envisioned herein. Each engagement assembly 3302 includes a coupling rod 3309, a proximal gear 3310, a proximal bearing 3320, a distal bearing 3330, and a distal gear 3340 disposed between proximal bearing 3320 and distal bearing 3330.

Figure 25:
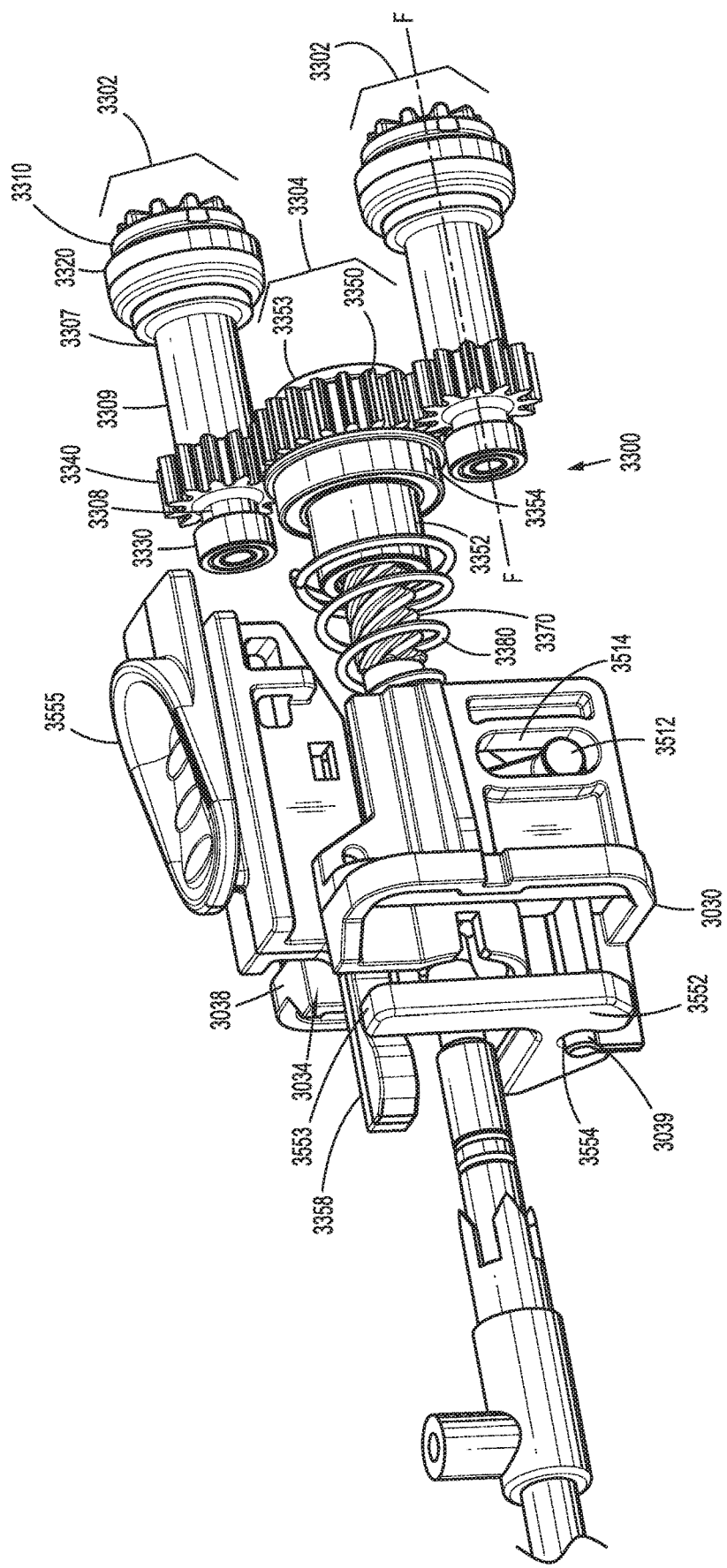
FIG. 25 is a front perspective view of the instrument drive assembly of FIG. 22 with various parts removed.

Coupling rod 3309 includes a proximal portion 3307 and a distal portion 3308, and defines a longitudinal axis "F" extending through a radial center thereof (FIG. 25). Proximal gear 3310 is configured to engage with the instrument control gear (e.g., crown gear "CG" of motor "M") of instrument control unit 100, such that rotation of crown gear "CG" causes a corresponding rotation of proximal gear 3310. Proximal gear 3310 may be a crown gear "CG" that is configured to mate with and/or mesh with crown gear "CG" of motor "M." Proximal gear 3310 includes an aperture 3312 extending longitudinally therethrough configured to mechanically engage proximal portion 3307 of coupling rod 3309. As illustrated, aperture 3312 and proximal portion 3307 of coupling rod 3309 have corresponding, non-circular cross-sections, such that proximal gear 3310 and coupling rod 3309 are keyed to one another, which results in a rotationally fixed connection therebetween. Rotation of proximal gear 3310 causes coupling rod 3309 to rotate about longitudinal axis "F" of coupling rod 3309 in a corresponding direction and rate of rotation. Distal gear 3340 is coupled to distal portion 3308 of coupling rod 3309 and may be keyed, or otherwise rotationally fixed with respect to coupling rod 3309 in a similar manner as proximal bearing 3310, such that rotation of coupling rod 3309, via rotation of proximal gear 3310, directs distal gear 3340 to rotate in a corresponding direction and rate of rotation. Alternatively, distal gear 3340 may be monolithically formed with coupling rod 3309, such that coupling rod 3309 extends proximally therefrom.

Transfer assembly 3304 of drive assembly 3300 includes a central gear 3350, a stem 3352 extending distally from central gear 3350, a proximal bearing 3353, and a distal bearing 3354. Stem 3352 defines a recess 3355 therein which extends proximally from a distal end 3351 of stem 3352. Central gear 3350 is positioned between internal plate 3040 and proximal end plate 3010. Proximal bearing 3353 is interposed between central gear 3350 and proximal end plate 3010, and distal bearing 3354 is positioned about stem 3352 and interposed between stem 3352 of central gear 3350 and central cavity 3046 of internal plate 3040. As such, central gear 3350 is longitudinally fixed within housing assembly 3005, rotatable about longitudinal axis "E" (FIG. 26) of housing assembly 3005, and is laterally offset from longitudinal axis "F" (FIG. 25) of engagement assembly 3302 defined by coupling rod 3309. Central gear 3350 is configured to engage and mesh with distal gear 3340 of engagement assembly 3302, such that rotation of distal gear 3040, via rotation of proximal gear 3310, corresponds to a rotation of central gear 3350. It should be appreciated that stem 3352 and central gear 3350 may be rotationally fixed, or monolithically formed, such that rotation of central gear 3350 directs stem 3252 to rotate in a corresponding direction and rate of rotation.

Figure 24:
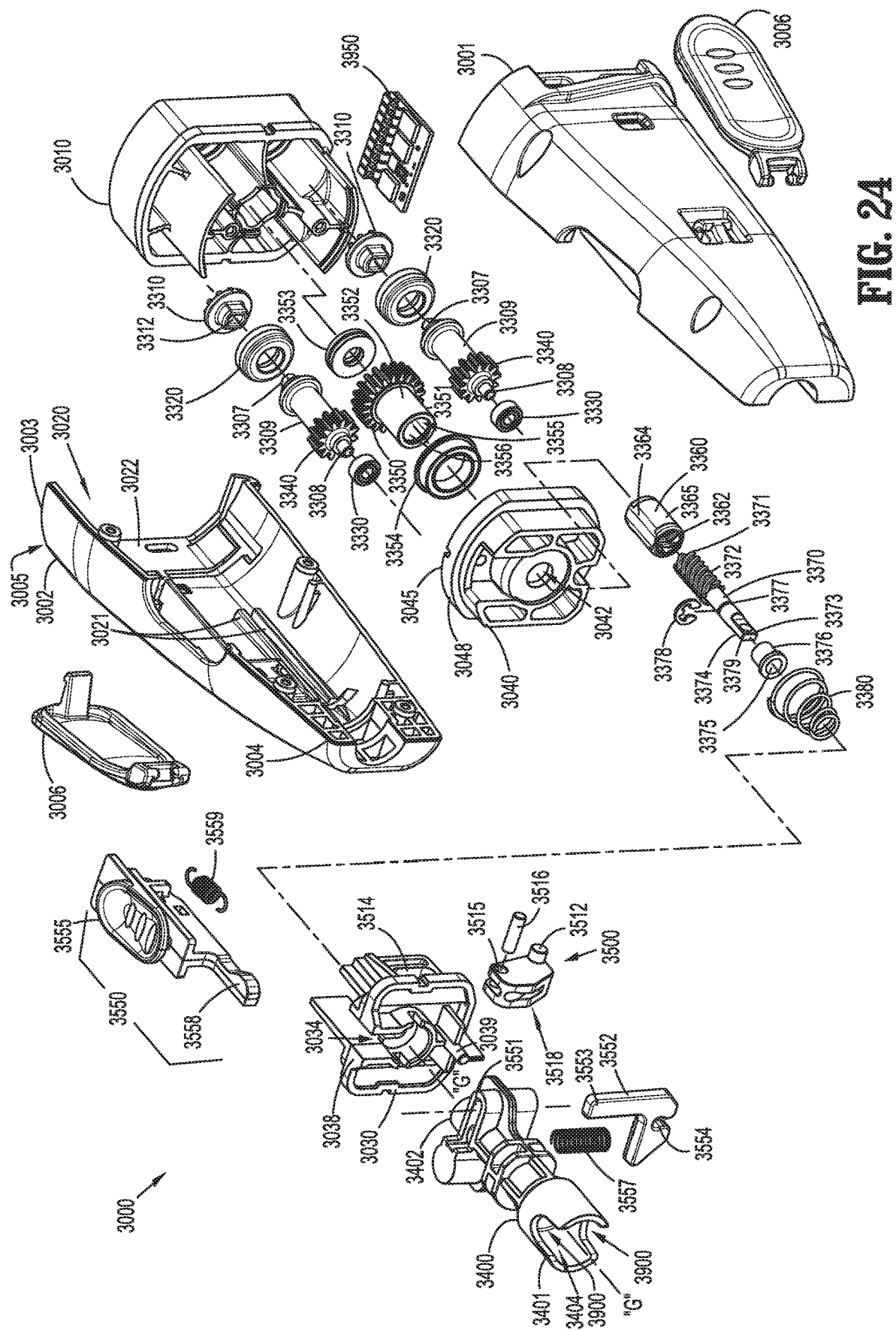
FIG. 24 is a perspective view, with parts separated, of the instrument drive assembly of FIG. 22.

With continued reference to FIGS. 24-26, drive assembly 3300 further includes a coupler 3360, a drive screw 3370, a stop cap 3376, and a clip 3378. Coupler 3360 defines a threaded aperture 3362 and a key feature 3364 on an external surface 3365 thereof. Coupler 3360 is disposed within recess 3355 of stem 3352 of central gear 3350, and is linearly and rotationally fixed therewith. Key feature 3364 mates with a corresponding key feature 3356 of recess 3355 such that rotation of central gear 3350 directs coupler 3360 to rotate in a corresponding direction and rate of rotation. Drive screw 3370 includes a threaded portion 3372 disposed about a proximal portion 3371 thereof configured to engage threaded aperture 3362 of coupler 3360, and a coupling feature 3374 disposed at a distal portion 3373 thereof. Thus, coupler 3360 interconnects drive screw 3370 and central gear 3350. Distal portion 3373 of drive screw 3370 extends distally from coupler 3360, such that coupling feature 3374 is positioned within a proximal portion 3036 of elongated cavity 3034 of distal end plate 3030. Drive assembly 3300 may further include a drive spring 3380 disposed about drive screw 3370 and interposed between internal plate 3040 and stop cap 3376 or a proximal edge 3032 of elongated cavity 3034 of distal end plate 3030. Drive spring 3380 serves to dampen the linear translation of drive screw 3370.

Coupling feature 3374 of drive screw 3370 engages coupling assembly 3500. With brief reference to FIG. 24, distal end plate 3030 pivotably supports coupling assembly 3500 thereon. Coupling assembly 3500 of instrument drive assembly 3000 is configured to mechanically engage instrument drive shaft 1020 of surgical instrument 1000, such that proximal and distal translation of drive screw 3370, with respect to coupler 3360, results in proximal and distal translation of instrument drive shaft 1020. Linear translation of drive screw 3370 is configured to drive a function of the end effector of surgical instrument 1000 in a similar fashion as drive member 380 of instrument drive assembly 200, and drive plate 2350 of instrument drive assembly 2000, and thus will not be discussed in any further detail herein. Linear translation of drive screw 3370 further directs locking and unlocking of coupling assembly 3500 with respect to instrument drive shaft 1020.

During rotation of coupler 3360, via rotation of central gear 3350, threaded aperture 3362 of coupler 3360 engages and drives threaded portion 3372 of drive screw 3370. As coupler 3360 is caused to rotate about longitudinal axis "E" of housing assembly 3005, drive screw 3370 translates linearly with respect to coupler 3360. Thus, rotational motion of central gear 3350, via engagement assembly 3302, is transferred into linear motion of drive screw 3370, via engagement between threated aperture 3362 of coupler 3360 and threaded portion 3372 of drive screw 3370. Accordingly, as central gear 3340 rotates about longitudinal axis "E", coupler 3360 also rotates about longitudinal axis "E", and drive screw 3370 engaged therewith is caused to translate linearly, with respect to coupler 3360, along longitudinal axis "E" as a result of the threaded relationship therebetween.

A stop cap 3376 is disposed about drive screw 3370 distal of threaded portion 3372, such that proximal portion 3371 of drive screw 3370 may slide linearly within a through-hole 3375 of stop cap 3376. A clip 3378 is disposed about drive screw 3370 distal of stop cap 3376, and is configured to engage recess 3377 defined on drive screw 3370. It should be appreciated that clip 3378 affixes stop cap 3376 at a position between threaded portion 3372 and coupling feature 3374. Further, stop cap 3376 and clip 3378 engage a recess 3031 disposed on proximal edge 3032 of elongated cavity 3034 of distal end plate 3030. During linear translation of drive screw 3370, with respect to coupler 3360, stop cap 3376 defines a maximum distal position of drive screw 3370. More particularly, with stop cap 3376 engaged with recess 3031 of distal end plate 3030, as drive screw 3370 translates distally to a maximum distal position, threaded portion 3372 thereof comes into abutment with stop cap 3376, whereby stop cap 3376 is linearly fixed via clip 3378 and engagement with distal end plate 3030, thus inhibiting further distal translation of drive screw 3370.

With continued reference to FIGS. 24 and 26, housing assembly 3005 includes a coupling tube 3400. Coupling tube 3400 extends distally from housing assembly 3005 and is configured to receive instrument sleeve 1010 and instrument drive shaft 1020 of surgical instrument 1000 in a similar manner to that of coupling tube 2400 of instrument drive unit 2000. Coupling tube 3400 includes a proximal end 3402 defining a through-hole 3403, and a longitudinal bore or lumen 3405 extending distally therefrom. It is envisioned that longitudinal bore 3405 defines a larger diameter than through-hole 3403, such that longitudinal bore 3405 is configured to receive both instrument sleeve 1010 and instrument drive shaft 1020 of surgical instrument 1000 therein, and through-hole 3403 is configured to receive only instrument drive shaft 3020 therethrough. Coupling tube 3400 is supported in elongated cavity 3034 of distal end plate 3030 of housing assembly 3005 such that a distal portion 3401 of coupling tube 3400 extends distally therefrom. It is envisioned that coupling tube 3400 may be monolithically formed with distal end plate 3030, or may alternatively be releasably couplable to elongated cavity 3034, such that coupling tube 3400 slides into and out of engagement with elongated cavity 3030. Longitudinal bore 3405 and through-hole 3403 of coupling tube 3400 define a longitudinal axis "G" of coupling tube 3400 (FIG. 24), which may be coaxial with longitudinal axis "E" of housing assembly 3005. Longitudinal bore 3405 is configured to slidingly receive proximal portion 1009 of instrument sleeve 1010. It is envisioned that during coupling of surgical instrument 1000 with instrument drive assembly 3000, coupling tube 3400 may aid alignment of instrument drive shaft 1020 and drive assembly 3300. More specifically, instrument sleeve 1010 of surgical instrument 1000 is slidably inserted into a distal opening 3404 of coupling tube 3400. When instrument sleeve 1010 of surgical instrument 1000 is fully inserted into longitudinal bore 3405 of coupling tube 3400, proximal end 1011 of instrument sleeve 1010 abuts a distally facing surface of proximal end 3402 of coupling tube 3400.

Housing assembly 3005 further includes a retention mechanism 3550 configured to releasably retain or secure instrument sleeve 1010 of surgical instrument 1000 to coupling tube 3400, and thus to housing assembly 3005. With reference to FIGS. 24-29C, retention mechanism 3550 includes a latch plate 3552, a button 3555, and a cam arm 3558 extending from button 3555. Coupling tube 3400 of housing assembly 3005 defines a locking cavity 3551 disposed distal of proximal end 3402 which extends into longitudinal bore 3405. Latch plate 3552 includes an arm 3553 and a pivot recess 3554. Pivot recess 3554 is configured to pivotably couple with a pivot stem 3039 of distal end plate 3030 being laterally off-set from longitudinal axis "E" of housing assembly 3005, whereby pivot stem 3039 extends distally from distal end plate 3030. More particularly, latch plate 3552 pivots about pivot recess 3554 and pivot stem 3039 transverse to longitudinal axis "E" of housing assembly 3005 and longitudinal axis "G" of coupling tube 3400.

Figure 27A:
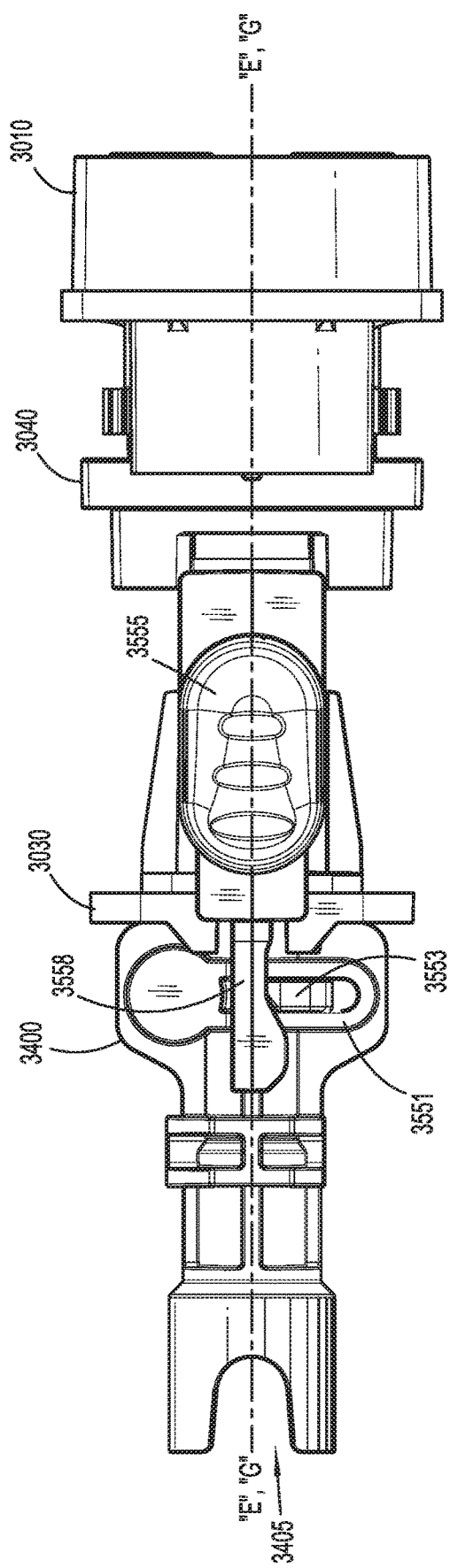
FIGS. 27A and 27B are top views of a button and a latch plate of a retention mechanism of the instrument drive assembly of FIG. 22 in a first position and a second position, respectively.
Figure 27B:
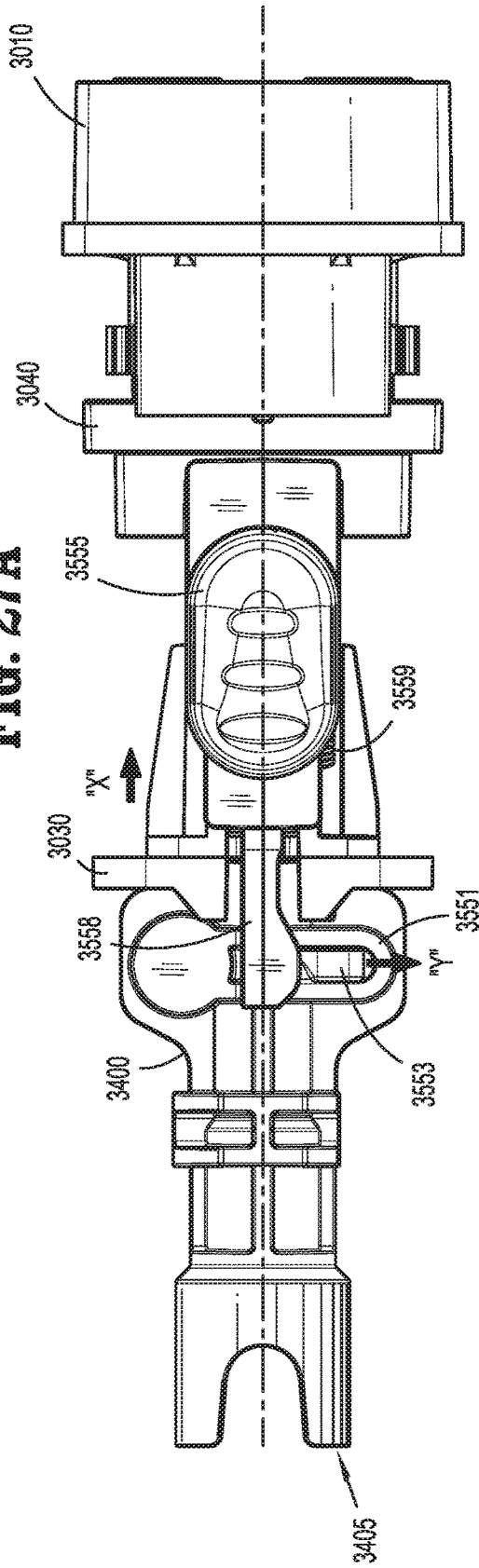
Figure 28A:
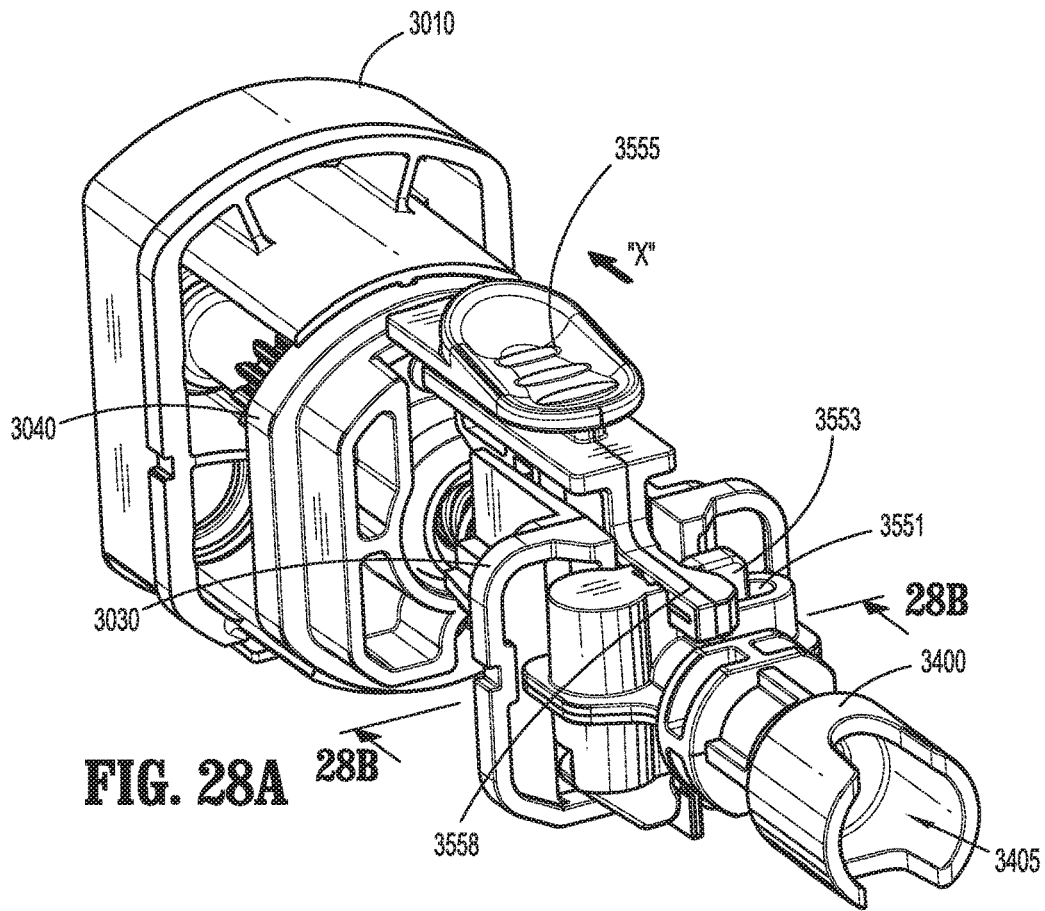
FIGS. 28A-28D are side perspective views and cross-sections of the retention mechanism of the instrument drive assembly of FIG. 22 in various states of actuation.
Figure 28B:
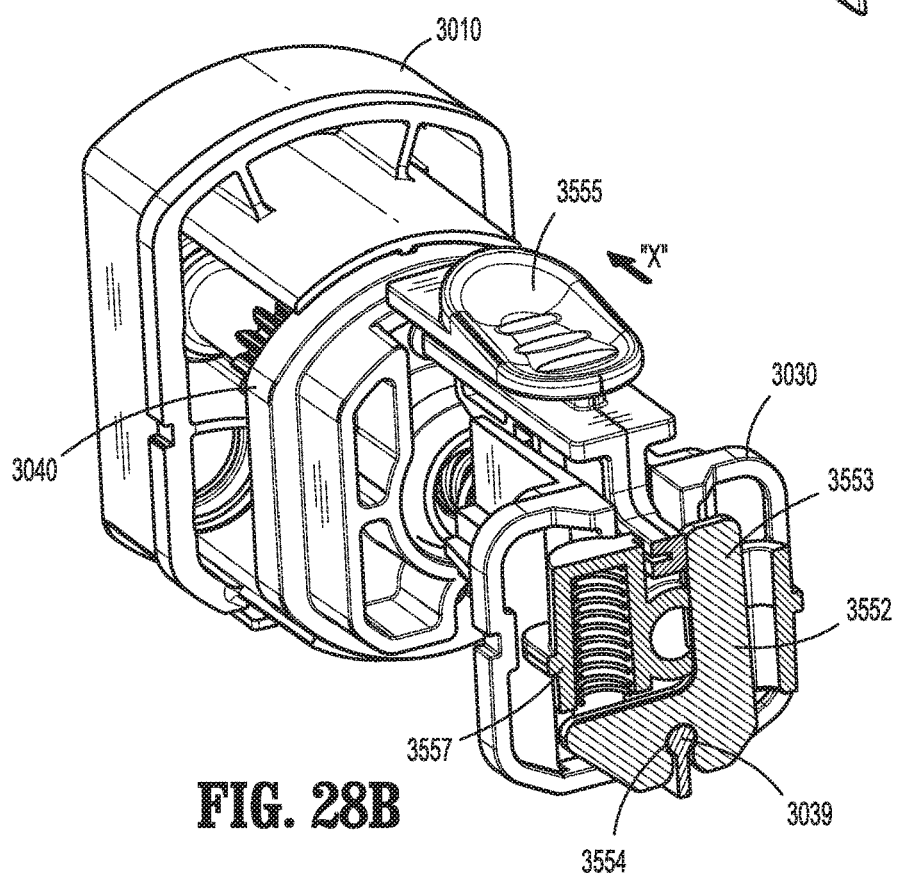
Figure 28C:
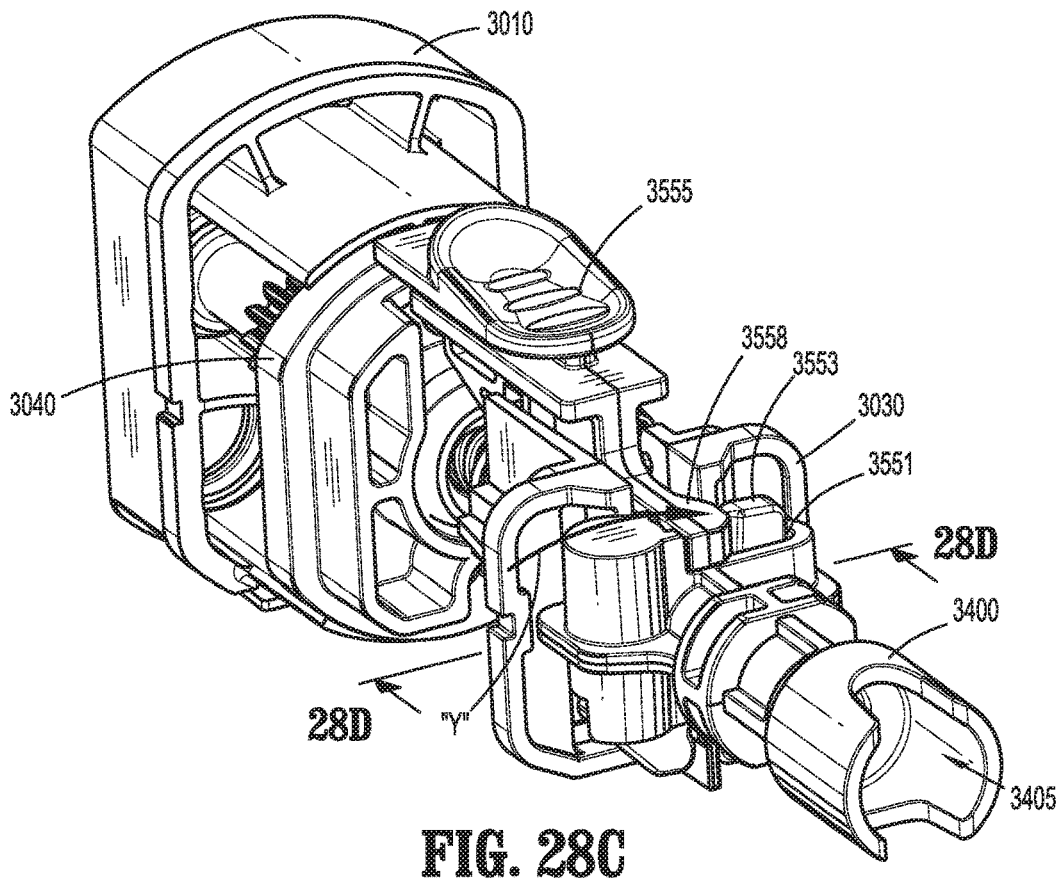
Figure 28D:
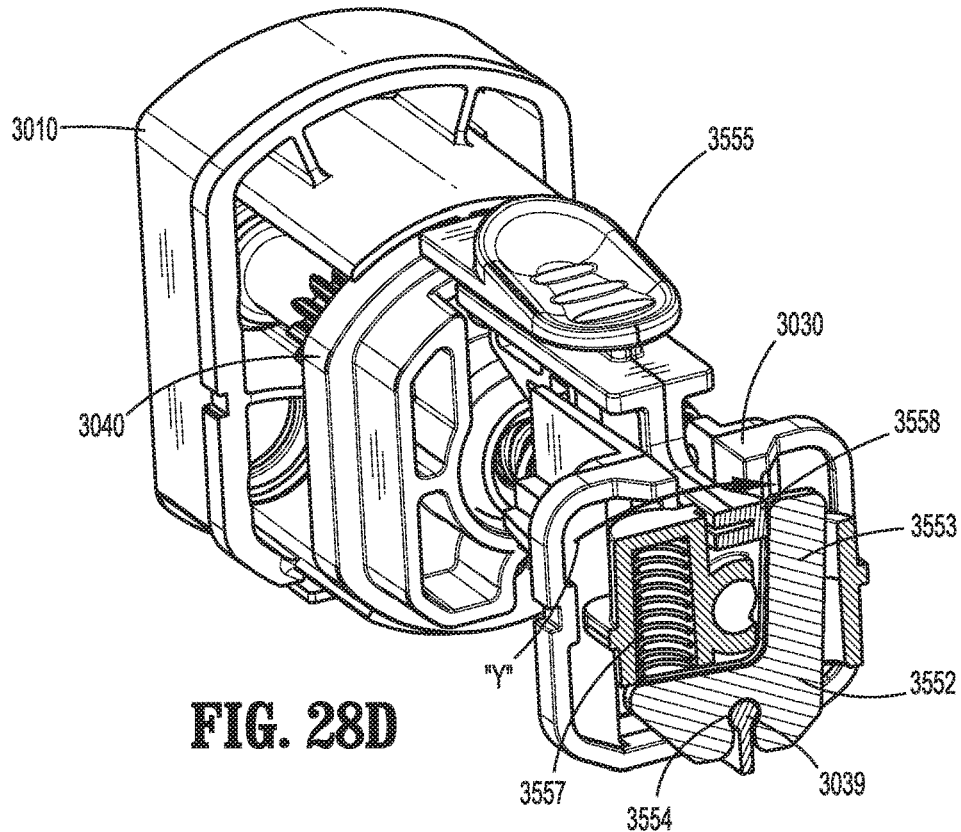

With latch plate 3552 pivotably coupled to pivot stem 3039, latch plate 3552 is disposed within locking cavity 3551 such that as latch plate 3552 pivots, arm 3553 of latch plate 3552 pivots into and out of alignment with longitudinal bore 3405 of coupling tube 3400. As such, latch plate 3552 pivots between locked and unlocked configurations, with respect to instrument sleeve 1010. More specifically, in the locked configuration arm 3553 of latch plate 3552 is positioned within longitudinal bore 3405 of coupling tube 3400 and intersects the longitudinal axis "G" thereof (FIGS. 27A, 28A, and 28B), and in the unlocked configuration arm 3553 of latch plate 3552 is positioned out of longitudinal bore 3405 of coupling tube 3400 and is off-axis of, and offset or angled from, the longitudinal axis "G" thereof (FIGS. 27B, 28C, and 28D).

It should be appreciated that button 3555 acts as an instrument release button similar to that of button 2555 of instrument drive unit 2000, such that instrument sleeve 1010 is releasably couplable to instrument drive unit 3000. Button 3555 is slidably coupled to housing assembly 3005 and linearly transitionable between first and second positions with respect to distal end plate 3030. Linear articulation of button 3555 between first and second positions acts to transition latch plate 3552 between the locked and unlocked configurations, respectively. More particularly, as button 3555 translates proximally from the first position (FIGS. 27A, 28A, and 28B) towards the second position (FIGS. 27B, 28C and 28D) in the direction of arrow "X", with respect to distal end plate 3030, cam arm 3558 of button 3555 engages arm 3553 of latch plate 3552. As cam arm 3558 engages arm 3553, arm 3553 is caused to pivot in the direction of arrow "Y" out of longitudinal bore 3405, bringing latch plate 3552 into the unlocked configuration (FIGS. 27B, 28C and 28D) with respect to instrument sleeve 1010. As should be appreciated, as button 3555 translates distally, with respect to distal end plate 3030, from the first position towards the second position, cam arm 3558 is disengaged with arm 3553 of latch plate 3552 permitting arm 3553 to pivot into alignment with longitudinal bore 3405 bringing latch plate 3552 into the locked configuration (FIGS. 27A, 28A, and 28B) with respect to instrument sleeve 1010.

Retention mechanism 3550 may further include a first biasing member 3557 interposed between latch plate 3552 and coupling tube 3400, such that latch plate 3552 is biased into or out of locking cavity 3551, and thus biased into either the locked or unlocked configuration. Further, retention mechanism 3550 may include a second biasing member 3559 interposed between button 3555 and distal end plate 3030, such that button 3555 is biased into either the first or second position.

Figure 29A:
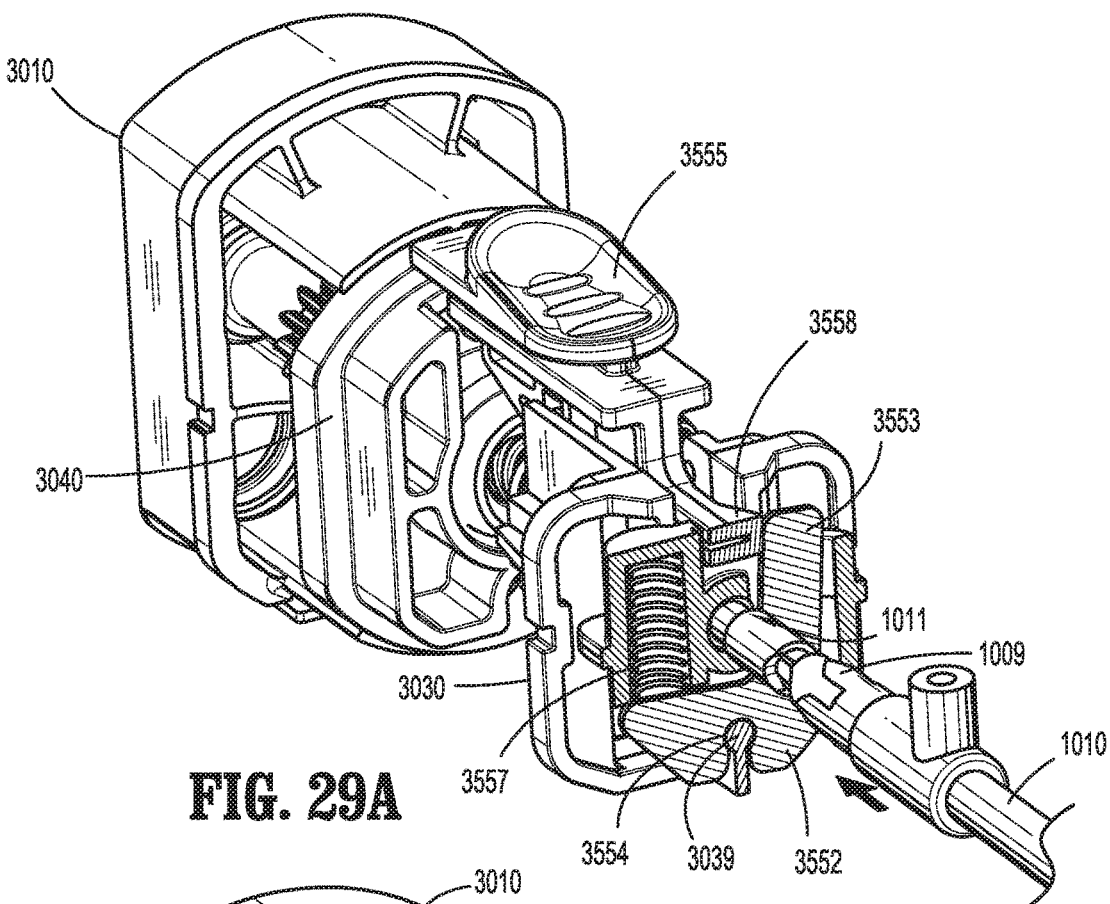
FIGS. 29A and 29B are perspective views.
Figure 29B:
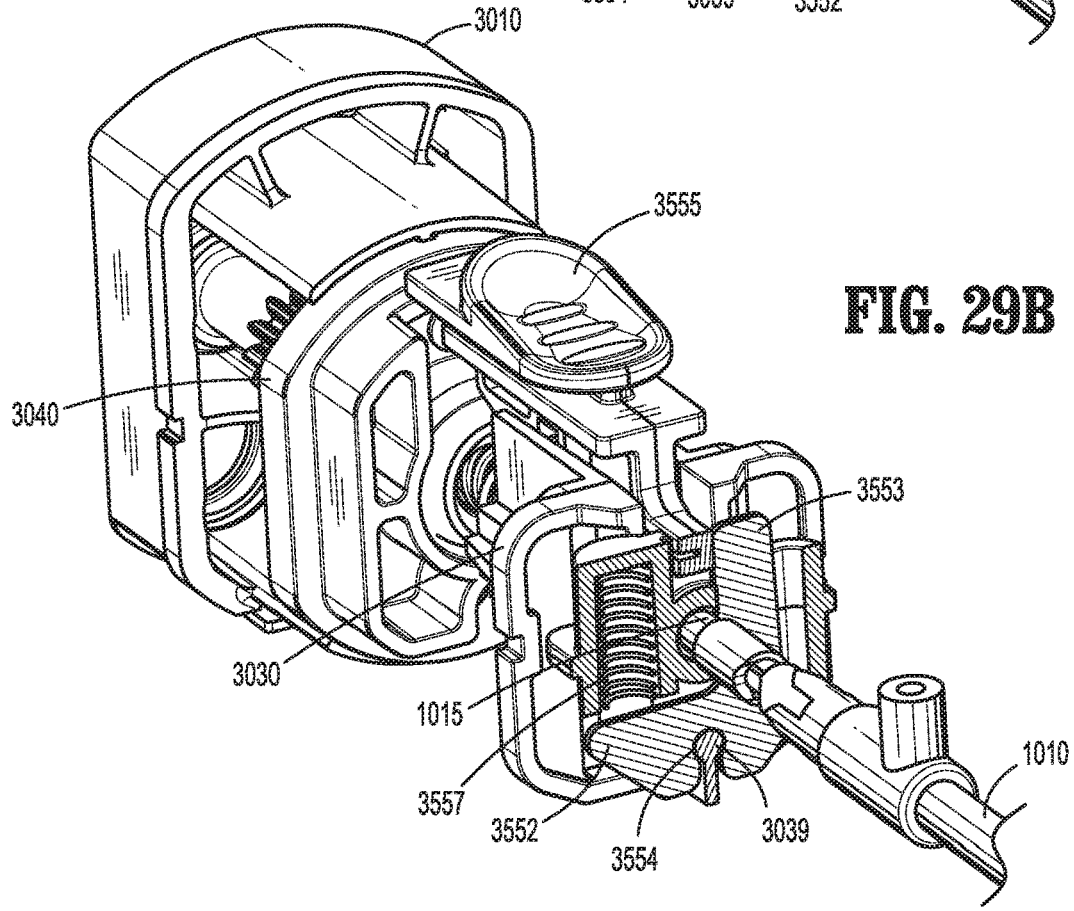

With continued reference to FIGS. 27A-29C, coupling and uncoupling of instrument sleeve 1010 of surgical instrument 1000 to retention mechanism 3550 of instrument drive assembly 3000 will be discussed. During coupling of instrument sleeve 1010 to coupling assembly 3500, instrument sleeve 1010 is inserted into distal opening 3404 of coupling tube 3400 and slid proximally therein (FIG. 29A). As the proximal end 1011 of instrument sleeve 1010 approaches proximal end 3402 of coupling tube 3400, the proximal end 1011 of instrument sleeve 1010 urges arm 3553 of latch plate 3552 to transition into the unlocked configuration (e.g., arm 3553 pivots within locking cavity 3551 of coupling tube 3400 and into a position out of longitudinal bore 3405 and off axis of longitudinal axis "G" of coupling tube 3400) (FIGS. 27B, 28C, 28D, and 29A). As instrument sleeve 1010 continues to slide proximally, arm 3553 aligns with recess 1015 of instrument sleeve 1010, such that arm 3553 is permitted to pivot into the locked configuration (e.g., arm 3553 pivots within locking cavity 3551 of coupling tube 3400 and into engagement with recess 1015 of instrument sleeve 1010) (FIG. 29B). With arm 3553 of latch plate 3552 engaged within recess 1015 of instrument sleeve 1010, longitudinal translation of instrument sleeve 1010, within coupling tube 3400, is inhibited. In an embodiment with first biasing element 3557, latch plate 3552 may be biased into the locked configuration, such that arm 3553 is biased into engagement with recess 1015 and thus springs into engagement with recess 1015 upon insertion of instrument sleeve 1010.

Figure 29C:
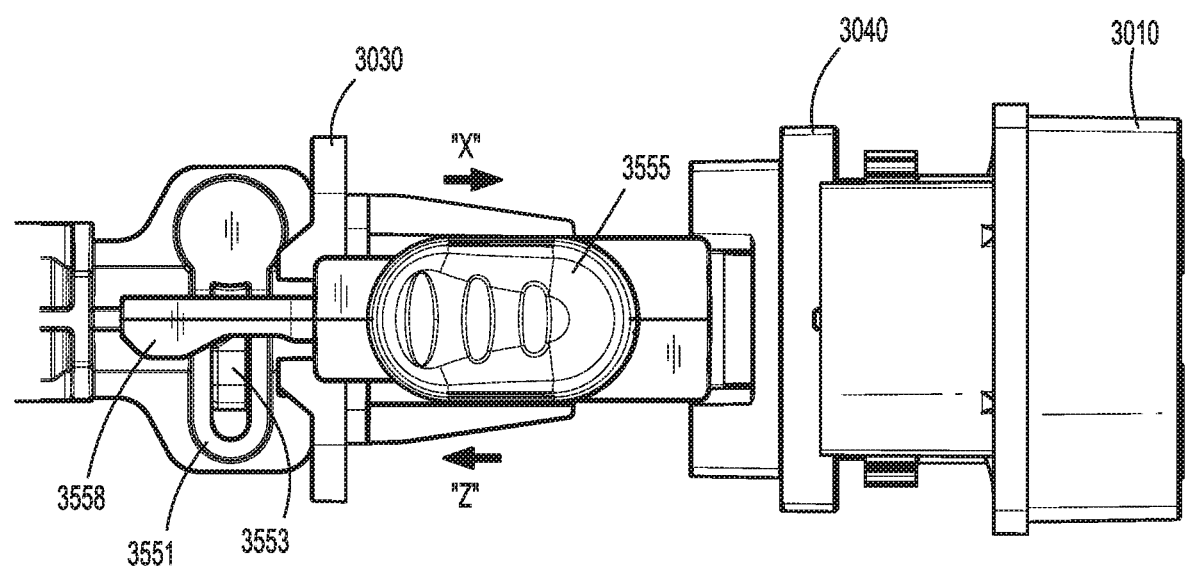
FIG. 29C is a top view, of the retention mechanism of FIGS. 28A-28D in various states of actuation during insertion of an instrument sleeve therein.

It should be appreciated that button 3555 may be slide proximally from the first position towards the second position in the direction of arrow "X" during coupling of instrument sleeve 1010 and retention mechanism 3550, wherein button 3555 is slid distally from the second position towards the first position in the direction of arrow "Z" once instrument sleeve 1010 is fully inserted within coupling tube 3400 and arm 3553 aligns with recess 1015 (FIG. 29C). In an embodiment with second biasing element 3559, button 3555 may be biased towards the first position in the direction of arrow "Z" (e.g., cam arm 3558 is biased out of engagement with arm 3553), such that once arm 3553 engages recess 1015 of instrument sleeve 1010 button 3555 springs towards the first position.

During uncoupling of instrument sleeve 1010 of surgical instrument 1000 from retention mechanism 3550 of instrument drive assembly 3000, button 3555 is transitioned from the first position (e.g., the proximal position illustrated in FIGS. 27A, 28A, 29B, and 29C) towards the second position (e.g., the distal position illustrated in FIGS. 27B, 28C, 29A) in the direction of arrow "X". As button 3555 slides towards the second position, cam arm 3558 of button 3555 cams along arm 3553 of latch plate 3552, causing arm 3553 to pivot into a position out of longitudinal bore 3405 and off axis of longitudinal axis "G" of coupling tube 340 into the unlocked configuration (e.g., arm 3553 pivots within locking cavity 3551 of coupling tube 3400 out of engagement with recess 1015 of instrument sleeve 1010) (FIGS. 28D and 29A). With arm 3553 pivoted out of the recess 1015 of instrument sleeve 1010, instrument sleeve 1010 is free to be withdrawn from and uncoupled from coupling tube 3400.

With reference to FIGS. 24 and 25, coupling assembly 3500 of instrument drive assembly 3000 will be discussed. Coupling assembly 3500 is disposed in cavity 3020 of housing assembly 3005 and is pivotably supported by distal end plate 3030. Coupling assembly 3500 serves to releasably couple instrument drive shaft 1020 of surgical instrument 1000 to drive assembly 3300.

Coupling assembly 3500 includes a drive link 3510 configured to engage with, and couple to, instrument drive shaft 1020 of surgical instrument 1000. Drive link 3510 is pivotably coupled to distal end plate 3030 via a set of opposing protrusions 3512 extending therefrom which reside within a slot 3514 defined through distal end plate 3030. It is envisioned that opposing protrusions 3512 may be monolithically formed with drive link 3510, or alternatively, may define a pin which passes therethrough to reside within slot 3514. A pin 3516 couples drive link 3510 and coupling feature 3374 of drive screw 3370, such that pin 3516 passes through a pinhole 3515 of drive ink 3510 and coupling feature 3374. In such an embodiment, coupling feature 3374 may define a through-hole 3379 which may be transverse to longitudinal axis "E" of housing assembly 3005. In an embodiment, coupling feature 3374 may define a boss or protrusion which engages pinhole 3515, thereby coupling drive screw 3370 and drive link 3510.

As such, when coupled, drive link 3510 is pivotably coupled to distal end plate 3030, via engagement of protrusions 3512 of drive link 3510 and slot 3514 of distal end plate 3030, and pivotably coupled to drive screw 3370, via engagement of pin 3516 and through-hole 3379 of coupling feature 3374 of drive screw 3370. Thus, drive link 3510 is transitionable between a locked position (FIG. 30C) and an unlocked position (FIGS. 30A and 30B), with respect to instrument drive shaft 1020 of surgical instrument 1000. More specifically, as drive screw 3370 of drive assembly 3300 translates proximally or distally, as discussed above, drive link 3510 is caused to pivot about protrusions 3512. Accordingly, similar to that of instrument drive unit 2000, instrument drive shaft 1020 may be coupled and uncoupled from instrument drive unit 3000 through the cooperation of the linear translation of drive screw 3370 and the pivoting of drive link 3510.

Figure 30A:
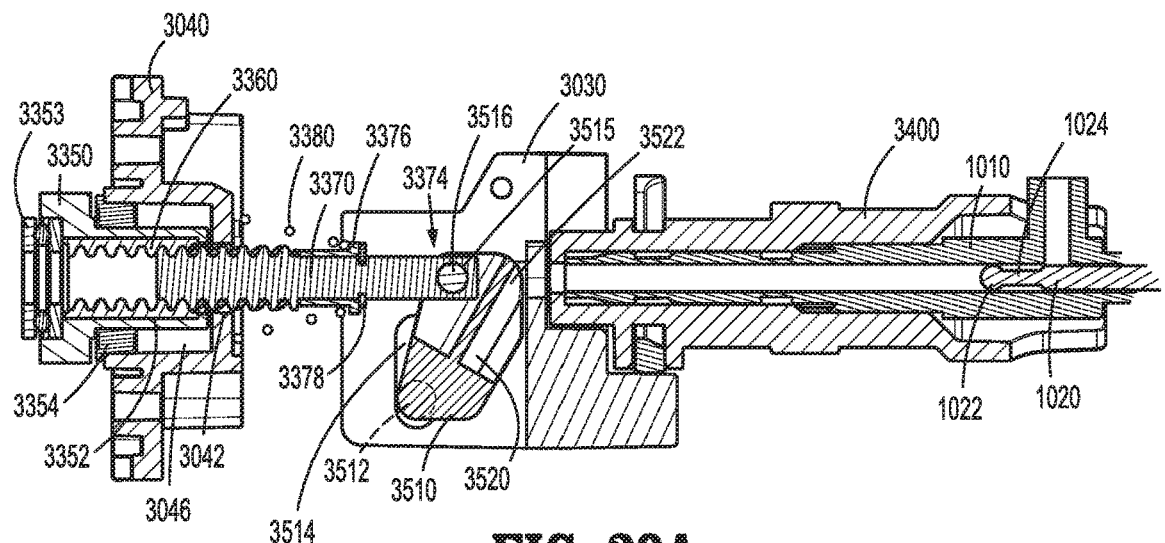
FIGS. 30A-30C are side, cross-sectional views of a coupling assembly of the instrument drive assembly of FIG. 22 in various states of actuation during coupling of an instrument drive shaft therewith.
Figure 30B:
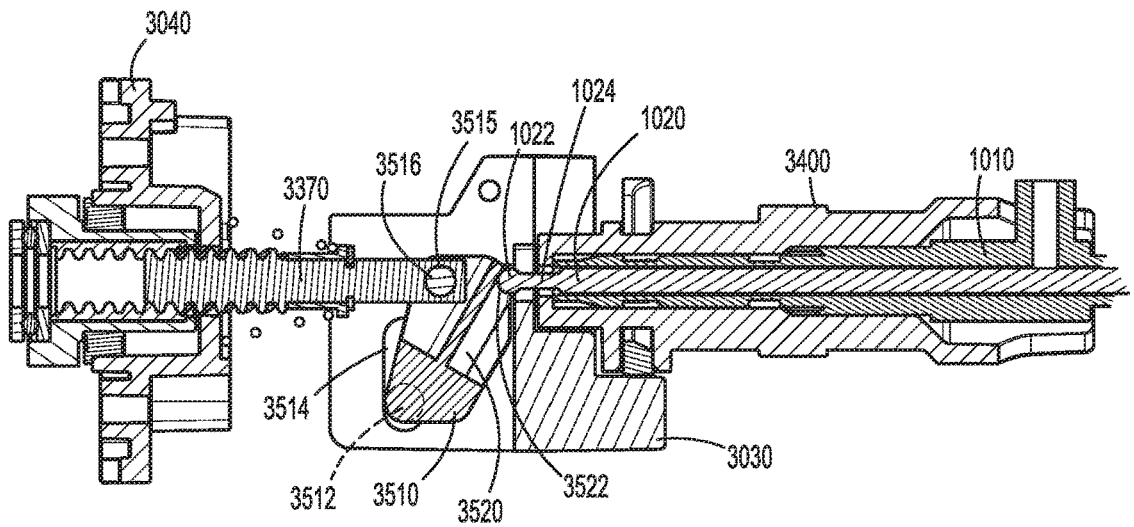
Figure 30C:
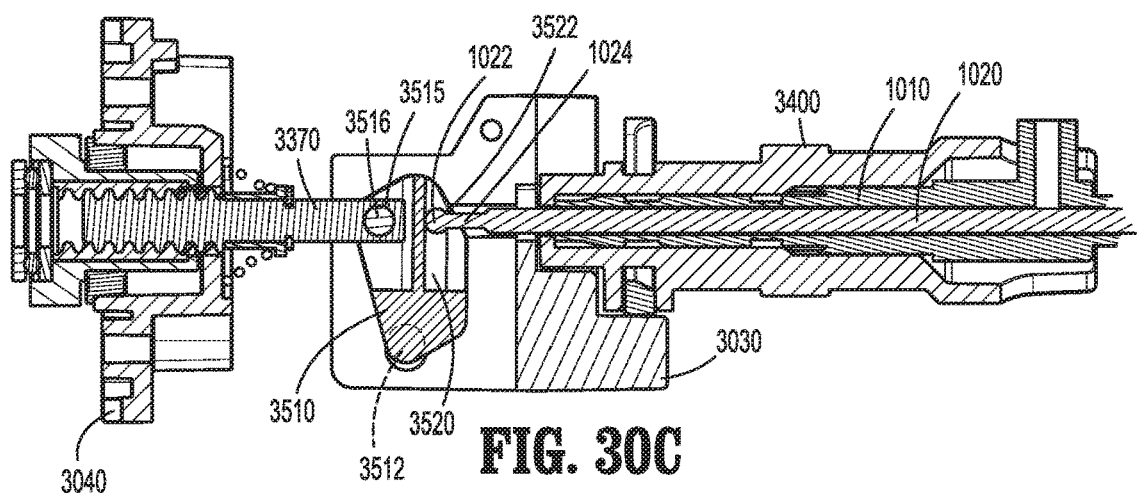
Figures 31A, 31B:
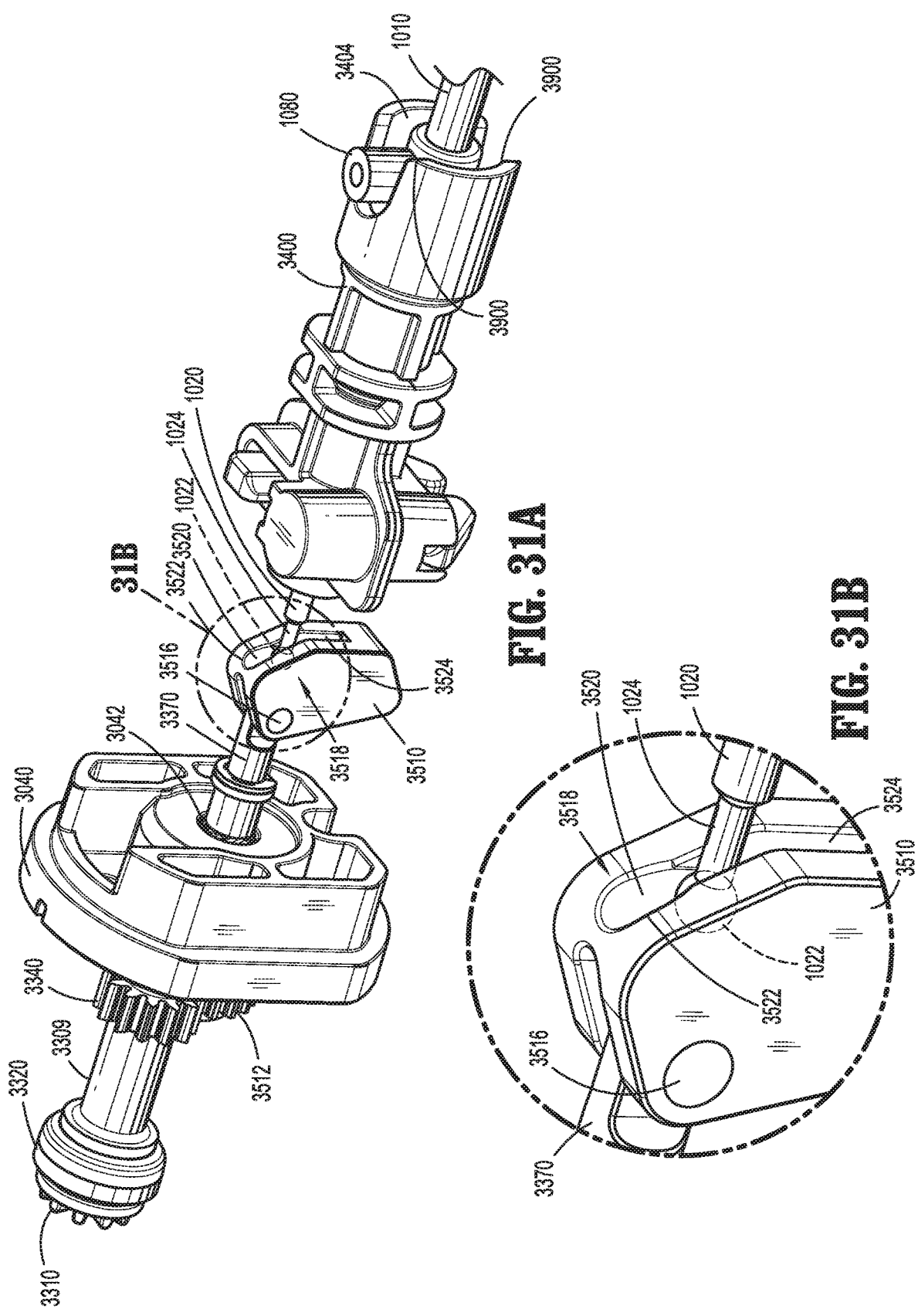
FIG. 31A is a perspective view of a drive assembly and a drive link of the instrument drive assembly of FIG. 22 coupled with the instrument drive shaft.
FIG. 31B is a perspective view of the area of detail of FIG. 31A.

With reference to FIGS. 31A and 31B, drive link 3510 of coupling assembly 3500 further defines a receiving region 3518 disposed on a distal facing surface thereof, which is configured to releasably retain and secure coupling ball 1022 of instrument drive shaft 1020. Receiving region 3518 of drive link 3510 defines a cavity 3520 therein, a port 3522 extending into cavity 3520, and a channel 3524 extending along cavity 3520. Receiving region 3518 of drive link 3510 acts as a socket joint for coupling ball 1022 of instrument drive shaft 1020, where coupling ball 1022 can only enter and exit cavity 3520 through port 3522. Through pivoting of drive link 3510 between the unlocked and locked positions, port 3522 is correspondingly oriented to be aligned with, or brought off axis of, or angled from, the longitudinal axis "G" of coupling tube 3400, respectively. More specifically, with drive link 3510 in the unlocked position (FIGS. 30A and 30 B), port 3522 is aligned with longitudinal axis "G", such that coupling ball 1022 of instrument drive shaft 1020 may be received therein. Once drive link 3510 is pivoted to the locked position (FIGS. 30C-31B), port 3522 is brought off-axis of, or angled from, longitudinal axis "G" of coupling tube 3400, and coupling ball 1022 of instrument drive shaft 1020 is captured within cavity 3520. In the locked position, neck 1024 of instrument shaft 1020 resides in channel 3524 of receiving region 3518 of drive link 3510, where channel 3524 is configured to be smaller than a diameter of coupling ball 1022, thus capturing coupling ball 1022 within cavity 3520 of receiving region 3518 of drive link 3510. As such, port 3522 of receiving region 3518 of drive link 3510 is configured to receive coupling ball 1022 of instrument drive shaft 1020 therethrough, while channel 3524 of receiving region 3518 of drive link 3510 is configured to inhibit coupling ball 1022 from leaving cavity 3520. With reference to FIGS. 31A and 31B, coupling ball 1022 (shown in phantom) is disposed in cavity 3520 of receiving region 3518 and neck 1024 is disposed in channel 3524.

With reference to FIGS. 30A-30C, the engagement of instrument drive shaft 1020 of surgical instrument 1000 to coupling assembly 3500 of instrument drive assembly 3000 will be discussed. As discussed above, proximal and distal translation of drive screw 3370 of drive assembly 3300 pivots drive link 3510 between the unlocked and locked positions, such that coupling assembly 3500 transitions between the unlocked and locked configuration, respectively. With drive screw 3370 in a distal most position, drive link 3510 is in the unlocked position and coupling assembly 3500 is in the unlocked configuration, such that port 3522 of drive link 3510 is aligned with longitudinal axis "G" of coupling tube 3400 (FIGS. 30A and 30B). With port 3522 aligned with longitudinal axis "G", instrument drive shaft 1020 is inserted into the distal opening 3404 of coupling tube 3400 and translated proximally, such that coupling ball 1022 of instrument drive shaft 1020 is brought into approximation with port 3522 of receiving region 3518 of drive link 3510. As instrument drive shaft 1020 translates proximally, coupling ball 1022 is inserted through port 3522 and brought into cavity 3520 of retention region 3518 of drive link 3510

(FIG. 30B). With coupling ball 1022 residing in cavity 3520, drive screw 3370 is translated proximally. As drive screw 3370 is translated proximally, drive link 3510 pivots about protrusions 3512 into the locked position. With drive link 3510 in the locked position, neck 1024 of instrument shaft 1020 is disposed in channel 3524 of drive link 3510, thus capturing coupling ball 1022 within cavity 3520 of receiving region 3518 of drive link 3510 (FIG. 30C). Further, in the locked position, port 3522 of receiving region 3518 of drive link 3510 is brought off axis of, or angled from, the longitudinal axis "G" of coupling tube 3400. With drive link 3510 pivoted into the locked position coupling assembly 3500 is thus in the locked configuration with respect to instrument drive shaft 1020. With coupling assembly 3500 in the locked configuration, further proximal movement of drive screw 3370 causes drive link 3510 to pivot past the locked position directing proximal translation of instrument drive shaft 1020. Accordingly, proximal translation of drive screw 3370 causes drive link 3510 to pivot past the locked position, thus directing proximal translation of instrument drive shaft 1020, which actuates the end effector (not shown) disposed at the distal end of instrument drive shaft 1020.

With reference to FIGS. 27A-31B, a complete coupling and decoupling of instrument drive assembly 3000 to surgical instrument 1000 will be briefly discussed. Initially, instrument sleeve 1010 of surgical instrument 1000 is inserted into coupling tube 3400 of housing assembly 3005 and translated proximally until arm 3553 of latch plate 3552 of retention mechanism 3550 is brought into engagement with recess 1015 of instrument sleeve 1010, thus inhibiting any further translation of instrument sleeve 1010. It should be appreciated that coupling of instrument sleeve 1010 and retention mechanism 3550 may be performed with button 3555 of retention mechanism 3550 in either the first or second position. Next, drive screw 3370 of drive assembly 3300 is translated into a distal most position, such that drive link 3510 is pivoted into the unlocked position and coupling assembly 3500 is brought into the unlocked configuration. Instrument drive shaft 1020 is then inserted proximally through instrument sleeve 1010 until coupling ball 1022 is engaged with drive link 3510. Alternatively, it is envisioned that instrument sleeve 1010 may be omitted, and thus instrument drive shaft 1020 may be inserted directly through coupling tube 3400. Once coupling ball 1022 is disposed in receiving region 3518 of drive link 3510, drive screw 3370 is translated proximally, such that drive link 3510 is pivoted into the locked position, and coupling assembly 3500 is translated into the locked configuration. Once instrument drive shaft 1020 is coupling with drive link 3510, further proximal translation of drive screw 3370 directs actuation, articulation, or firing of the end effector of surgical instrument 1000.

During decoupling, drive screw 3370 of drive assembly 3300 is returned to the distal most position, such that drive link 3510 pivots to the unlocked position, and coupling assembly 3500 transitions into the unlocked configuration. Instrument drive shaft 1020 of surgical instrument 1000 may now by translated distally, such that coupling ball 1022 is brought out of, or withdrawn from, receiving region 3518 of drive link 3510, and decoupled from instrument drive assembly 3000. Button 3555 of retention mechanism 3500 may then be translated from the first position (e.g., distal position) towards the second position (e.g., proximal position), such that cam arm 3558 of button 3555 engages and pivots arm 3553 of latch plate 3552 out of engagement with recess 1015 of instrument sleeve 1010 of surgical instrument 1000. Instrument sleeve 1010 may now be translated distally and withdrawn from coupling tube 3400. It is envisioned that outer sleeve 1010 and instrument drive shaft 1020 may be configured to be coupled, and uncoupled, independently and/or in any order.

During use of instrument drive assembly 3000, it should be appreciated that rotation of proximal gear 3310 of drive assembly 3300 in a first direction (e.g., clockwise) causes central gear 3350 to rotate in an opposing direction, which directs drive screw 3370 to translate in a first linear direction (e.g., proximally), and pivots drive link 3510 (e.g., towards the locked position as illustrated in FIG. 30C). Further translation of drive screw 3370 in the first linear direction causes drive link 3510 to continue to pivot, past the locked position, such that instrument drive shaft 1020 is translated in the first linear direction. Similarly, rotation of proximal gear 3310 of drive assembly 3300 in a second direction (e.g., counter-clockwise) causes central gear 3350 to rotate in an opposing direction, which directs drive screw 3370 to translate in a second linear direction (e.g., distally), and pivots drive link 3510 (e.g., towards the unlocked position as illustrated in FIGS. 30A and 30B). As drive link 3510 pivots from a position past the locked position towards the locked position, instrument drive shaft 1020 is driven in the second linear direction. Further translation of drive screw 3370 in the second linear direction causes drive link 3510 to continue pivoting into the unlocked position, such that instrument drive shaft 1020 may be decoupled therefrom.

It is contemplated that instrument sleeve 1010 of surgical instrument 1000 may further include a flush or inflation port 1080 disposed distally of proximal end 1011 (FIG. 11) of instrument sleeve 1010. Port 1080 may be used to introduce fluids into or out of the surgical site through longitudinal lumen 1012 of instrument sleeve 1010. Port 1080 may further be used as an alignment feature, such that at least one recess 900 or 3900 disposed along distal opening 2404 of coupling tube 2400, or a distal opening 3404 of coupling tube 3400 respectively, acts as a keying feature for instrument sleeve 1010 and/or instrument drive shaft 1020 (FIGS. 12 and 31A) of surgical instrument 1000. It is envisioned that at least two recesses 900, 3900 may be included and spaced 180° apart about distal opening 2404 of coupling tube 2400 or distal opening 3404 of coupling tube 3400. It is envisioned that coupling tube 400 of instrument drive assembly 200 may similarly define a recess disposed along distal opening 404 to serve as a keying feature when coupling instrument drive assembly 200 and instrument sleeve 1010 of surgical instrument 1000.

Further still, instrument drive assembly 3000 may include a controller 3950 disposed within housing assembly 3005 (FIG. 24). It is envisioned that instrument drive assembly 200, 2000 and 3000 may further include controller 3950. Controller 3950 is configured to identify a surgical instrument 1000 coupled thereto, either through a wired or wireless data communication (e.g., Bluetooth®, WiFI®, Zig-Bee®, RFID, etc.), such that controller 3950 may adjust and tailor the instrument drive assembly 200, 2000, or 3000 for the specific surgical tool 1000. Controller 3950 may retrieve data pertaining to the operational parameters of the identified surgical tool 1000 from an internal storage medium or an external stored medium, e.g., wired or wireless communication with medical work station 1. Such data of surgical tool 1000 may include force or torque capabilities, calibration procedures, usage data, serial or identification markers, end effector function and operational parameters, instrument sleeve 1010 and/or instrument drive shaft 1020 length, etc.

With reference to FIGS. 1-31B, a kit will be described. A kit may include one or more instrument drive assemblies 200, one or more instrument drive assemblies 2000, one or more instrument drive assemblies 3000, or any combination thereof. The kit may further include one or more surgical instruments 1000, where the end effector of each surgical instrument may vary to provide a number of end effector options to a user. It is further envisioned that the kit may include alternate instrument sleeves 1010 and/or instrument drive shafts 1020, such that the operator may interchange instrument sleeves 1010 and instrument drive shafts 1020 for a given procedure. A variety of instrument sleeves 1010 and/or instrument drive shafts 1020 defining a range of lengths and/or diameters may be provided to the user, such that the user has a variety of sized surgical instrument 1000 available.

Figure 32:
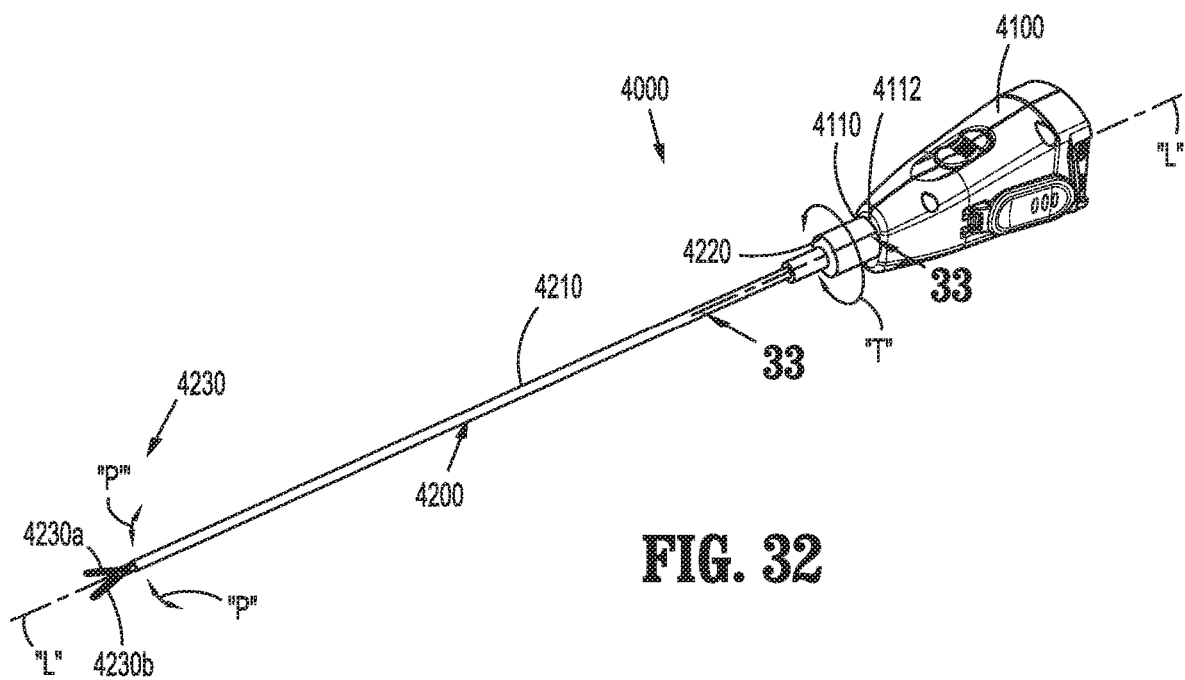
FIG. 32 is a perspective view of another embodiment of an instrument drive assembly coupled with another embodiment of a surgical instrument.
Figure 33:
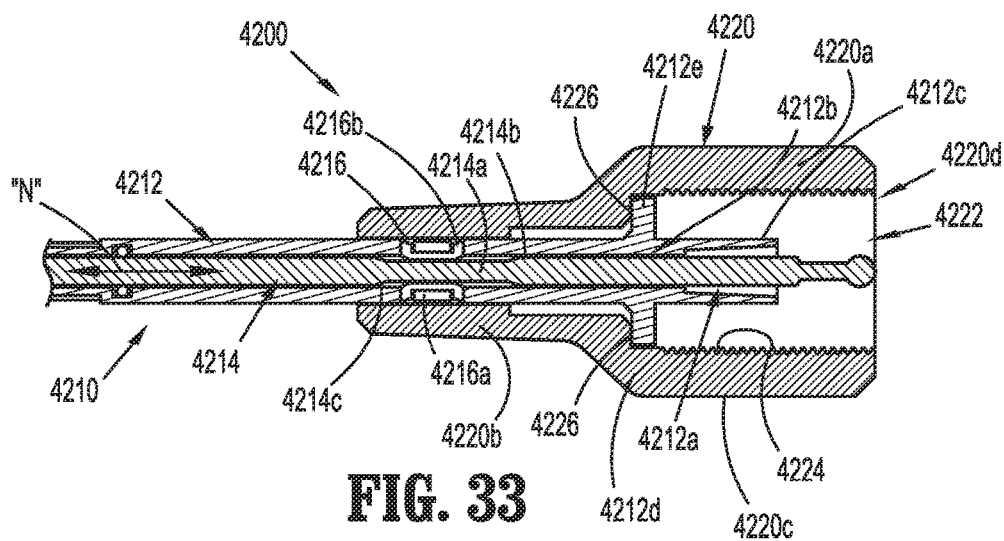
FIG. 33 is an enlarged, cross-sectional view of the surgical instrument of FIG. 32 as taken along section line 33-33 of FIG. 32.
Figure 34:
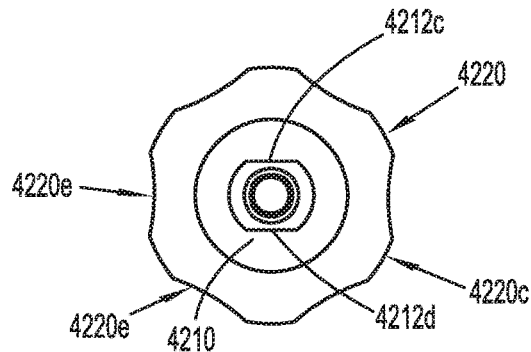
FIG. 34 is an end view of FIG. 33.

Referring now to FIGS. 32-34, a surgical assembly, generally referred to as 4000 defines a longitudinal axis "L" and includes an instrument drive assembly 4100 and a surgical instrument 4200 that are configured to selectively threadably couple together. Instrument drive assembly 4100 of surgical assembly 4000 is similar to instrument drive assemblies 200, 2000, 3000, but includes a coupling tube 4110 supported on a distal end portion of instrument drive assembly 4100. Coupling tube 4110 of instrument drive assembly 4100 includes a threaded outer surface 4112 configured to threadably couple to a proximal portion of surgical instrument 4200 to axially fix surgical instrument 4200 to instrument drive assembly 4100.

Surgical instrument 4200 of surgical assembly 4000 includes a shaft assembly 4210 that supports a knob 4220 on a proximal end portion thereof and a jaw assembly 4230 on a distal end portion thereof. Jaw assembly 4230 includes a first jaw member 4230a and a second jaw member 4230b disposed in mirrored relation to first jaw member 4230b. One or both of first and second jaw members 4230a, 4230b of jaw assembly 4230 may be movable (e.g., pivotable) relative to one another to enable first and/or second jaw members 4230a, 4230b to move between an open position (FIG. 32) and a closed position (not shown), as indicated by arrows "P" for treating tissue (e.g., one or more of grasping, cutting, stapling, sealing, etc.) captured by the first and second jaw members 4230a, 4230b.

The knob 4220 of surgical instrument 4200 includes a handle portion 4220a and nose portion 4220b that extends distally from handle portion 4220a. Knob 4220 further includes an outer surface 4220c and an inner surface 4220d. Outer surface 4220c of knob 4220 includes gripping grooves 4220e defined along handle portion 4220a of knob 4220 to enhance gripping and rotation of handle portion 4220a (e.g., relative to coupling tube 4110 of instrument drive assembly 4100). Inner surface 4220d of knob 4220 defines a bore 4222 through knob 4220 and includes threads 4224 that extend along handle portion 4220a about bore 4222. Threads 4224, along inner surface 4220d of knob 4220, are configured to threadably couple with threaded outer surface 4112 of coupling tube 4110 of instrument drive assembly 4100, as indicated by arrows "T," to enable surgical instrument 4200 and instrument drive assembly 4100 of surgical assembly 4000 to selectively threadably couple together (and/or uncouple, for example, for instrument exchange and/or cleaning/autoclaving of surgical instrument 4200). Inner surface 4220d of knob 4220 further includes an annular shoulder 4226.

Shaft assembly 4210 of surgical instrument 4200 includes an outer shaft assembly 4212 and an inner shaft 4214. Outer shaft assembly 4212 of shaft assembly 4210 defines a luer flush port 4212a (e.g., to facilitate cleaning) in a proximal end portion thereof that is in fluid communication with a lumen 4212b defined by an inner surface of outer shaft assembly 4212. Lumen 4212b of outer shaft assembly 4212 is positioned to receive the inner shaft 4214 therein and extends through outer shaft assembly 4212 from luer flush port 4212a to a distal end portion of outer shaft assembly 4212. Outer shaft assembly 4212 includes a pair of clocking flats 4212c, 4212e that are positioned to enable outer tube assembly 4212 to engage a complementary feature (not shown, but keyed to rotatably lock with clocking flats 4212c, 4212e) supported within coupling tube 4110 of instrument drive assembly 4100 so that jaw assembly 4230 of surgical instrument 4200 is maintained in either one of two orientations (e.g., one of two vertical orientations 180 degrees apart). For example, in a first orientation, clocking flat 4212c is positioned superiorly of clocking flat 4212d such that first jaw member 4230a is positioned superiorly of second jaw member 4230b. In a second orientation, clocking flat 4212d is positioned superiorly of clocking flat 4212e such that second jaw member 4230b is positioned superiorly of first jaw member 4230a.

Although shown and described as vertical orientations, clocking flats 4212c, 4212d of outer shaft assembly 4212 of surgical instrument 4200, and/or the first and/or second jaw members 4230a, 4230b of surgical instrument 4200 can have any number of orientations and/or arrangements with respect to one another (e.g., more than two orientations and/or non-vertical orientations such as lateral and/or inclined/angled orientations, etc. and which may be separated by an suitable angular arc relative to one another). For example, although shown with two clocking positions that are 180 degrees apart, any number of clocking flats may be separated by one or more arc lengths such as 45 degrees, 60 degrees, 90 degrees, 120 degrees, etc.

Outer shaft assembly 4212 of surgical instrument 4200 further includes an annular flange 4212e that is positioned to abut annular shoulder 4226 of knob 4220 of surgical instrument 4200 to prevent axial movement of outer tube assembly 4212 relative to knob 4220 and/or inner shaft 4214 of surgical instrument 4200. Outer shaft assembly 4212 also supports an insert lock assembly 4216. Insert lock assembly 4216 includes a clip 4216a (e.g., a C-clip that may include elastomeric materials) that functions to urge and/or radially constrain a lock body 4216b (which may include metallic materials) of insert lock assembly 4216 into lumen 4212b of outer shaft assembly 4212. The function of the insert lock assembly 4216 is to prevent relative rotation between inner shaft 4214 (and attached components) and outer shaft assembly 4212 (and attached components). This may be necessary to cause torsional load at one or both of first and second jaw members 4230a, 4230b of jaw assembly 4230. Knob 4220 may be advanced proximally/distally to lock/unlock insert lock assembly 4216 to enable a user to exchange tools (e.g., jaw assembly 4230), for example.

Lock body 4216b of insert lock assembly 4216 of outer tube assembly 4214 is retained by clip 4216a. In particular, clip 4215a loads lock body 4216b radially inward against outer shaft assembly 4212. Flats 4212c, 4212e on inner shaft 4214 of surgical instrument 4200 are provided such that, in some orientations, lock body 4216b is forced radially outward. When knob 4220 is advanced proximally, radial outward motion of lock body 4216b is prevented, and thus, tool rotation is also prevented. When knob 4220 is advanced distally, radial outward motion of lock body 4216b is enabled, and thus, tool rotation (e.g., jaw assembly 4230 rotation) is enabled relative to outer shaft assembly 4212. This then enables tool (e.g., jaw assembly 4230) removal and replacement from outer shaft assembly 4212.

Inner shaft assembly 4214 of surgical instrument 4200 is constructed and operates similar to instrument drive shaft 1020 of surgical instrument 1000 described above (see FIGS. 8A-10, for example), but includes a recessed segment 4214*a* that defines proximal and distal abutments 4214*b*, 4214*c* at respective proximal and distal ends thereof. Lock body 4216*b* of insert lock assembly 4216 of outer tube assembly 4214 is positioned to engage proximal and distal abutments 4214*b*, 4214*c* of recessed segment 4214*a* as inner shaft assembly 4214 moves axially relative to outer tube assembly 4214 between proximal and distal positions thereof, as indicated by arrow "N," to limit axial movement of inner shaft assembly 4214 relative to outer tube assembly 4214.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument drive assembly for use with a surgical instrument, the instrument drive assembly comprising:
   a housing assembly supporting a drive assembly therein;
   a coupling tube supported at a distal end of the housing assembly and extending distally therefrom;
   a coupling assembly supported in the housing assembly, the coupling assembly configured to releasably couple to an instrument drive shaft of the surgical instrument, wherein the coupling assembly includes a drive link pivotably coupled to the housing assembly and a drive screw of the drive assembly; and
   a retention mechanism configured to releasably couple to an instrument sleeve of the surgical instrument.

2. The instrument drive assembly of claim 1, wherein the retention mechanism is supported in the housing assembly and includes:
   a button slidably coupled to the housing assembly and including a cam arm, the button slidable between a first position and a second position, and
   a latch plate pivotable coupled to the housing assembly and configured to transition between a locked configuration and unlocked configuration with respect to an instrument sleeve of the surgical instrument, the latch plate including an arm configured to engage the cam arm of the button and a portion of the instrument sleeve,
   wherein in the first position of the button the arm of the latch plate is configured to engage a portion of an instrument sleeve, and in the second position of the button the cam arm of the button engages the arm of the latch plate such that the latch plate is configured to pivot out of engagement with a portion of an instrument sleeve.

3. The instrument drive assembly of claim 2, wherein the retention mechanism further includes a first biasing member interposed between the latch plate and the housing assembly such that the latch plate is biased into one of the locked or unlocked configurations.

4. The instrument drive assembly of claim 3, wherein the retention mechanism further includes a second biasing member interposed between the button and the housing assembly such that the button is biased into one of the first or second positions.

5. The instrument drive assembly of claim 1, wherein proximal and distal translation of the drive screw with respect to the housing assembly pivots the drive link between a locked position and an unlocked position.

6. The instrument drive assembly of claim 5, wherein the drive link defines a receiving region thereon, the receiving region including:
   a cavity defined therein, the cavity configured to receive a proximal portion of an instrument drive shaft of the surgical instrument therein;
   a port extending into the cavity, the port configured to receive a proximal portion of an instrument drive shaft of the surgical instrument therethrough; and
   a channel extending along the cavity, the channel configured to receive a portion of an instrument drive shaft of the surgical instrument distal of a proximal portion of an instrument drive shaft of the surgical instrument therein,
   wherein the receiving region of the drive link is configured to releasably couple a proximal portion of an instrument drive shaft of the surgical instrument to the drive link.

7. The instrument drive assembly of claim 6, in the unlocked position of the drive link, the drive screw of the drive assembly is in a distal most position and the drive linked is angled an amount sufficient such that the port of the receiving region of the drive link is oriented to fully receive the proximal portion of an instrument drive shaft, and wherein in the locked position of the drive link the drive screw of the drive assembly is in a position proximal of the distal most position and the port of the receiving region defines an angle with respect to the longitudinal axis of the coupling tube.

8. The instrument drive assembly of claim 7, wherein in the locked position of the drive link, the cavity of the receiving region is configured to retain a proximal portion of an instrument drive shaft of the surgical instrument and the channel of the receiving region is configured to receive a portion of an instrument drive shaft of the surgical instrument distal of a proximal portion of an instrument drive shaft of the surgical instrument.

9. An instrument drive assembly for use with a surgical instrument, the instrument drive assembly comprising:
   a housing assembly supporting a drive assembly therein, wherein the drive assembly includes an engagement assembly having:
      a coupling rod including a proximal portion, a distal portion, and a longitudinal axis defined through a radial center thereof;
      a proximal gear disposed at the proximal portion of the coupling rod and rotationally fixed thereto; and
      a distal gear disposed at the distal portion of the coupling rod and rotationally fixed thereto;
   a coupling tube supported at a distal end of the housing assembly and extending distally therefrom;
   a coupling assembly supported in the housing assembly, the coupling assembly configured to releasably couple to an instrument drive shaft of the surgical instrument; and
   a retention mechanism configured to releasably couple to an instrument sleeve of the surgical instrument.

10. The instrument drive assembly of claim 9, wherein the drive assembly further includes a transfer assembly having:
    a central gear configured to mesh with the distal gear of the engagement assembly; and
    a stem extending distally from the central gear and defining a recess therein.

11. The instrument drive assembly of claim 10, wherein the drive assembly further includes at least two engagement assemblies, a distal gear of each engagement assembly enmeshed with the central gear of the transfer assembly.

12. The instrument drive assembly of claim 10, wherein the drive assembly further includes:
   a coupler defining a threaded aperture, the coupler rotationally affixed within the recess of the stem; and
   a drive screw including a threaded portion and a coupling feature, the threaded portion configured to engage the threated aperture of the coupler and the coupling feature configured to engage the coupling assembly,
   wherein rotation of the proximal gear of the engagement assembly drives rotation of the central gear of the transfer assembly and linear translation of the drive screw with respect to the housing assembly.

13. An instrument drive assembly for use with a surgical instrument, the instrument drive assembly comprising:
   a housing assembly supporting a drive assembly therein, wherein the drive assembly includes an engagement assembly having:
      a coupling rod including a proximal portion, a distal portion, and a longitudinal axis defined through a radial center thereof;
      a proximal gear disposed at the proximal portion of the coupling rod and rotationally fixed thereto; and
      a distal gear disposed at the distal portion of the coupling rod and rotationally fixed thereto;
   a coupling tube supported at a distal end of the housing assembly and extending distally therefrom; and
   a coupling assembly supported in the housing assembly, the coupling assembly configured to releasably couple to an instrument drive shaft of the surgical instrument, wherein the coupling assembly includes:
      a drive link pivotably coupled to the housing assembly and a drive screw of the drive assembly; and
      a retention mechanism configured to releasably couple to an instrument sleeve of the surgical instrument.

14. The instrument drive assembly of claim 13, wherein the drive assembly further includes a transfer assembly having:
   a central gear configured to mesh with the distal gear of the engagement assembly; and
   a stem extending distally from the central gear and defining a recess therein.

15. The instrument drive assembly of claim 14, wherein the drive assembly further includes at least two engagement assemblies, a distal gear of each engagement assembly enmeshed with the central gear of the transfer assembly.

16. The instrument drive assembly of claim 14, wherein the drive assembly further includes:
   a coupler defining a threaded aperture, the coupler rotationally affixed within the recess of the stem; and
   a drive screw including a threaded portion and a coupling feature, the threaded portion configured to engage the threated aperture of the coupler and the coupling feature configured to engage the coupling assembly,
   wherein rotation of the proximal gear of the engagement assembly drives rotation of the central gear of the transfer assembly and linear translation of the drive screw with respect to the housing assembly.

17. The instrument drive assembly of claim 13, wherein the retention mechanism is supported in the housing assembly and includes:
   a button slidably coupled to the housing assembly and including a cam arm, the button slidable between a first position and a second position; and
   a latch plate pivotably coupled to the housing assembly and configured to transition between a locked configuration and unlocked configuration with respect to the instrument sleeve of the surgical instrument, the latch plate including an arm configured to engage the cam arm of the button and a portion of the instrument sleeve,
   wherein in the first position of the button the arm of the latch plate is configured to engage a portion of an instrument sleeve, and in the second position of the button the cam arm of the button engages the arm of the latch plate such that the latch plate is configured to pivot out of engagement with a portion of the instrument sleeve.

18. The instrument drive assembly of claim 17, wherein the retention mechanism further includes a first biasing member interposed between the latch plate and the housing assembly such that the latch plate is biased into one of the locked or unlocked configurations.

19. The instrument drive assembly of claim 18, wherein the retention mechanism further includes a second biasing member interposed between the button and the housing assembly such that the button is biased into one of the first or second positions.

20. The instrument drive assembly of claim 13, wherein proximal and distal translation of the drive screw with respect to the housing assembly pivots the drive link between a locked position and an unlocked position.

* * * * *